(12) United States Patent
Nakamura et al.

(10) Patent No.: US 9,676,820 B2
(45) Date of Patent: Jun. 13, 2017

(54) METHOD FOR INHIBITING PROLIFERATION OF HIGH LIX1L-EXPRESSING TUMOR CELL, AND TUMOR CELL PROLIFERATION-INHIBITING PEPTIDE

(71) Applicant: National University Corporation Hamamatsu University School of Medicine, Shizuoka (JP)

(72) Inventors: Satoki Nakamura, Shizuoka (JP); Haruhiko Sugimura, Shizuoka (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 0 days.

(21) Appl. No.: 14/783,050

(22) PCT Filed: Apr. 2, 2014

(86) PCT No.: PCT/JP2014/059780
§ 371 (c)(1),
(2) Date: Oct. 7, 2015

(87) PCT Pub. No.: WO2014/168064
PCT Pub. Date: Oct. 16, 2014

(65) Prior Publication Data
US 2016/0046669 A1 Feb. 18, 2016

(30) Foreign Application Priority Data

Apr. 10, 2013 (JP) ................................ 2013-082272
Aug. 23, 2013 (JP) ................................ 2013-173696

(51) Int. Cl.
*C12N 15/113* (2010.01)
*C07K 7/06* (2006.01)
*C07K 14/47* (2006.01)
*A61K 38/00* (2006.01)

(52) U.S. Cl.
CPC ............... *C07K 7/06* (2013.01); *C07K 14/47* (2013.01); *C12N 15/113* (2013.01); *A61K 38/00* (2013.01); *C12N 2310/14* (2013.01); *C12N 2320/30* (2013.01)

(58) Field of Classification Search
CPC ............................ C12N 15/111; C12N 15/113
See application file for complete search history.

(56) References Cited

FOREIGN PATENT DOCUMENTS

| JP | A-05-271290 | 10/1993 |
|---|---|---|
| JP | A-05-320200 | 12/1993 |
| JP | A-2009-528826 | 8/2009 |
| JP | A-2010-268690 | 12/2010 |
| WO | WO2007101306 A1 | 9/2007 |

OTHER PUBLICATIONS

Genbank Accession No. AAH35727.1 (Submitted Dec. 22, 2006).*
Strausberg et al. (PNAS (2002) 96(26):16899-16903).*
Nakamura et al. (Scientific Reports (2015) vol. 5, article No. 13474, 20 pages).*
Grigoriadis, A., et al., "Molecular characterisation of cell line models for triple-negative breast cancers," BMC Genomics, 2012, 13:619, pp. 1-14.
International Search Report of PCT/JP2014/059780, mailed Jul. 1, 2014.
Hiromura, M., et al., "Inhibition of Akt Kinase Activity by a Peptide Spanning the βA Strand of the Proto-oncogene TCL1," The Journal of Biological Chemistry, vol. 279, No. 51, pp. 53407-53418.
Xiaozhong, W., et al, "Targeted Blockage of Signal Transducer and Activator of Transcription 5 Signaling Pathway with Decoy Oligodeoxynucleotides Suppresses Leukemic K562 Cell Growth," DNA and Cell Biology, vol. 30, No. 2 (2011), pp. 71-78.
Souissi, I., et al. "A STAT3-decoy oligonucleotide induces cell death in a human colorectal carcinoma cell line by blocking nuclear transfer of STAT3 and STAT3-bound Nf-κB," BMC Cell Biology (2011), 12:14, pp. 1-18.
Levitzki, Alexander, et al. "Tyrphostins and Other Tyrosine Kinase Inhibitors", Annual Review of Biochemistry, vol. 75, No. 1, (Jun. 1, 2006), pp. 93-109, XP055293930, DOI: 10.1146/annurev.biochem.75.103004.142657.
Database Uniprot: Q8IVB5 [Online] Apr. 18, 2006, "RecName: Full=LIX1-like protein", XP-002760565, retrieved from EBI accession No. UNIPROT:Q8IVB5 Database accession No. Q8IVB5.
Kernagis, Dawn N., et al. "Genes with Bimodal Expression are Robust Diagnostic Targets that Define Distinct Subtypes of Epithelial Ovarian Cancer with Different Overall Survival", The Journal of Molecular Diagnostics, vol. 14, No. 3, May 1, 2012, pp. 214-222, XP055293874, ISSN: 1525-1578, DOI: 10.1016/j.jmoldx.2012.01.007.
Extended European Search Report (EESR) for EP 14 782 200.4, dated Aug. 30, 2016.
Partial Translation of Japanese Office Action dated Dec. 13, 2016, JP Appl. No. 2015-511230 (7 pages).
Genbank Accession No. AES01134.1 (Uploaded Feb. 22, 2012).

* cited by examiner

*Primary Examiner* — J. E. Angell
(74) *Attorney, Agent, or Firm* — Honigman Miller Schwartz and Cohn LLP; Fernando Alberdi; Jonathan P. O'Brien

(57) ABSTRACT

A method is provided for inhibiting proliferation of a high LIX1L-expressing tumor cell, in which the expression or function of a LIX1L gene with respect to a tumor cell highly expressing the LIX1L gene is inhibited.

5 Claims, 36 Drawing Sheets

FIG. 5A

LIXIL shRNA #1

Target sense sequence    Hairpin loop    Target antisense sequence    Terminator 5'-GAGGAGGTGTTGGCTCATTATTTTCAAGAGAAATAATGAGCCAACACCTCCTCTTTTT-3'
3'-CTCCTCCACAACCGAGTAATAAAAGTTCTCTTTATTACTCGGTTGTGGAGGAGAAAAAA-5'

*FIG. 5B*

LIX1L shRNA #2

Target sense sequence     Hairpin loop  Target antisense sequence  Terminator

5'  -GAGTCCCGTGGTGCTGACTTAATTCAAGAGATTAAGTCAGCACCACGGGACTCTTTTT-3'
3'  -CTCAGGGCACCACGACTGAATTTTCAAGAGAAATTCAGTCGTGGTGCCCTGAGAAAAAA-3'

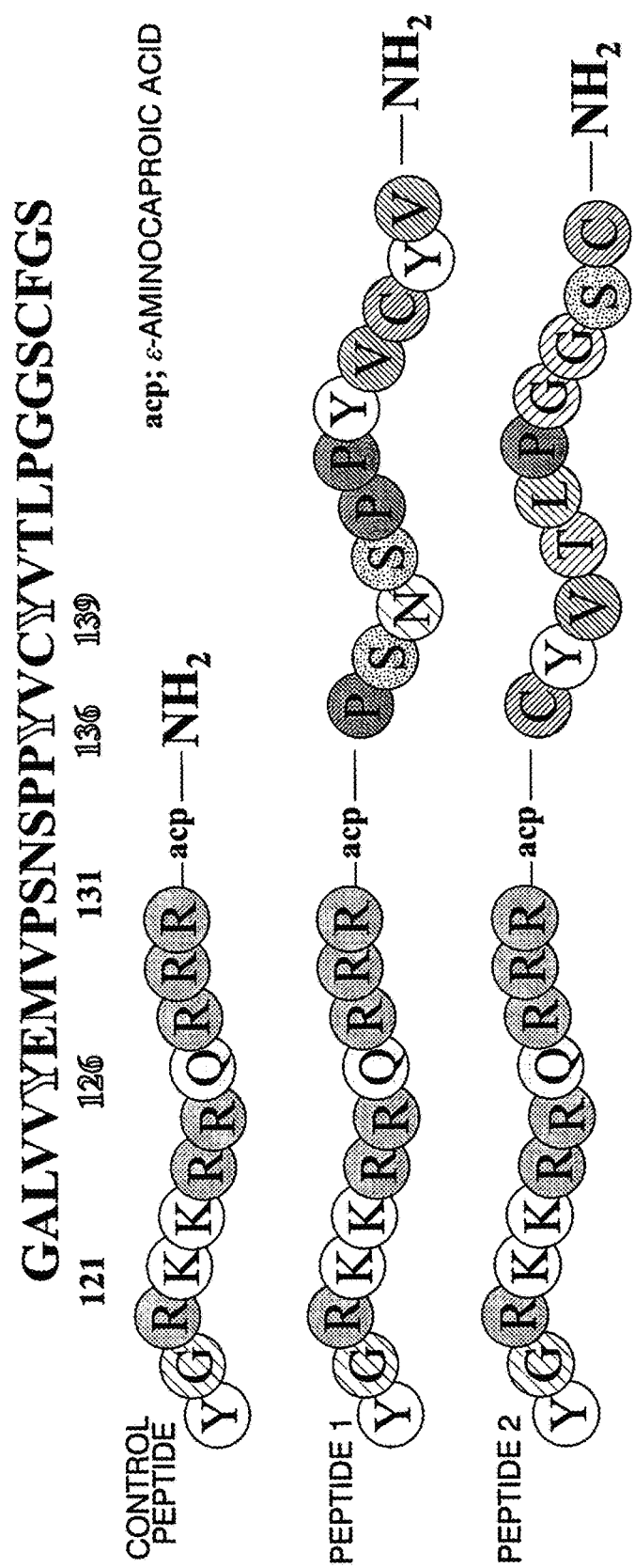

FIG. 13A

LIX1L

METMRAQRLQ PGVGTSGRGT LRALRPGVTG AAAATATPPA GPPPAPPPPA PPPPPLLLSG
APGLPLPPGA AGSPAVLREA VEAVVRSFAK HTQGYGRVNV VEALQEFWQM KQSRGADLKN
GALVVYEMVP SNSPPPYVCYV TLPGGSCFGS FQFCPTKAEA RRSAAKIALM NSVFNEHPSR
RITDEFIEKS VSEALASFNG NREEADNPNT GIGAFRFMLE SNKGKSMLEF QELMTVFQLL
HWNGSLKAMR ERQCSRQEVL AHYSHRALDD DIRHQMALDW VSREQSVPGA LSRELASTER
ELDEARLAGK ELRFHKEKKD ILVLAAGQLG NMHSSNC

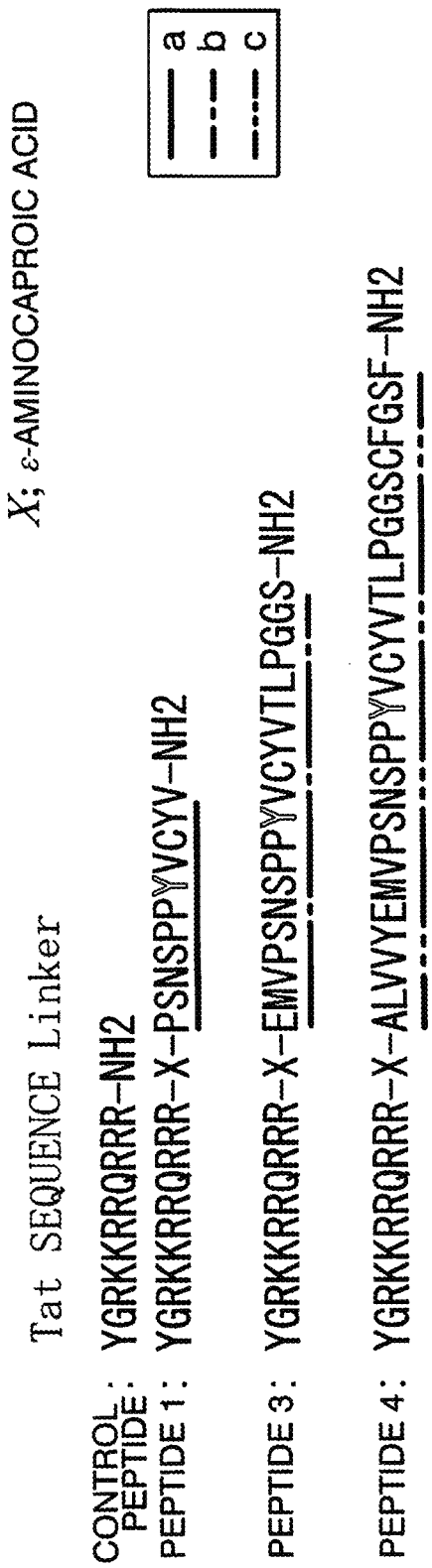

SEQUENCE LISTING

```
<160> NUMBER OF SEQ ID NOS: 29

<210> SEQ ID NO 1
<211> LENGTH: 337
<212> TYPE: PRT
<213> ORGANISM: Homo sapiens

<400> SEQUENCE: 1

Met Glu Thr Met Arg Ala Gln Arg Leu Gln Pro Gly Val Gly Thr Ser
1               5                   10                  15

Gly Arg Gly Thr Leu Arg Ala Leu Arg Pro Gly Val Thr Gly Ala Ala
            20                  25                  30

Ala Ala Thr Ala Thr Pro Pro Ala Gly Pro Pro Pro Ala Pro Pro Pro
        35                  40                  45

Pro Ala Pro Pro Pro Pro Leu Leu Leu Ser Gly Ala Pro Gly Leu
    50                  55                  60

Pro Leu Pro Pro Gly Ala Ala Gly Ser Pro Ala Val Leu Arg Glu Ala
65                  70                  75                  80

Val Glu Ala Val Val Arg Ser Phe Ala Lys His Thr Gln Gly Tyr Gly
                85                  90                  95

Arg Val Asn Val Val Glu Ala Leu Gln Glu Phe Trp Gln Met Lys Gln
            100                 105                 110

Ser Arg Gly Ala Asp Leu Lys Asn Gly Ala Leu Val Val Tyr Glu Met
        115                 120                 125
```

```
Val Pro Ser Asn Ser Pro Pro Tyr Val Cys Tyr Val Thr Leu Pro Gly
    130                 135                 140

Gly Ser Cys Phe Gly Ser Phe Gln Phe Cys Pro Thr Lys Ala Glu Ala
145                 150                 155                 160

Arg Arg Ser Ala Ala Lys Ile Ala Leu Met Asn Ser Val Phe Asn Glu
                165                 170                 175

His Pro Ser Arg Arg Ile Thr Asp Glu Phe Ile Glu Lys Ser Val Ser
            180                 185                 190

Glu Ala Leu Ala Ser Phe Asn Gly Asn Arg Glu Ala Asp Asn Pro
        195                 200                 205

Asn Thr Gly Ile Gly Ala Phe Arg Phe Met Leu Glu Ser Asn Lys Gly
    210                 215                 220

Lys Ser Met Leu Glu Phe Gln Glu Leu Met Thr Val Phe Gln Leu Leu
225                 230                 235                 240

His Trp Asn Gly Ser Leu Lys Ala Met Arg Glu Arg Gln Cys Ser Arg
                245                 250                 255

Gln Glu Val Leu Ala His Tyr Ser His Arg Ala Leu Asp Asp Ile
        260                 265                 270

Arg His Gln Met Ala Leu Asp Trp Val Ser Arg Glu Gln Ser Val Pro
    275                 280                 285

Gly Ala Leu Ser Arg Glu Leu Ala Ser Thr Glu Arg Glu Leu Asp Glu
    290                 295                 300

Ala Arg Leu Ala Gly Lys Glu Leu Arg Phe His Lys Glu Lys Lys Asp
305                 310                 315                 320

Ile Leu Val Leu Ala Ala Gly Gln Leu Gly Asn Met His Ser Ser Asn
                325                 330                 335

Cys

<210> SEQ ID NO 2
<211> LENGTH: 1014
<212> TYPE: DNA
<213> ORGANISM: Homo sapiens

<400> SEQUENCE: 2
atggagacta tgcgagcgca gcggctgcag cctggtgtgg gcaccagcgg gaggggcact    60
ctccgagcgc tgcggcccgg agtgactggg gccgcggctg ccaccgccac accccctgcg   120
ggccccccgc ctgccccgcc gcctcccgca ccgcccccgc cgccgctgct cctgtctggg   180
gccccaggac taccctgcc cccggcgcc gccggcagcc cggcagtgct gcgagaggcc    240
gtggaggccg tggtgaggag cttcgccaag cacacgcagg gctatggccg agtgaatgtg   300
gtggaggcac ttcaggaatt ctggcagatg aagcagtccc gtggtgctga cttaaagaat   360
ggggctctag tggtttatga gatggttccc tccaacagcc tcctatgt ctgctatgtc    420 accctgcctg ggggaagctg ctttgggagt ttccagtttt gccccacaaa agctgaggcc   480
cggaggagtc tgcaaagat tgcgctaatg aattctgtgt taatgaaca tccttcccga    540 agaatcactg atgagttcat cgagaagagt gtctctgagg ccctggcatc ttttaatggc   600
aacagggagg aagctgacaa cccaaataca gggattggtg ccttccgatt catgctggaa   660
tccaacaagg gcaaatcaat gttggagttc caggagctaa tgacagtttt tcaactgcta   720
cactggaatg gcagccttaa ggccatgagg gaacgacaat gctctcggca ggaggtgttg   780
gctcattatt cgcaccgggc cctggatgat gatattcgcc accaaatggc cttggactgg   840
gtgagccggg agcagagtgt gccgggggca ctgtctagag agctgccctc tactgagcgg   900
```

```
gagctggatg aagcccgact ggcaggcaag gagctgcgct tccacaagga gaagaaagat    960
attcttgtgc tggctgctgg gcagttgggc aatatgcatt cttccaactg ctag         1014
```

<210> SEQ ID NO 3
<211> LENGTH: 21
<212> TYPE: DNA
<213> ORGANISM: Artificial Sequence
<220> FEATURE:
<223> OTHER INFORMATION: RNAi-target region #1 of LIX1L

<400> SEQUENCE: 3

```
aggaggtgtt ggctcattat t                                              21
```

<210> SEQ ID NO 4
<211> LENGTH: 21
<212> TYPE: DNA
<213> ORGANISM: Artificial Sequence
<220> FEATURE:
<223> OTHER INFORMATION: RNAi-target region #2 of LIX1L

<400> SEQUENCE: 4

```
agtcccgtgg tgctgactta a                                              21
```

<210> SEQ ID NO 5
<211> LENGTH: 59
<212> TYPE: DNA
<213> ORGANISM: Artificial Sequence
<220> FEATURE:
<223> OTHER INFORMATION: shRNA #1

<400> SEQUENCE: 5

```
gaggaggtgt tggctcatta ttttcaagag aaataatgag ccaacacctc ctcttttt     59
```

<210> SEQ ID NO 6
<211> LENGTH: 59
<212> TYPE: DNA
<213> ORGANISM: Artificial Sequence
<220> FEATURE:
<223> OTHER INFORMATION: shRNA #2

<400> SEQUENCE: 6

```
gagtcccgtg gtgctgactt aattcaagag attaagtcag caccacggga ctcttttt     59
```

<210> SEQ ID NO 7
<211> LENGTH: 11
<212> TYPE: PRT
<213> ORGANISM: Artificial Sequence
<220> FEATURE:
<223> OTHER INFORMATION: Tat peptide

<400> SEQUENCE: 7

Tyr Gly Arg Lys Lys Arg Arg Gln Arg Arg Arg
1               5                   10

<210> SEQ ID NO 8
<211> LENGTH: 20
<212> TYPE: DNA
<213> ORGANISM: Artificial Sequence
<220> FEATURE:
<223> OTHER INFORMATION: LIX1L Forward Primer

<400> SEQUENCE: 8

```
gggaggggca ctctccgagc                                                20
```

<210> SEQ ID NO 9

```
<211> LENGTH: 20
<212> TYPE: DNA
<213> ORGANISM: Artificial Sequence
<220> FEATURE:
<223> OTHER INFORMATION: LIX1L Reverse Primer

<400> SEQUENCE: 9
gcgaagctcc tcaccacggc                                                     20

<210> SEQ ID NO 10
<211> LENGTH: 22
<212> TYPE: DNA
<213> ORGANISM: Artificial Sequence
<220> FEATURE:
<223> OTHER INFORMATION: GAPDH Forward Primer

<400> SEQUENCE: 10
gaacagcaac gagtaccggg ta                                                  22

<210> SEQ ID NO 11
<211> LENGTH: 21
<212> TYPE: DNA
<213> ORGANISM: Artificial Sequence
<220> FEATURE:
<223> OTHER INFORMATION: GAPDH Reverse Primer

<400> SEQUENCE: 11
cccatggcct tgaccaagga g                                                   21

<210> SEQ ID NO 12
<211> LENGTH: 23
<212> TYPE: PRT
<213> ORGANISM: Artificial Sequence
<220> FEATURE:
<223> OTHER INFORMATION: peptide 1
<220> FEATURE:
<221> NAME/KEY: misc_feature
<222> LOCATION: (12)..(12)
<223> OTHER INFORMATION: Xaa can be any naturally occurring amino acid

<400> SEQUENCE: 12

Tyr Gly Arg Lys Lys Arg Arg Gln Arg Arg Xaa Pro Ser Asn Ser
1               5                   10                  15

Pro Pro Tyr Val Cys Tyr Val
            20

<210> SEQ ID NO 13
<211> LENGTH: 22
<212> TYPE: PRT
<213> ORGANISM: Artificial Sequence
<220> FEATURE:
<223> OTHER INFORMATION: peptide 2
<220> FEATURE:
<221> NAME/KEY: misc_feature
<222> LOCATION: (12)..(12)
<223> OTHER INFORMATION: Xaa can be any naturally occurring amino acid

<400> SEQUENCE: 13

Tyr Gly Arg Lys Lys Arg Arg Gln Arg Arg Xaa Cys Tyr Val Thr
1               5                   10                  15

Leu Pro Gly Gly Ser Cys
            20

<210> SEQ ID NO 14
<211> LENGTH: 12
<212> TYPE: PRT
<213> ORGANISM: Artificial Sequence
```

-continued

```
<220> FEATURE:
<223> OTHER INFORMATION: control peptide
<220> FEATURE:
<221> NAME/KEY: misc_feature
<222> LOCATION: (12)..(12)
<223> OTHER INFORMATION: Xaa can be any naturally occurring amino acid

<400> SEQUENCE: 14

Tyr Gly Arg Lys Lys Arg Arg Gln Arg Arg Xaa
1               5                   10

<210> SEQ ID NO 15
<211> LENGTH: 32
<212> TYPE: PRT
<213> ORGANISM: Artificial Sequence
<220> FEATURE:
<223> OTHER INFORMATION: peptide 3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 15

Tyr Gly Arg Lys Lys Arg Arg Gln Arg Arg Xaa Glu Met Val Pro
1               5                   10                  15

Ser Asn Ser Pro Pro Tyr Val Cys Tyr Val Thr Leu Pro Gly Gly Ser
                20                  25                  30

<210> SEQ ID NO 16
<211> LENGTH: 42
<212> TYPE: PRT
<213> ORGANISM: Artificial Sequence
<220> FEATURE:
<223> OTHER INFORMATION: peptide 4
<220> FEATURE:
<221> NAME/KEY: misc_feature
<222> LOCATION: (12)..(12)
<223> OTHER INFORMATION: Xaa can be any naturally occurring amino acid

<400> SEQUENCE: 16

Tyr Gly Arg Lys Lys Arg Arg Gln Arg Arg Xaa Ala Leu Val Val
1               5                   10                  15

Tyr Glu Met Val Pro Ser Asn Ser Pro Pro Tyr Val Cys Tyr Val Thr
                20                  25                  30

Leu Pro Gly Gly Ser Cys Phe Gly Ser Phe
            35                  40

<210> SEQ ID NO 17
<211> LENGTH: 345
<212> TYPE: PRT
<213> ORGANISM: Artificial Sequence
<220> FEATURE:
<223> OTHER INFORMATION: FLG/LIX1L

<400> SEQUENCE: 17

Asp Tyr Lys Asp Asp Asp Lys Met Glu Thr Met Arg Ala Gln Arg
1               5                   10                  15

Leu Gln Pro Gly Val Gly Thr Ser Gly Arg Gly Thr Leu Arg Ala Leu
                20                  25                  30

Arg Pro Gly Val Thr Gly Ala Ala Ala Thr Ala Thr Pro Pro Ala
            35                  40                  45

Gly Pro Pro Pro Ala Pro Pro Pro Ala Pro Pro Pro Pro Leu
        50                  55                  60

Leu Leu Ser Gly Ala Pro Gly Leu Pro Leu Pro Pro Gly Ala Ala Gly
65                  70                  75                  80
```

```
Ser Pro Ala Val Leu Arg Glu Ala Val Glu Ala Val Val Arg Ser Phe
                85                  90                  95

Ala Lys His Thr Gln Gly Tyr Gly Arg Val Asn Val Val Glu Ala Leu
                100                 105                 110

Gln Glu Phe Trp Gln Met Lys Gln Ser Arg Gly Ala Asp Leu Lys Asn
            115                 120                 125

Gly Ala Leu Val Val Tyr Glu Met Val Pro Ser Asn Ser Pro Pro Tyr
        130                 135                 140

Val Cys Tyr Val Thr Leu Pro Gly Gly Ser Cys Phe Gly Ser Phe Gln
145                 150                 155                 160

Phe Cys Pro Thr Lys Ala Glu Ala Arg Arg Ser Ala Ala Lys Ile Ala
                165                 170                 175

Leu Met Asn Ser Val Phe Asn Glu His Pro Ser Arg Arg Ile Thr Asp
                180                 185                 190

Glu Phe Ile Glu Lys Ser Val Ser Glu Ala Leu Ala Ser Phe Asn Gly
            195                 200                 205

Asn Arg Glu Glu Ala Asp Asn Pro Asn Thr Gly Ile Gly Ala Phe Arg
    210                 215                 220

Phe Met Leu Glu Ser Asn Lys Gly Lys Ser Met Leu Glu Phe Gln Glu
225                 230                 235                 240

Leu Met Thr Val Phe Gln Leu Leu His Trp Asn Gly Ser Leu Lys Ala
                245                 250                 255

Met Arg Glu Arg Gln Cys Ser Arg Gln Glu Val Leu Ala His Tyr Ser
                260                 265                 270

His Arg Ala Leu Asp Asp Asp Ile Arg His Gln Met Ala Leu Asp Trp
            275                 280                 285

Val Ser Arg Glu Gln Ser Val Pro Gly Ala Leu Ser Arg Glu Leu Ala
    290                 295                 300

Ser Thr Glu Arg Glu Leu Asp Glu Ala Arg Leu Ala Gly Lys Glu Leu
305                 310                 315                 320

Arg Phe His Lys Glu Lys Lys Asp Ile Leu Val Leu Ala Ala Gly Gln
                325                 330                 335

Leu Gly Asn Met His Ser Ser Asn Cys
                340                 345

<210> SEQ ID NO 18
<211> LENGTH: 16
<212> TYPE: PRT
<213> ORGANISM: Artificial Sequence
<220> FEATURE:
<223> OTHER INFORMATION: peptide 5
<220> FEATURE:
<221> NAME/KEY: misc_feature
<222> LOCATION: (12)..(12)
<223> OTHER INFORMATION: Xaa can be any naturally occurring amino acid

<400> SEQUENCE: 18

Tyr Gly Arg Lys Lys Arg Arg Gln Arg Arg Xaa Pro Ser Asn Ser
1               5                   10                  15

<210> SEQ ID NO 19
<211> LENGTH: 22
<212> TYPE: PRT
<213> ORGANISM: Artificial Sequence
<220> FEATURE:
<223> OTHER INFORMATION: peptide 6
<220> FEATURE:
<221> NAME/KEY: misc_feature
<222> LOCATION: (12)..(12)
```

-continued

```
<223> OTHER INFORMATION: Xaa can be any naturally occurring amino acid

<400> SEQUENCE: 19

Tyr Gly Arg Lys Lys Arg Arg Gln Arg Arg Xaa His Thr Gln Gly
1               5                   10                  15

Tyr Gly Arg Val Asn Val
            20

<210> SEQ ID NO 20
<211> LENGTH: 22
<212> TYPE: PRT
<213> ORGANISM: Artificial Sequence
<220> FEATURE:
<223> OTHER INFORMATION: peptide 7
<220> FEATURE:
<221> NAME/KEY: misc_feature
<222> LOCATION: (12)..(12)
<223> OTHER INFORMATION: Xaa can be any naturally occurring amino acid

<400> SEQUENCE: 20

Tyr Gly Arg Lys Lys Arg Arg Gln Arg Arg Xaa Gly Val Gly Thr
1               5                   10                  15

Ser Gly Arg Gly Thr Leu
            20

<210> SEQ ID NO 21
<211> LENGTH: 22
<212> TYPE: PRT
<213> ORGANISM: Artificial Sequence
<220> FEATURE:
<223> OTHER INFORMATION: peptide 8
<220> FEATURE:
<221> NAME/KEY: misc_feature
<222> LOCATION: (12)..(12)
<223> OTHER INFORMATION: Xaa can be any naturally occurring amino acid

<400> SEQUENCE: 21

Tyr Gly Arg Lys Lys Arg Arg Gln Arg Arg Xaa Glu Ala Arg Arg
1               5                   10                  15

Ser Ala Ala Lys Ile Ala
            20

<210> SEQ ID NO 22
<211> LENGTH: 22
<212> TYPE: PRT
<213> ORGANISM: Artificial Sequence
<220> FEATURE:
<223> OTHER INFORMATION: peptide 9
<220> FEATURE:
<221> NAME/KEY: misc_feature
<222> LOCATION: (12)..(12)
<223> OTHER INFORMATION: Xaa can be any naturally occurring amino acid

<400> SEQUENCE: 22

Tyr Gly Arg Lys Lys Arg Arg Gln Arg Arg Xaa Asn Glu His Pro
1               5                   10                  15

Ser Arg Arg Ile Thr Asp
            20

<210> SEQ ID NO 23
<211> LENGTH: 22
<212> TYPE: PRT
<213> ORGANISM: Artificial Sequence
<220> FEATURE:
<223> OTHER INFORMATION: peptide 10
<220> FEATURE:
<221> NAME/KEY: misc_feature
```

```
<222> LOCATION: (12)..(12)
<223> OTHER INFORMATION: Xaa can be any naturally occurring amino acid

<400> SEQUENCE: 23

Tyr Gly Arg Lys Lys Arg Arg Gln Arg Arg Xaa Phe Ile Glu Lys
1               5                   10                  15

Ser Val Ser Glu Ala Leu
            20

<210> SEQ ID NO 24
<211> LENGTH: 22
<212> TYPE: PRT
<213> ORGANISM: Artificial Sequence
<220> FEATURE:
<223> OTHER INFORMATION: peptide 11
<220> FEATURE:
<221> NAME/KEY: misc_feature
<222> LOCATION: (12)..(12)
<223> OTHER INFORMATION: Xaa can be any naturally occurring amino acid

<400> SEQUENCE: 24

Tyr Gly Arg Lys Lys Arg Arg Gln Arg Arg Xaa Asn Lys Gly Lys
1               5                   10                  15

Ser Met Leu Glu Phe Gln
            20

<210> SEQ ID NO 25
<211> LENGTH: 22
<212> TYPE: PRT
<213> ORGANISM: Artificial Sequence
<220> FEATURE:
<223> OTHER INFORMATION: peptide 12
<220> FEATURE:
<221> NAME/KEY: misc_feature
<222> LOCATION: (12)..(12)
<223> OTHER INFORMATION: Xaa can be any naturally occurring amino acid

<400> SEQUENCE: 25

Tyr Gly Arg Lys Lys Arg Arg Gln Arg Arg Xaa Glu Arg Gln Cys
1               5                   10                  15

Ser Arg Gln Glu Val Leu
            20

<210> SEQ ID NO 26
<211> LENGTH: 22
<212> TYPE: PRT
<213> ORGANISM: Artificial Sequence
<220> FEATURE:
<223> OTHER INFORMATION: peptide 13
<220> FEATURE:
<221> NAME/KEY: misc_feature
<222> LOCATION: (12)..(12)
<223> OTHER INFORMATION: Xaa can be any naturally occurring amino acid

<400> SEQUENCE: 26

Tyr Gly Arg Lys Lys Arg Arg Gln Arg Arg Xaa Asp Trp Val Ser
1               5                   10                  15

Arg Glu Gln Ser Val Pro
            20

<210> SEQ ID NO 27
<211> LENGTH: 22
<212> TYPE: PRT
<213> ORGANISM: Artificial Sequence
<220> FEATURE:
<223> OTHER INFORMATION: peptide 14
<220> FEATURE:
```

```
<221> NAME/KEY: misc_feature
<222> LOCATION: (12)..(12)
<223> OTHER INFORMATION: Xaa can be any naturally occurring amino acid

<400> SEQUENCE: 27

Tyr Gly Arg Lys Lys Arg Arg Gln Arg Arg Xaa Ala Leu Ser Arg
1               5                   10                  15

Glu Leu Ala Ser Thr Glu
            20

<210> SEQ ID NO 28
<211> LENGTH: 22
<212> TYPE: PRT
<213> ORGANISM: Artificial Sequence
<220> FEATURE:
<223> OTHER INFORMATION: peptide 15
<220> FEATURE:
<221> NAME/KEY: misc_feature
<222> LOCATION: (12)..(12)
<223> OTHER INFORMATION: Xaa can be any naturally occurring amino acid

<400> SEQUENCE: 28

Tyr Gly Arg Lys Lys Arg Arg Gln Arg Arg Xaa Val Gly Thr Ser
1               5                   10                  15

Gly Arg Gly Thr Leu Arg
            20

<210> SEQ ID NO 29
<211> LENGTH: 22
<212> TYPE: PRT
<213> ORGANISM: Artificial Sequence
<220> FEATURE:
<223> OTHER INFORMATION: peptide 16
<220> FEATURE:
<221> NAME/KEY: misc_feature
<222> LOCATION: (12)..(12)
<223> OTHER INFORMATION: Xaa can be any naturally occurring amino acid

<400> SEQUENCE: 29

Tyr Gly Arg Lys Lys Arg Arg Gln Arg Arg Xaa Glu Leu Ala Ser
1               5                   10                  15

Thr Glu Arg Glu Leu Asp
            20
```

METHOD FOR INHIBITING PROLIFERATION OF HIGH LIX1L-EXPRESSING TUMOR CELL, AND TUMOR CELL PROLIFERATION-INHIBITING PEPTIDE

CROSS-REFERENCE TO RELATED APPLICATIONS

This application is a 35 U.S.C. §371 United States national phase application of PCT International Application No. PCT/JP2014/059780, filed Apr. 2, 2014, which claims the benefit of priority to Japanese Patent Application No. 2013-082272, filed Apr. 10, 2013, and Japanese Patent Application No. 2013-173696, filed Aug. 23, 2013. The contents of the above-referenced applications are incorporated herein by reference in their entireties.

INCORPORATION BY REFERENCE OF MATERIAL SUBMITTED ELECTRONICALLY

Incorporated by reference in its entirety is a computer-readable sequence listing submitted concurrently herewith and identified as follows: One 16.1 KB ASCII (Text) file named "260487-377709_Sequence_Listing_ST25.txt" created on Oct. 6, 2015 at 2:30 pm.

BACKGROUND ART

Currently, many anti-tumor agents such as antimetabolites (Ara-C, methotrexate, or the like), plant alkaloids (vincristine), alkylating agents (endoxan), anticancer antibiotics (adriamycin, idarubicin mitomycin, or the like), and platinum agents (cisplatin) which are used in malignant tumors are known. Among these, examples of polypeptide agents include human interferon-γ polypeptides (for example, refer to PTL 1) or polypeptides (for example, refer to PTL 2) formed of a human tumor necrosis factor (TNF) or a part of a converter of the human tumor necrosis factor. Particularly, in recent years, remarkable progress in molecular-targeted therapeutic agents (imatinib or the like) with high tumor specificity, monoclonal antibodies (rituximab or the like), or the like has been recognized and the therapeutic effects thereof have also become high. However, the spectrum of an anti-tumor effect of the anti-tumor agent such as imatinib is narrow and a drug should be selected for each tumor. In addition, there is also a problem of drug resistance. For this reason, a more effective drug of which the spectrum of an anti-tumor effect is wide has been expected in the medical field.

In contrast, a human LIX1L gene (Lix1 homolog-like; hereinafter, in some cases, also referred to as hLIX1L) is a structural gene that encodes LIX1L protein consisting of 337 amino acids. Although the molecular biological role of LIX1L is still unclear, it has been reported that the expression level thereof varies depending on the type of cell. For example, in PTL 3, there is a report that a LIX1L gene is one of 266 kinds of genes in which there is a statistically significant difference ($P<1.0\times10^{-5}$) in the expression level, in a cell which is sensitive to a compound, which is an AhR agonist and is activated by CYP1A1, and in a cell which is not sensitive to the compound. In addition, in PTL 4, there is an example of a LIX1L gene as one gene out of many gene groups in which the expression level increases or decreases in accordance with allergies.

CITATION LIST

Patent Literature

[PTL 1] Japanese Unexamined Patent Application, First Publication No. S5-320200
[PTL 2] Japanese Unexamined Patent Application, First Publication No. S5-271290
[PTL 3] Japanese Unexamined Patent Application, First Publication No. 2010-268690
[PTL 4] Published Japanese Translation No. 2009-528826 of the PCT International Publication

SUMMARY OF INVENTION

Technical Problem

An object of the present invention is to provide a new polypeptide having a wide spectrum of an anti-tumor effect, and a method for inhibiting cell proliferation of a tumor cell using the polypeptide.

Solution to Problem

The present inventors have completed the present invention by conducting extensive studies in order to solve the above-described problems, and as a result, they have found that, in a high LIX1L-expressing tumor cell, cell proliferation is inhibited by inhibiting the expression of a LIX1L gene; a partial peptide including a specific tyrosine residue of LIX1L has a cell proliferation inhibitory action of the high LIX1L-expressing tumor cell; and the partial peptide has the cell proliferation inhibitory action of the high LIX1L-expressing tumor cell by inhibiting phosphorylation of a specific tyrosine residue of a LIX1L protein.

(1) A first aspect of the present invention is a method for inhibiting proliferation of a high LIX1L-expressing tumor cell, including: inhibiting the expression or function of a LIX1L gene with respect to a tumor cell highly expressing the LIX1L gene.

(2) In the method for inhibiting proliferation of a high LIX1L-expressing tumor cell of (1), it is preferable to inhibit the expression of the LIX1L gene through RNA interference.

(3) In the method for inhibiting proliferation of a high LIX1L-expressing tumor cell of (2), it is preferable to perform RNA interference using shRNA or siRNA which includes a base sequence represented by SEQ ID No: 3 or 4, or a vector which produces the shRNA or the siRNA in a cell.

(4) A second aspect of the present invention is a tumor cell proliferation-inhibiting peptide including: a polypeptide consisting of a partial sequence which is a partial sequence of the amino acid sequence represented by SEQ ID No: 1 and includes the 136th tyrosine.

(5) As the tumor cell proliferation-inhibiting peptide of (4), it is preferable that the polypeptide which consists of the partial sequence including the 136th tyrosine and a site which has cell membrane permeability be directly or indirectly bonded to each other.

(6) As the tumor cell proliferation-inhibiting peptide of (4) or (5), it is preferable that the partial sequence including the 136th tyrosine consist of 8 or more amino acids.

(7) As the tumor cell proliferation-inhibiting peptide of (5) or (6), it is preferable that the site having the cell membrane permeability be a peptide consisting of the amino acid sequence represented by SEQ ID No: 7.

(8) A third aspect of the present invention is a pharmaceutical composition having the tumor cell proliferation-inhibiting peptide according to any one of (4) to (7) as an active ingredient.

(9) The pharmaceutical composition of (8) is preferably an anti-tumor agent.

(10) A fourth aspect of the present invention is a method for inhibiting proliferation of a high LIX1L-expressing tumor cell, including: introducing the tumor cell proliferation-inhibiting peptide according to any one of (4) to (7) into a high LIX1L-expressing tumor cell.

That is, the present invention relates to the following.

[1] A method for inhibiting proliferation of a high LIX1L-expressing tumor cell, including:
 inhibiting the expression or function of a LIX1L gene with respect to a tumor cell highly expressing the LIX1L gene.

[2] The method for inhibiting proliferation of a high LIX1L-expressing tumor cell according to [1],
 in which the expression of a LIX1L gene is inhibited through RNA interference.

[3] The method for inhibiting proliferation of a high LIX1L-expressing tumor cell according to [2],
 in which the inhibition of the expression of a LIX1L gene through RNA interference includes introduction of shRNA or siRNA which consists of a base sequence represented by SEQ ID No: 3 or 4, or a vector which produces the shRNA or the siRNA in a cell, into the cell.

[4] The method for inhibiting proliferation of a high LIX1L-expressing tumor cell according to [1], further including:
 inhibiting phosphorylation of tyrosine of a LIX1L protein.

[5] The method for inhibiting proliferation of a high LIX1L-expressing tumor cell according to [4],
 in which the tyrosine is the 136th tyrosine of the LIX1L protein consisting of an amino acid sequence represented by SEQ ID No: 1.

[6] A tumor cell proliferation-inhibiting peptide including:
 a polypeptide consisting of a partial sequence which is a partial sequence of the amino acid sequence represented by SEQ ID No: 1 and includes the 136th tyrosine.

[7] The tumor cell proliferation-inhibiting peptide according to [6],
 in which the polypeptide which consists of the partial sequence including the 136th tyrosine and a site which has cell membrane permeability are directly or indirectly bonded to each other.

[8] The tumor cell proliferation-inhibiting peptide according to [6] or [7],
 in which the partial sequence including the 136th tyrosine consists of 8 amino acids to 35 amino acids.

[9] The tumor cell proliferation-inhibiting peptide according to [7] or [8],
 in which the site having the cell membrane permeability is a peptide consisting of an amino acid sequence represented by SEQ ID No: 7.

[10] A pharmaceutical composition having the tumor cell proliferation-inhibiting peptide according to any one of [6] to [9] as an active ingredient.

[11] The pharmaceutical composition according to [10], which is used for an anti-tumor agent.

[12] A method for inhibiting proliferation of a high LIX1L-expressing tumor cell, including:
 introducing the tumor cell proliferation-inhibiting peptide according to any one of [6] to [9] into a high LIX1L-expressing tumor cell.

[13] A phosphorylation inhibitor which is inhibited phosphorylation of tyrosine of a LIX1L protein.

[14] The phosphorylation inhibitor according to [13],
 in which the tyrosine is the 136th tyrosine of the LIX1L protein consisting of an amino acid sequence represented by SEQ ID No: 1.

Advantageous Effects of Invention

According to the present invention, it is possible to effectively inhibit the proliferation of a tumor cell by inhibiting the expression or function of a LIX1L gene of a high LIX1L-expressing tumor cell.

Particularly, the tumor cell proliferation-inhibiting peptide as one embodiment of the present invention exhibits a proliferation inhibitory activity with respect to the high LIX1L-expressing tumor cell, but does not exhibit proliferation inhibitory activity with respect to a low LIX1L-expressing tumor cell or a normal cell in which there is almost no expression of a LIX1L gene. That is, although the tumor cell proliferation-inhibiting peptide as one embodiment of the present invention does not exhibit cytotoxicity with respect to the normal cell, the tumor cell proliferation-inhibiting peptide has a wide spectrum of an anti-tumor effect. Therefore, the tumor cell proliferation-inhibiting peptide is extremely useful as an anti-tumor agent and it is possible to efficiently inhibit the proliferation of the high LIX1L-expressing tumor cell using the tumor cell proliferation-inhibiting peptide.

BRIEF DESCRIPTION OF DRAWINGS

FIG. 5A is a view showing a base sequence of shRNA #1 used in Example 1.

FIG. 5B is a view showing a base sequence of shRNA #2 used in Example 1.

FIG. 10 is a view showing an amino acid sequence of a peptide used in Example 2.

FIG. 13A is a view showing an amino acid sequence of a LIX1L protein.

FIG. 13B is a view showing amino acid sequences of peptides 1 to 3 and a control peptide used in Example 4.

DESCRIPTION OF EMBODIMENTS

Figure 1A:
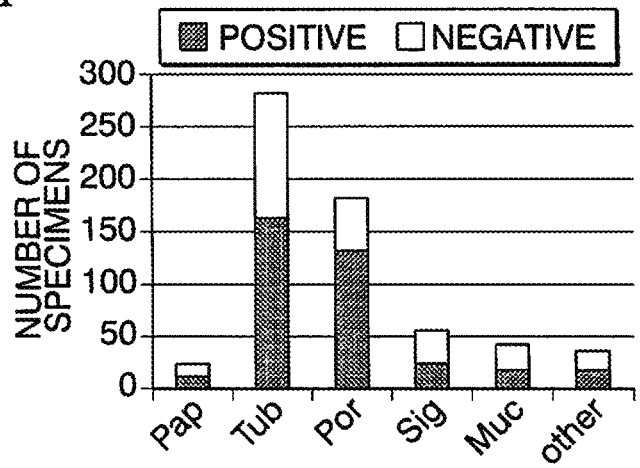
FIG. 1A is a view showing the number of LIX1L-positive specimens and LIX1L-negative specimens in various kinds of gastric cancer obtained from results in which gastric cancer clinical specimens are subjected to immunohistochemical staining, in Reference Example 1.

A LIX1L gene is a structural gene which exists in a chromosome 1q21.1 region of a human, and is a gene which is almost not expressed in a normal cell, but of which expression is accelerated in many tumor cells.

The term "tumor" used in the present specification means a malignant tumor (also referred to as cancer) that invades surrounding tissues in a cell population in which proliferation occurs which is not autonomously controlled by gene mutation, and which causes metastasis. The term "tumor" includes solid cancer and hematopoietic organ cancer including various kinds of sarcomas and carcinomas.

Here, examples of the solid cancer include a brain tumor, head and neck cancer, esophageal cancer, thyroid cancer, small cell lung cancer, non-small cell lung cancer, breast cancer, lung cancer, gastric cancer, gallbladder/bile duct cancer, liver cancer, hepatoma, pancreatic cancer, pancreatic cancer, colorectal cancer, colon cancer, rectal cancer, ovarian cancer, villus epithelial cancer, uterine cancer, cervical cancer, renal pelvis/ureter cancer, bladder cancer, prostate cancer, penile cancer, testicular cancer, embryonal cancer, virus tumor, skin cancer, malignant melanoma, neuroblastoma, osteosarcoma, Ewing's tumor, and soft tissue sarcoma. In contrast, examples of the hematopoietic organ cancer include acute leukemia, chronic lymphocytic leukemia, chronic myelogenous leukemia, genuine hypervolemic illness, malignant lymphoma, multiple myeloma, Hodgkin's lymphoma, and non-Hodgkin's lymphoma.

An amino acid sequence of a hLIX1L protein which is encoded by a LIX1L (hLIX1L) gene is represented by SEQ ID No: 1 and a base sequence of cDNA of the LIX1L gene is represented by SEQ ID No: 2 (accession number of EMBL: NM_153713.1).

The tumor cell is divided into a high LIX1L-expressing tumor cell in which a LIX1L gene is highly expressed and a low LIX1L-expressing tumor cell in which expression of a LIX1L gene is low (the expression level includes less than a detection limit value). The high LIX1L-expressing tumor cell is found in many tumors regardless of internal organs or the degree of differentiation and regardless of whether the cell is primary or metastatic. Particularly, even in all internal organs, the frequency of expression of a high LIX1L-expressing tumor cell is higher in undifferentiated tumor cells than in differentiated tumor cells. Actually, the inventors have examined patients with numerous solid tumors (gastric cancer, lung cancer, colorectal cancer, pancreatic cancer, prostate cancer, hepatoma, ovarian cancer, thyroid cancer, esophageal cancer, breast cancer, and renal cell cancer). As a result, about 20% to 60% of the tumors were LIX1L-positive tumors (refer to Reference Examples 1 and 2 to be described below).

In the present invention and the present specification, the term "high LIX1L-expressing tumor cell" means a tumor cell of which the expression level of a LIX1L gene is 8 or more times the expression level of a normal cell and the term "low-LIX1L expressing tumor cell" means a tumor cell other than the high LIX1L-expressing tumor cell. That is, whether a certain tumor cell is a high LIX1L-expressing tumor cell or a low LIX1L-expressing tumor cell can be determined by measuring the expression level of a LIX1L gene in this tumor cell. As the normal reference cell, a normal cell derived from the same tissue as that of a tumor cell which is an object for determining whether or not the tumor cell is a high LIX1L-expressing tumor cell may be used, or a normal cell derived from a different tissue from that of the tumor cell may be used. For example, it is possible to set a peripheral blood mononuclear cell collected and separated from a healthy person as a normal cell.

The expression levels of LIX1L genes may be compared with each other at the protein level. For example, it is possible to quantitatively detect the expression level of a LIX1L gene through a Western blotting method. Specifically, in a band which can be detected through the Western blotting method, by digitizing a signal of the band using densitometry, in a case where the signal detected from a tumor cell is 8 or more times the signal detected from a normal cell, it is possible to determine the signal as a "strong signal", and in a case where the signal detected from a tumor cell is less than 8 times the signal detected from a normal cell, it is possible to determine the signal as a "weak signal".

In addition, in a case where a cell lysate of a tumor cell is separated through electrophoresis, and is then transferred to a film on which a LIX1L protein is detected using an anti-LIX1L antibody, it is possible to determine that a tumor cell of which the signal intensity, which is obtained by measuring a signal obtained from the anti-LIX1L antibody that has been bonded to the LIX1L protein using densitometry, is 8 or more times the signal intensity similarly measured from a normal cell is a high LIX1L-expressing tumor cell, and to determine that a tumor cell of which the signal intensity thereof is less than 8 times the signal intensity similarly measured from the normal cell is a low LIX1L-expressing tumor cell.

The expression levels of LIX1L genes may be compared with each other at the mRNA level. For example, as will be shown in Reference Example 3 to be described below, it is possible to quantitatively detect the expression level of a LIX1L gene using a nucleic acid amplification reaction such as an RT-PCR method. Specifically, in a case where, for example, PCR is performed in which the whole length or a part of cDNA of a LIX1L gene is amplified by having cDNA, synthesized through a reverse transcription reaction from RNA extracted from a tumor cell, as a mold, it is possible to determine that a tumor cell, of which the amount of the obtained amplification product is 8 or more times the amplification product similarly obtained from a normal cell, is a high LIX1L-expressing tumor cell and to determine that a tumor cell other than that is a low LIX1L-expressing tumor cell.

It is possible to inhibit cell proliferation in a high LIX1L-expressing tumor cell by inhibiting the expression of a LIX1L gene with respect to the high LIX1L-expressing tumor cell. The effect of inhibiting the cell proliferation through the inhibition of the expression of a LIX1L gene tends to be larger as the expression level of the LIX1L gene of a tumor cell before inhibiting the expression becomes larger. In addition, in a case where the expression of a LIX1L gene with respect to a low LIX1L-expressing tumor cell is inhibited, it is impossible to detect such an effect of inhibiting the cell proliferation.

It is suggested that the LIX1L gene is involved in cell proliferation since the effect of inhibiting the cell proliferation can be obtained through inhibiting the LIX1L gene expression; LIX1L protein plays an important role in proliferation of a cell in which the LIX1L gene is highly expressed; and the LIX1L gene functions as a cancer gene. In the low LIX1L-expressing tumor cell, the role of the LIX1L protein is small and the proliferation is accelerated by other components, and therefore, it is inferred that no effect of inhibiting the cell proliferation may be observed even if the expression of the LIX1L gene is inhibited.

The function of a LIX1L gene has not been described in the related art, and whether the LIX1L gene is a cancer gene which is a cause of tumorigenesis of a cell or a gene in which expression is accelerated due to the tumorigenesis has not become clear. The fact that the cell proliferation of a high LIX1L-expressing tumor cell is inhibited through the inhibition of the expression of a LIX1L gene, that is, the fact that the LIX1L gene contributes to cell proliferation of a high LIX1L-expressing tumor cell, is knowledge first found by the present inventors.

The method for inhibiting the expression of a LIX1L gene is not particularly limited, and any well-known method in the related art may be used. In the present invention, it is preferable to inhibit the expression of a LIX1L gene through RNA interference since it is possible to apply the method to medical practice. The RNA interference can be performed by introducing small interfering RNA (siRNA), short hairpin RNA (shRNA), or micro RNA (miRNA) which has a double-stranded structure formed of a sense chain and an anti-sense chain in a partial region (RNAi target region) of cDNA of a LIX1L gene, into a high LIX1L-expressing tumor cell.

siRNA or the like may be directly introduced into a cell, or an RNAi-induced vector which can produce siRNA or the like in a cell may be introduced into the cell. The production of siRNA, shRNA, and an RNAi-induced vector, the introduction of siRNA, shRNA, and an RNAi-induced vector, and the like into a cell can be performed through a usual method. For example, it is possible to synthesize siRNA and shRNA through chemosynthesis. In addition, the production of the RNAi-induced vector can be performed through, for example, incorporating the chemically synthesized siRNA or shRNA into a commercially available siRNA expression vector.

Examples of the introduction of siRNA, shRNA, or RNAi-induced vector into a cell include introduction thereof using a transfection reagent (for example, Lipofectamine (registered trademark)); various viral vectors such as colloidal gold, retroviral vectors, lentiviral vectors, adenoviral vectors, adeno-associated virus vectors, and Sendai virus vectors; and nanoparticles prepared by combining various elements.

In addition, the RNAi-induced vector can be produced by inserting a base sequence in an RNAi target region into base sequences of various commercially available RNAi vectors.

It is possible to efficiently inhibit the expression of a LIX1L gene through RNA interference by, for example, making the RNAi target region in cDNA of the LIX1L gene a region consisting of a base sequence represented by SEQ ID No: 3 or 4. Specifically, shRNA, siRNA, or miRNA which includes a base sequence represented by SEQ ID No: 3 or 4, or a vector which produces the shRNA, the siRNA, or the miRNA in a cell is introduced into a cell which is a high LIX1L-expressing tumor cell. Examples of shRNA including a base sequence represented by SEQ ID No: 3 include a double-stranded acid consisting of a base sequence represented by a base sequence 5, and examples of shRNA including a base sequence represented by a SEQ ID No: 4 include a double-stranded acid consisting of a base sequence represented by a base sequence 6.

That is, examples of the method for inhibiting proliferation of a high LIX1L-expressing tumor cell include a method for inhibiting proliferation of a high LIX1L-expressing tumor cell which includes inhibiting the expression of a LIX1L gene through RNA interference and in which the inhibition of the expression of a LIX1L gene through RNA interference includes introduction of shRNA or siRNA which consists of a base sequence represented by SEQ ID No: 3 or 4, or a vector which produces the shRNA or the siRNA in a cell, into the cell.

In addition, shRNA, siRNA, or miRNA which includes a base sequence represented by SEQ ID No: 3 or 4, or a vector which produces the shRNA, the siRNA, or the miRNA in a cell can be formulated through appropriate chemical modification or the like similarly to the tumor cell proliferation-inhibiting peptide as an embodiment of the present invention.

The effect of inhibiting the proliferation of a high LIX1L-expressing tumor cell can be obtained through inhibiting the function of a LIX1L gene as well as through inhibiting the expression of a LIX1L gene. Examples of the method for inhibiting the function of a LIX1L gene include methods of excessively introducing an inactive mutant of a LIX1L protein, a partial protein or a peptide in which a partial region which is required for function or activation is deficient, into a cell.

Among these, a method for introducing a peptide (hereinafter, referred to as a "tumor cell proliferation-inhibiting peptide as one embodiment of the present invention") or a partial protein, which is homologous to a partial region involved in signal transmission in a LIX1L protein and in which a functional domain for responding to the transmitted signal is deficient, into a cell is preferable. The tumor cell proliferation-inhibiting peptide competes with an endogenous LIX1L protein within a cell which is a high LIX1L-expressing tumor cell. Therefore, it is possible to inhibit the cell proliferation of the high LIX1L-expressing tumor cell similarly to a case in which the expression of the LIX1L protein is inhibited.

Examples of the tumor cell proliferation-inhibiting peptide as one embodiment of the present invention include a peptide including an amino acid sequence (hereinafter, in some cases, simply referred to as a "phosphorylation region-partial sequence") which is homologous to a partial region containing a tyrosine residue, a serine residue, or a threonine residue which is phosphorylated through transmission of a specific signal in a LIX1L protein. This is because it is considered that, in many cells, the phosphorylation of a protein plays an important role in signal transmission of the cell proliferation or the like, and the LIX1L protein is also involved in the cell proliferation signal through the phosphorylation of the tyrosine residue or the like.

The "tumor cell proliferation-inhibiting peptide" in the present specification and the claims means a peptide of which the C-terminal is amidated. That is, the tumor cell proliferation-inhibiting peptide has become —COONH$_2$ due to a carboxyl group at the C-terminal being amidated.

Examples of the tumor cell proliferation-inhibiting peptide as one embodiment of the present invention include a polypeptide (hereinafter, referred to as a "Y136-containing peptide") containing the 136th tyrosine (Y136) from the N-terminal of a LIX1L protein. It is possible to inhibit the cell proliferation of a high LIX1L-expressing tumor cell by introducing the Y136-containing peptide into a cell. Specific examples of the Y136-containing peptide include a polypeptide including a partial sequence (Y136-containing partial sequence), which is a partial sequence of an amino acid sequence represented by SEQ ID No: 1, as a phosphorylation region-partial sequence.

The tumor cell proliferation-inhibiting peptide as one embodiment of the present invention can be synthesized through, for example, chemical synthesis.

The position of Y136 in a Y136-containing partial sequence is not particularly limited and may be in the vicinity of the N-terminal or the C-terminal of the Y136-containing partial sequence. However, the position thereof is preferably in the vicinity of the center of the Y136-containing partial sequence. In addition, the length (number of amino acids) of the Y136-containing partial sequence may be a length to the extent that the polypeptide consisting of this Y136-containing partial sequence can be distinguished from other polypeptides, and the length thereof is preferably greater than or equal to 8 amino acids, more preferably greater than or equal to 10 amino acids, and still more preferably greater than or equal to 11 amino acids. In contrast, in a polypeptide of which the length is too long, the cell membrane permeability tends to become low and there is a concern that the polypeptide of which the length is too long exhibits antigenicity when being administered into a living body. For this reason, the length of the Y136-containing partial sequence is preferably less than or equal to 35 amino acids and more preferably less than or equal to 30 amino acids.

That is, the length of the Y136-containing partial sequence is preferably 8 amino acids to 35 amino acids, more preferably 10 amino acids to 35 amino acids, and still more preferably 11 amino acids to 30 amino acids.

The "vicinity of the N-terminal" means a position within 5 amino acids from the N-terminal and the "vicinity of the C-terminal" means a position within 5 amino acids from the C-terminal. The "vicinity of the center" means a position within 10 amino acids from the position of the center of the Y136-containing partial sequence.

Specifically, as the Y136-containing partial sequence, a partial amino acid sequence is preferable containing 8 amino acids having the 136th tyrosine starting from the 130th proline from the N-terminal, and a partial amino acid sequence is more preferable containing 11 amino acids having the 136th tyrosine starting from the 130th proline from the N-terminal.

The tumor cell proliferation-inhibiting peptide as one embodiment of the present invention may be a polypeptide consisting of only a phosphorylation region-partial sequence such as the Y136-containing partial sequence, but more preferably has a site having cell membrane permeability. With the tumor cell proliferation-inhibiting peptide as one embodiment of the present invention having a site having cell membrane permeability, it is possible to more efficiently introduce the tumor cell proliferation-inhibiting peptide into a cell which is a high LIX1L-expressing tumor cell. The site having cell membrane permeability may be a site consisting of a polypeptide or a site containing components other than the polypeptide, for example, sugars, nucleic acids, or low-molecular compound. In addition, this site may be a polypeptide consisting of only a natural type amino acid or a polypeptide containing a modified amino acid. Preferred examples of the site having cell membrane permeability consisting of a polypeptide include membrane-permeable peptides such as a Tat peptide derived from a Trans-Activator of Transcription Protein (TAT) of HIV-1, oligoarginine; Penetratin derived from an Antennapedia protein of drosophila; and transportan, which is a chimeric peptide of a neuropeptide galanin and bee venom mastoparan.

In a case where the tumor cell proliferation-inhibiting peptide as one embodiment of the present invention has a site, such as a membrane-permeable peptide which has cell membrane permeability, the polypeptide which consists of a phosphorylation region-partial sequence and the site which has cell membrane permeability may be directly bonded to each other, or may be indirectly bonded to each other through various linkers.

In addition, in the tumor cell proliferation-inhibiting peptide, the polypeptide consisting of a phosphorylation region-partial sequence such as a Y136-containing partial sequence may be on an N-terminal side or the site having cell membrane permeability may be on the N-terminal side.

The linkers are not particularly limited as long as the linkers can connect polypeptides together or a polypeptide to another compound. However, a comparatively smaller molecule is preferable in view of cell membrane permeability, a risk of antigenicity, or the like. For example, in a case where the site having cell membrane permeability is a membrane-permeable peptide, a linker formed of 1 to 5 amino acids (which may contain a modified amino acid such as $\epsilon$-aminocaproic acid) is preferable as the linker. 1 amino acid of $\epsilon$-aminocaproic acid is more preferable as the linker.

The tumor cell proliferation-inhibiting peptide as one embodiment of the present invention may have another functional site other than or in addition to the site having cell membrane permeability. The other functional site is not particularly limited as long as the site does not impair the function of inhibiting the proliferation using a polypeptide consisting of a phosphorylation region-partial sequence. Examples of the other functional site include a tag peptide, such as a His tag, a Myc tag, a tag peptide, and a Flag tag, which is widely used in refinement of a protein.

In order to introduce the tumor cell proliferation-inhibiting peptide as one embodiment of the present invention into a cell, the tumor cell proliferation-inhibiting peptide itself may be introduced into a cell, or a vector which can produce the tumor cell proliferation-inhibiting peptide in a cell may be introduced into a high LIX1L-expressing tumor cell. The tumor cell proliferation-inhibiting peptide according to the present invention or the vector for producing the tumor cell proliferation-inhibiting peptide can be introduced into a high LIX1L-expressing tumor cell through a usual method. Examples of the method for introducing a peptide into a high LIX1L-expressing tumor cell include a transfection reagent (for example, Lipofectamine (registered trademark)); various viral vectors such as colloidal gold, retroviral vectors, lentiviral vectors, adenoviral vectors, adeno-associated virus vectors, and Sendai virus vectors; and nanoparticles prepared by combining various elements. Particularly when the tumor cell proliferation-inhibiting peptide according to the present invention has a site having cell membrane permeability, it is possible to efficiently introduce the polypeptide into a cell by simply bringing the polypeptide into contact with a high LIX1L-expressing tumor cell.

That is, examples of the method for inhibiting proliferation of a high LIX1L-expressing tumor cell include a method for inhibiting proliferation of a high LIX1L-expressing tumor cell which includes introduction of a tumor cell proliferation-inhibiting peptide tumor cell proliferation-inhibiting peptide into a high LIX1L-expressing tumor cell. In the method, the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and the polypeptide and the site having cell membrane permeability are directly or indirectly bonded to each other.

The reason why the proliferation of a high LIX1L-expressing tumor cell is inhibited by introducing a Y136-containing peptide into a cell is not obvious. However, since Y136 in a LIX1L protein is a tyrosine residue having a higher probability to be phosphorylated, tyrosine corresponding to Y136 of the LIX1L protein in the peptide is phosphorylated through competition with Y136 of the LIX1L protein, and therefore, a proliferation signal is disconnected based on the phosphorylation of Y136 in the LIX1L protein. As a result, the cell proliferation function of a LIX1L gene is inhibited. Therefore, it is inferred that the same effect as that in a case where the expression of the LIX1L gene is inhibited is obtained.

The tumor cell proliferation-inhibiting peptide according to the present invention has an effect of inhibiting the proliferation of a high LIX1L-expressing tumor cell, and therefore, is useful as a pharmaceutical composition including an anti-tumor agent. Since the tumor cell proliferation-inhibiting peptide according to the present invention is a smaller molecule compared to a glycoprotein, which is a macromolecule, the tumor cell proliferation-inhibiting peptide has advantages in that an antibody is hardly produced when the tumor cell proliferation-inhibiting peptide is administered into a human body; it is possible to chemically massively produce the tumor cell proliferation-inhibiting peptide due to its simple structure; and it is easy to manage the quality of the tumor cell proliferation-inhibiting peptide in a production process.

Particularly, the tumor cell proliferation-inhibiting peptide according to the present invention has a wide spectrum of an anti-tumor effect and cytotoxicity to a normal cell is extremely low. Therefore, the tumor cell proliferation-inhibiting peptide can become an excellent anti-tumor agent. This is because the tumor cell proliferation-inhibiting peptide according to the present invention is a new peptide compound having a LIX1L protein, which is specifically expressed in a tumor cell, as a direct target, in many tumor cells (for example, a brain tumor, head and neck cancer, esophageal cancer, thyroid cancer, small cell lung cancer, non-small cell lung cancer, breast cancer, lung cancer, gastric cancer, gallbladder/bile duct cancer, liver cancer, hepatoma, pancreatic cancer, pancreatic cancer, colorectal cancer, colon cancer, rectal cancer, ovarian cancer, villus epithelial cancer, uterine cancer, cervical cancer, renal pelvis/ureter cancer, bladder cancer, prostate cancer, penile cancer, testicular cancer, embryonal cancer, a virus tumor, skin cancer, malignant melanoma, neuroblastoma, osteosarcoma, Ewing's tumor, and soft tissue sarcoma, acute leukemia, chronic lymphocytic leukemia, chronic myelogenous leukemia, genuine hypervolemic illness, malignant lymphoma, multiple myeloma, Hodgkin's lymphoma, and non-Hodgkin's lymphoma; preferably gastric cancer, lung cancer, colorectal cancer, pancreatic cancer, prostate cancer, hepatoma, ovarian cancer, thyroid cancer, esophageal cancer, breast cancer, and renal cell cancer; and more preferably gastric cancer, lung cancer, colorectal cancer, pancreatic cancer, ovarian cancer, and renal cell cancer), and it is possible to expect that the tumor cell proliferation-inhibiting peptide does not particularly affect a cell in which a LIX1L protein is not expressed or the expression level is small.

The pharmaceutical composition or the anti-tumor agent according to the present invention may contain a pharmaceutically acceptable carrier or diluent.

Here, the "pharmaceutically acceptable carrier or diluent" means an excipient (for example, fat, beeswax, polyols of semi-solid and a liquid, or natural or hardened oil); water (for example, distilled water, in particular, distilled water for injection), physiological saline, alcohol (for example, ethanol), glycerol, a polyol, an aqueous glucose solution, mannitol, vegetable oil, and the like; additives (for example, an extending agent, a disintegrator, a bonding agent, a lubricant, a wetting agent, a stabilizer, an emulsifier, a dispersant, a preservative, a sweetener, a colorant, a flavoring or a fragrance, a thickening agent, a diluent, a buffer substance, a solvent or a solubilizing agent, a drug for achieving a storage effect, a salt for changing osmotic pressure, a coating agent, or an antioxidant), and the like.

Various forms of agents relating to the pharmaceutical composition or the anti-tumor agent of the present invention can be selected, and examples thereof include oral formulations such as a tablet, a capsule, a powdered agent, a granule, or a liquid; sterilized liquid-like parenteral formulations such as a solution or a suspension; a suppository; and an ointment.

Examples of a solvent or a diluent which is appropriate when being parentally administered in a form of intramuscular injection, intravenous injection, or subcutaneous injection include distilled water for injection, a lidocaine hydrochloride aqueous solution (for intramuscular injection), physiological saline, an aqueous glucose solution, ethanol, polyethylene glycol, propylene glycol, a liquid for intravenous injection (for example, an aqueous solution such as citric acid and sodium citrate), or an electrolyte solution (for intravenous drip infusion and intravenous injection), or a mixed solution thereof.

These injections can take a form in which injections having been dissolved in advance, or injections in a state of powder or injections to which an appropriate carrier (additive) has been added are dissolved when in use. These injection solutions can contain, for example, an active ingredient of 10% by weight to 90% by weight based on the weight of the entire agent.

These agents can be easily produced by those skilled in the art in accordance with a usual method or a conventional technique. For example, in a case where an agent containing the tumor cell proliferation-inhibiting peptide of the present invention is an injection, it is possible to produce the injection by mixing an adequate amount of the tumor cell proliferation-inhibiting peptide of the present invention with an adequate amount of 0.9% physiological saline and filling a vial for injection with this mixture.

The tumor cell proliferation-inhibiting peptide of the present invention can be used in combination with other agents which are useful for treating various kinds of cancer, or in combination with radiation therapy.

The present invention includes a therapy for a tumor (that is, cancer) which includes administering a therapeutically effective amount of a tumor cell proliferation-inhibiting peptide into a target into which administration thereof is required.

The "target into which administration thereof is required" in the present invention means a patient who has a tumor cell highly expressing LIX1L.

The term "treatment of a tumor (cancer)" in the present invention means inhibition of proliferation of a tumor cell through administering an agent containing the tumor cell proliferation-inhibiting peptide of the present invention into a patient for whom the administration is required. Preferably, in the treatment, it is possible to retreat a tumor cell, that is, to reduce the size of a tumor which can be measured. More preferably, in the treatment, the tumor cell is completely eliminated.

In addition, the "treatment" in the present invention also includes preventive administration.

In the method according to the present invention, the unit of preferred treatment may be changed depending on the form of administering a tumor cell proliferation-inhibiting peptide of the present invention, the type of a tumor cell proliferation-inhibiting peptide of the present invention to be used, and the dosage form of a tumor cell proliferation-inhibiting peptide of the present invention to be used; the type of, the administration form of, and the dosage form of other anti-cancer agents to be used in combination therewith; the condition of a tumor cell (cancer cell) to be treated and the condition of a patient; and the like. Those skilled in the art can determine optimum treatment under predetermined conditions based on a conventional treatment determination unit and/or in consideration of the present specification.

Specifically, in the method according to the present invention, the treatment unit of the tumor cell proliferation-inhibiting peptide of the present invention can change depending on the type of tumor cell proliferation-inhibiting peptide to be used, the type of composition blended, the application frequency, a specific site to be treated, the severity of illness, the age of a patient, the diagnosis by a doctor, the type of tumor (cancer), and the like. For example, as a certain yardstick, the dosage per person per day for adults can be set to be within a range of, for example, 10 mg/kg to 200 mg/kg per day, in a case of parenteral administration, preferably in a case of intravenous administration, and still more preferably in a case of intravenous drip infusion. Here, in the case of intravenous drip infusion, administration may be continuously performed for, for example, 1 hour to 48 hours. The number of times of administration varies depending on the administration method and the symptoms, but examples thereof include once per day to 5 times per day. In addition, it is possible to use an intermittent administration method such as alternate day administration or administration once every three days. The repose period of treatment in the case of parenteral administration is, for example, 0 weeks to 4 weeks.

In addition, the tumor cell proliferation-inhibiting peptide according to the present invention can specifically inhibit the function of a LIX1L protein in a cell, and therefore, is useful as a tool for transmitting a signal in a cell, and particularly for clarifying the function of a LIX1L gene in a cell proliferation signal.

Examples of other aspects of the present invention include:

a method for inhibiting proliferation of a high LIX1L-expressing tumor cell, in which the high LIX1L-expressing tumor cell is a cell in which the expression level of a LIX1L gene in at least one cancer cell selected from the group consisting of gastric cancer, lung cancer, colorectal cancer, pancreatic cancer, prostate cancer, hepatoma, ovarian cancer, thyroid cancer, esophageal cancer, breast cancer, and renal cell cancer is 8 or more times the expression level of a normal cell, in which the proliferation inhibition method includes inhibiting the expression of a LIX1L gene through RNA interference, and in which the inhibition of the expression of a LIX1L gene through RNA interference includes introduction of shRNA or siRNA which consists of a base sequence represented by SEQ ID No: 3 or 4, or a vector which produces the shRNA or the siRNA in a cell, into the cell.

Examples of other aspects of the present invention include:

a tumor cell proliferation-inhibiting peptide, in which the tumor cell proliferation-inhibiting peptide includes a polypeptide consisting of a partial sequence with 8 amino acids which is an amino acid sequence represented by SEQ ID No: 1 and contains the 136th tyrosine starting from the 130th proline, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

a pharmaceutical composition containing the tumor cell proliferation-inhibiting peptide and a pharmaceutically acceptable carrier or diluent.

Examples of other aspects of the present invention include:

a pharmaceutical composition containing the tumor cell proliferation-inhibiting peptide and a pharmaceutically acceptable carrier or diluent, in which the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

a tumor cell proliferation-inhibiting peptide for inhibiting proliferation of a high LIX1L-expressing tumor cell.

Examples of other aspects of the present invention include:

a tumor cell proliferation-inhibiting peptide for inhibiting proliferation of a high LIX1L-expressing tumor cell, in which the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

use of a tumor cell proliferation-inhibiting peptide for producing a medicine for inhibiting proliferation of a high LIX1L-expressing tumor cell.

Examples of other aspects of the present invention include:

the use of a tumor cell proliferation-inhibiting peptide for producing a medicine for inhibiting proliferation of a high LIX1L-expressing tumor cell, in which the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, in which the polypeptide and the site having cell membrane permeability are directly or indirectly bonded to each other.

Examples of other aspects of the present invention include:

a method for inhibiting proliferation of a high LIX1L-expressing tumor cell, in which the proliferation inhibition method includes introducing a tumor cell proliferation-inhibiting peptide into a high LIX1L-expressing tumor cell, in which the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

a method for inhibiting proliferation of a high LIXIL-expressing tumor cell, in which the proliferation inhibition method includes introducing a tumor cell proliferation-inhibiting peptide into a high LIX1L-expressing tumor cell, in which the high LIX1L-expressing tumor cell is a cell in which the expression level of a LIX1L gene in at least one cancer cell selected from the group consisting of gastric cancer, lung cancer, colorectal cancer, pancreatic cancer, prostate cancer, hepatoma, ovarian cancer, thyroid cancer, esophageal cancer, breast cancer, and renal cell cancer is 8 or more times the expression level of a normal cell, in which the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

a method for inhibiting proliferation of a high LIX1L-expressing tumor cell, in which the proliferation inhibition method includes introducing a tumor cell proliferation-inhibiting peptide into a high LIX1L-expressing tumor cell, in which the high LIX1L-expressing tumor cell is a cell in which the expression level of a LIX1L gene in at least one cancer cell selected from the group consisting of gastric cancer, lung cancer, colorectal cancer, pancreatic cancer, prostate cancer, hepatoma, ovarian cancer, thyroid cancer, esophageal cancer, breast cancer, and renal cell cancer is 8 or more times the expression level of a normal cell, in which the tumor cell proliferation-inhibiting peptide includes a polypeptide consisting of a partial sequence with 8 amino acids which is an amino acid sequence represented by SEQ ID No: 1 and contains the 136th tyrosine starting from the 130th proline, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

a method for inhibiting proliferation of a high LIX1L-expressing tumor cell, wherein the proliferation inhibition method includes administering a therapeutically effective amount of a tumor cell proliferation-inhibiting peptide into a target into which administration thereof is required.

in which the tumor cell proliferation-inhibiting peptide includes a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and in which the polypeptide and the site having cell membrane permeability are directly or indirectly bonded to each other.

Examples of other aspects of the present invention include:

a method for inhibiting proliferation of a high LIX1L-expressing tumor cell, in which the method is a method for inhibiting phosphorylation of tyrosine of a LIX1L protein, and in which the method for inhibiting phosphorylation includes administering a therapeutically effective amount of a tyrosine kinase inhibitor into a target into which administration thereof is required.

Examples of other aspects of the present invention include:

a method for inhibiting proliferation of a high LIX1L-expressing tumor cell, in which the method is a method for inhibiting phosphorylation of tyrosine of a LIX1L protein, and in which the method for inhibiting phosphorylation includes administering a therapeutically effective amount of a tyrosine kinase inhibitor into a target into which administration thereof is required, in which the tyrosine is the 136th tyrosine of the LIX1L protein consisting of an amino acid sequence represented by SEQ ID No: 1, and in which the tyrosine kinase inhibitor is a tumor cell proliferation-inhibiting peptide including a polypeptide consisting of a partial sequence with 8 amino acids to 35 amino acids which is an amino acid sequence represented by SEQ ID No: 1 and contains the 136th tyrosine, and a site which consists of an amino acid sequence represented by SEQ ID No: 7 and has cell membrane permeability, and the polypeptide and the site having cell membrane permeability are directly or indirectly bonded to each other.

EXAMPLES

Next, the present invention will be described in more detail while showing examples, but is not limited to the following examples.

Reference Example 1

The expression levels of LIX1L genes of gastric cancer clinical specimens collected from patients with gastric cancer were quantitatively detected through immunohistochemical staining for comparison. These gastric cancer clinical specimens were classified into papillary adenocarcinoma (Pap), tubular adenocarcinoma (Tub), poorly differentiated adenocarcinoma (Por), signet ring cell carcinoma (Sig), mucinous carcinoma (Muc), and others. The tubular adenocarcinoma was further classified into a well-differentiated type (Tub 1) and a moderately-differentiated type (Tub2), and the poorly differentiated adenocarcinoma was further classified into a solid type (Por1) and a nonsolid type (Por2). Among these, the papillary adenocarcinoma and the tubular adenocarcinoma were differentiated tumor cells and the others were undifferentiated tumor cells.

In general, a normal cell and a tumor cell coexist in one tumor tissue. Therefore, a specimen of which the proportion of a high LIX1L-expressing tumor cell included in each of the gastric cancer clinical specimens was high was determined as a LIX1L-positive tumor and a specimen of which the proportion of a high LIX1L-expressing tumor cell included in each of the gastric cancer clinical specimens was low was determined as a LIX1L-negative tumor.

Specifically, a cell in each of the gastric cancer clinical specimens was subjected to immunohistochemical staining using an anti-LIX1L rabbit polyclonal antibody (manufactured by Abnova Corporation) as a primary antibody and a peroxidase-labeled goat anti-rabbit IgG polyclonal antibody (product name: Histofine Simple Stain MAX-PO (MULTI), manufactured by Nichirei Corporation) as a secondary antibody.

Three identical enlarged visual fields randomly selected in the gastric cancer clinical specimens were microscopically examined, a signal detected from a tumor site and a signal detected from a cell in an adjacent normal tissue were compared with each other; a cell of the tumor site in which a stronger signal than that detected from the cell in the adjacent normal tissue was set as a LIX1L-positive tumor cell and a cell in which no signal was detected was set as a LIX1L-negative cell; and the number of LIX1L-positive tumor cells and the number of LIX1L-negative tumor cells were measured.

Among all of the measured cells, each of the gastric cancer clinical specimens were determined such that a gastric cancer clinical specimen of which the proportion of the LIX1L-positive cells in the tumor cells was 30% to 100% was determined as a LIX1L-positive specimen (+), a gastric cancer clinical specimen of which the proportion of the LIX1L-positive cells in the tumor cells was 10% to 30% was determined as a LIX1L weakly positive (+/−), and a gastric cancer clinical specimen of which the proportion of the LIX1L-positive cells in the tumor cells was 0% to 10% was determined as a LIX1L-negative (−).

Figure 1B:
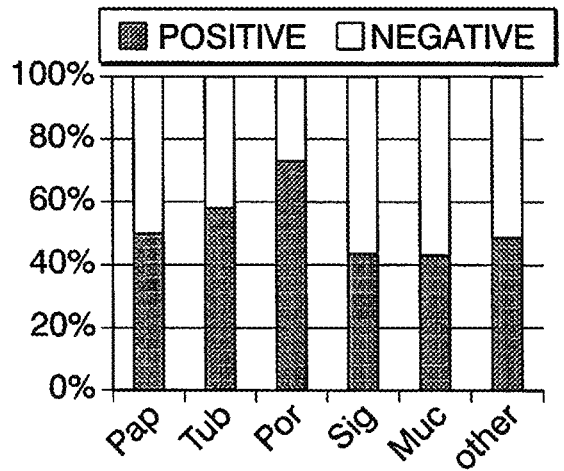
FIG. 1B is a view showing results in which the frequency of LIX1L-positive tumors in various kinds of gastric cancer is calculated, in Reference Example 1.
Figure 1C:
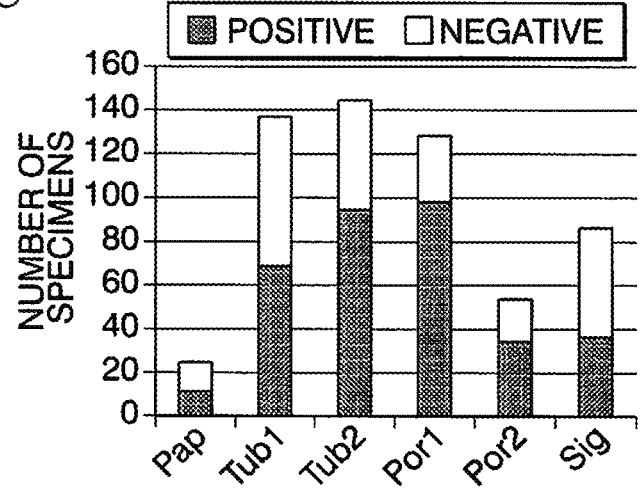
FIG. 1C is a view showing the number of LIX1L-positive specimens and LIX1L-negative specimens in various kinds of gastric cancer obtained from results in which gastric cancer clinical specimens are subjected to immunohistochemical staining, in Reference Example 1.
Figure 1D:
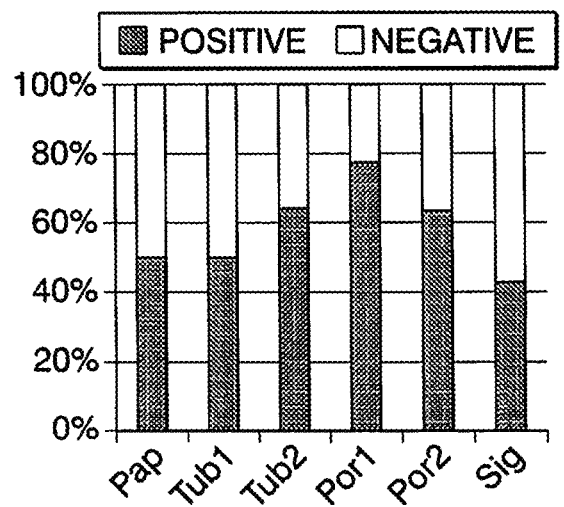
FIG. 1D is a view showing results in which the frequency of LIX1L-positive tumors in various kinds of gastric cancer is calculated, in Reference Example 1.
Figure 1E:
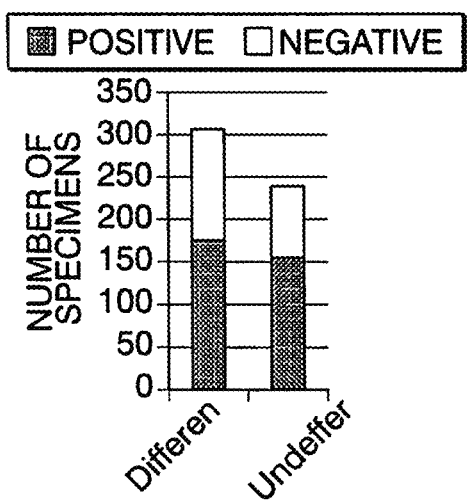
FIG. 1E is a view showing the number of LIX1L-positive specimens and LIX1L-negative specimens for each differentiated tumor and undifferentiated tumor, in all of the gastric cancer clinical specimens in Reference Example 1.
Figure 1F:
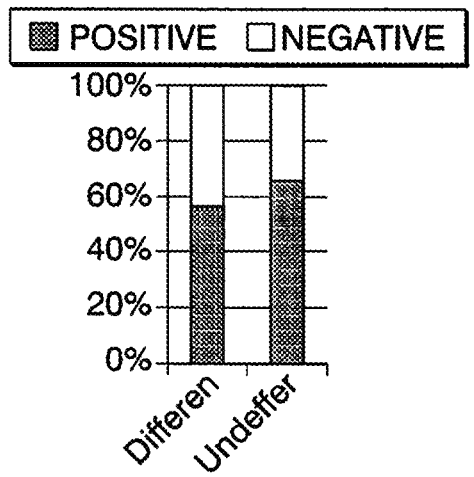
FIG. 1F is a view showing results in which the frequency of LIX1L-positive tumors in the differentiated tumor and the undifferentiated tumor is calculated, in Reference Example 1.

The number of the LIX1L-positive specimens and the LIX1L-negative specimens and the proportions thereof obtained from the results of the immunohistochemical staining are shown in FIGS. 1A to 1F. FIG. 1A shows the number of LIX1L-positive specimens and LIX1L-negative specimens for each papillary adenocarcinoma, tubular adenocarcinoma, poorly differentiated adenocarcinoma, signet ring cell carcinoma, mucinous carcinoma, and other kinds of cancer ("other" in the drawing), and FIG. 1B shows results in which the frequency of LIX1L-positive tumors in various kinds of gastric cancer is calculated from the results in FIG. 1A. FIG. 1C shows the number of LIX1L-positive specimens and LIX1L-negative specimens for each papillary adenocarcinoma, well-differentiated type tubular adenocarcinoma, moderately-differentiated type tubular adenocarcinoma, solid type poorly differentiated adenocarcinoma, non-solid type differentiated adenocarcinoma, and signet ring cell carcinoma, FIG. 1D shows results in which the frequency of LIX1L-positive tumors in various kinds of gastric cancer is calculated from the results in FIG. 1C. FIG. 1E shows the number of LIX1L-positive specimens and LIX1L-negative specimens for each differentiated tumor ("Differen" in the drawing) and undifferentiated tumor ("Undiffer" in the drawing) in all of the gastric cancer clinical specimens, and FIG. 1F shows results in which the frequency of LIX1L-positive tumors in the differentiated tumor and the undifferentiated tumor is calculated from the results in FIG. 1E. The result was that LIX1L-positive tumors were detected at a frequency of at least 40% or more in all kinds of gastric cancer.

Reference Example 2

Similarly to Reference Example 1, immunohistochemical staining was performed on clinical specimens collected from patients with solid tumors (lung cancer, colorectal cancer, pancreatic cancer, prostate cancer, hepatoma, ovarian cancer, thyroid cancer, esophageal cancer, breast cancer, and renal cell cancer) other than gastric cancer, and the number of LIX1L-positive specimens and LIX1L-negative specimens in various kinds of cancer and the proportion thereof were obtained.

Figure 2A:
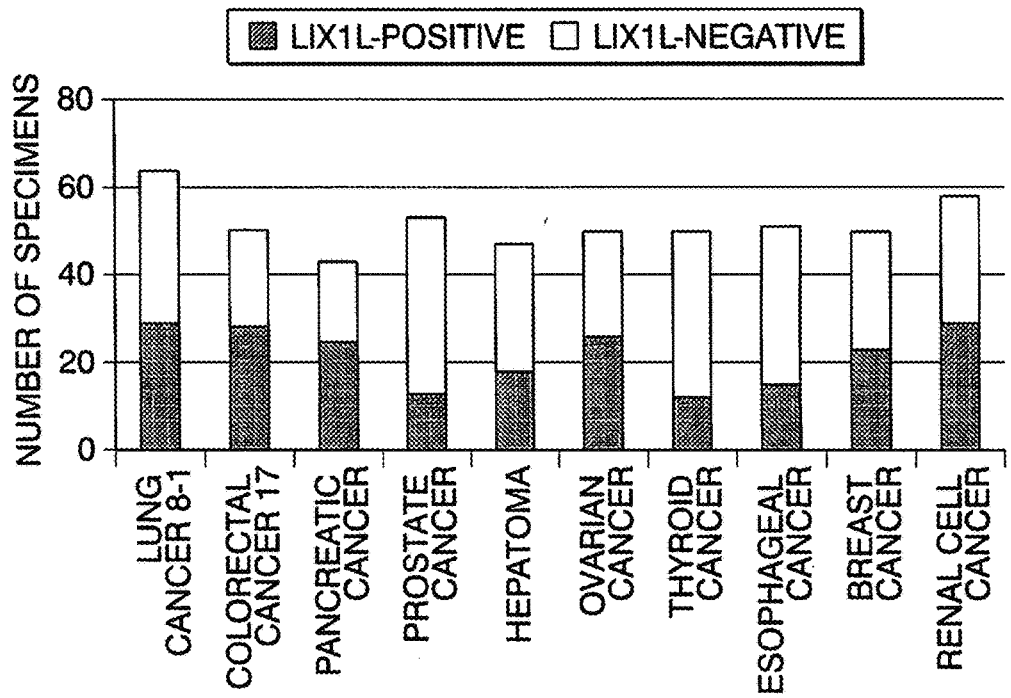
FIG. 2A is a view showing the number of LIX1L-positive specimens and LIX1L-negative specimens in various kinds of cancer obtained from results in which various kinds of gastric cancer clinical specimens are subjected to immunohistochemical staining, in Reference Example 2.
Figure 2B:
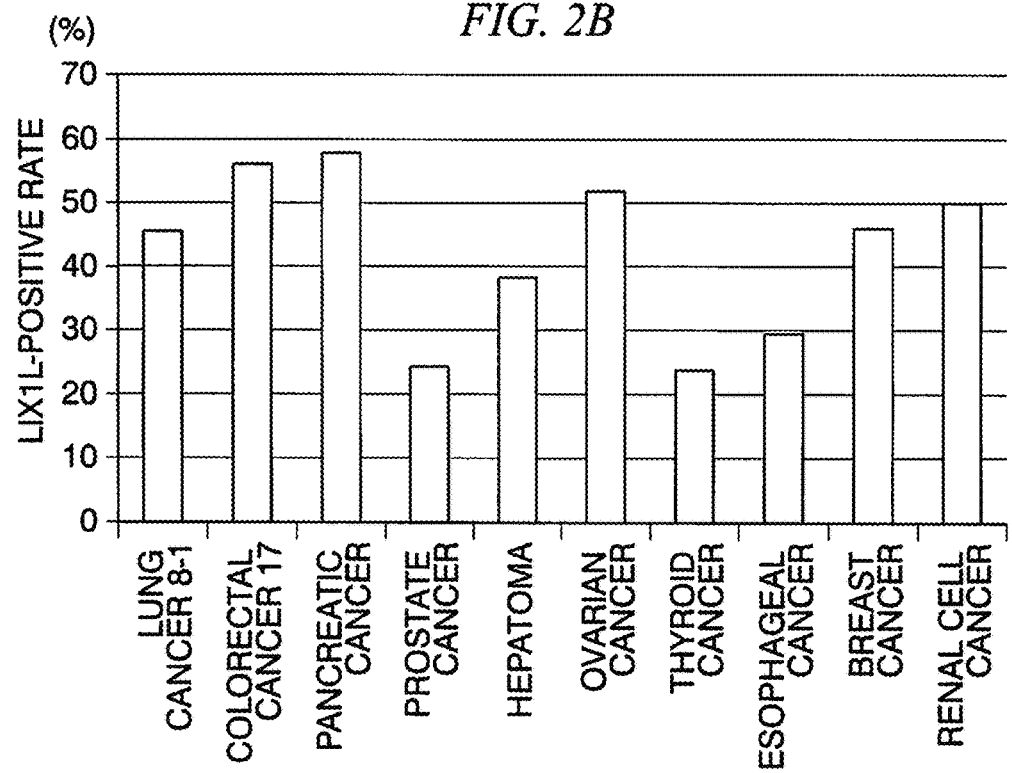
FIG. 2B is a view showing results in which the frequency of LIX1L-positive tumors in each cancer is calculated, in Reference Example 2.

The number of LIX1L-positive specimens and LIX1L-negative specimens in various kinds of cancer obtained from the results of the immunohistochemical staining is shown in FIG. 2A, and results in which the frequency of LIX1L-positive tumors in various kinds of cancer is calculated from the results thereof is shown in FIG. 2B. In all kinds of cancer, about 20% to 60% of the tumors were LIX1L-positive tumors.

Reference Example 3

The expression levels of LIX1L genes in gastric cancer cell strains were quantitatively measured from both a protein level and an mRNA level through a Western blotting method and an RT-PCR method for comparison.

Two kinds of strains including KATO-III strains and OCUM-1 strains were used as gastric cancer cell strains. Both cell strains are undifferentiated tumors. Each of the KATO-III strains was analyzed after being cultured for 10 days to 14 days in a culture solution in which 10 vol. % of fetal calf serum (FCS) with respect to an RPMI 1640 culture medium was added to the RPMI 1640 culture medium. Each of the OCUM-1 strains was analyzed after being cultured for 10 days to 14 days in a culture solution in which 10 vol. % of FCS with respect to a DMEM culture medium was added to the DMEM culture medium. Specifically, regarding each analysis, first, the cultured cells were collected, and Western blotting was used for some of the cultured cells and RT-PCR was used for the rest of the cultured cells.

Similarly, the expression level of a LIX1L gene of a peripheral blood mononuclear cell (normal peripheral blood mononuclear cell) collected from a healthy person and isolated from blood was examined as a comparison. The normal peripheral blood mononuclear cell was isolated as follows. First, 5 mL of phosphate-buffered saline (PBS) was added to 5 mL of a whole blood sample for dilution. Then, the total amount of the diluent was carefully stacked on 20 mL of Ficoll (registered trademark) (manufactured by GE Healthcare Ltd.) fractionated into a centrifuge tube in advance, and centrifugal separation treatment (under the conditions of maximum acceleration/natural deceleration (no brake)) was performed for 20 minutes at 22° C. and 2200 rpm.

After the completion of the centrifugal separation treatment, the peripheral blood mononuclear cell (hereinafter, in some cases, referred to as PBMC) layer was carefully taken out of the centrifuge tube so as not to disrupt the separated layer and was collected into a new tube with a 15 mL capacity. PBS was added to the collected PBMC layer, centrifugal separation treatment (under the conditions of maximum acceleration/maximum deceleration) was performed for 10 minutes at 4° C. and 1500 rpm, and a washing operation for removing a supernatant was performed twice. The washed resultant obtained by adding an appropriate amount of PBS to the PBMC layer for suspension was set as a normal peripheral blood mononuclear cell specimen. The normal peripheral blood mononuclear cell specimen was used in an experiment after the number of cells was counted using a hemocytometer and the number of viable cells was examined through Trypan blue staining.

In the RT-PCR, first, RNA was extracted and purified from the collected cells using RNeasy Mini Kit (manufactured by QIAGEN). The concentration of total RNA was measured using a spectrophotometer. A reverse transcription reaction was performed using First Strand cDNA Synthesis Kit (manufactured by Roche Life Science) for RT-PCR (AMV), for synthesizing cDNA, in 20 μL of a reaction solution containing 1 μg of total RNA and a random primer for 10 minutes at 25° C., subsequently for 45 minutes at 42° C., and then for 2 minutes at 95° C., to deactivate reverse transcriptase. In all PCRs, TaqMan (registered trademark) polymerase (manufactured by Life Technologies Ltd.) was used. PCR was performed using a DNA thermal cycler (model PTC 200, manufactured by MJ Research, Inc.) in 20 µL of a reaction solution using a primer set consisting of a forward primer consisting of a base sequence represented by SEQ ID No: 8 and a base sequence represented by SEQ ID No: 9, having the synthesized cDNA as a mold. This primer set is a primer set designed to amplify fragments of cDNA of LIX1L genes of 218 bp. Furthermore, PCR was performed in the same manner except that a primer set consisting of a forward primer consisting of a base sequence represented by SEQ ID No: 10 and a base sequence represented by SEQ ID No: 11 and is designed to amplify fragments of cDNA of GAPDH genes of 253 bp was used instead of the primer set as a control. 28 cycles were performed under the reaction conditions of 30 seconds at 96° C., 30 seconds at 56° C., and 30 seconds at 72° C. being one cycle. Amplified products obtained by amplifying both the LIX1L and the GAPDH were applied to 1.5% agarose gel to perform electrophoresis, and a separated nucleic acid was subjected to ethidium bromide staining. The signal intensity of a band of LIX1L in an ethidium bromide staining image was measured using densitometry and a relative value of the signal intensity was calculated. In addition, in all quantitative PCR reactions, SYBR (registered trademark) Green I was used. Quantitative determination was performed in 25 µL of a reaction solution containing the synthesized cDNA and a LIX1L primer using an ABI PRISM 7700 Sequence detector (manufactured by Perkin-Elmer/Applied Biosystems). The expression of GAPDH was also confirmed as an internal standard. 45 cycles were performed under the reaction conditions of 5 seconds at 95° C. and 20 seconds at 60° C. being one cycle. As a result, regarding the relative value of the signal intensity, the normal peripheral blood mononuclear cell specimen was 0.1, the KATO-III strain was 0.9±0.18, and the OCUM-1 strain was 1.5±0.27.

In Western blotting, ultrasonic crushing treatment was performed by adding PBS to a collected cell. The obtained slurry was applied to 12% acrylamide gel and SDS-PAGE was performed to separate a protein therefrom. The protein in the acrylamide gel after electrophoresis was transferred to a PVDF film. Blocking was performed on this transfer film for 1 hour at room temperature using 5% skimmed milk and a 1% BSA solution in order to suppress a nonspecific reaction. Thereafter, the transfer film was treated for 2 hours at room temperature using an anti-LIX1L rabbit polyclonal antibody (manufactured by Abnova Corporation) as a primary antibody and was treated for 1 hour at room temperature using a peroxidase-labeled goat anti-rabbit IgG polyclonal antibody (product name: Goat anti-Rabbit IgG-HRP, Invitrogen) as a secondary antibody, and Western blotting was performed. Western blotting was further performed on this transfer film using an anti-Actin mouse monoclonal antibody (product name: C-4, manufactured by ICN Biomedicals) as a primary antibody and a peroxidase-labeled sheep anti-mouse IgG monoclonal antibody (product name: NXA931, manufactured by Amersham) as a secondary antibody, as controls. Visualization of the band was performed using an ECL chemiluminescent reagent (manufactured by Amersham).

Figure 3A:
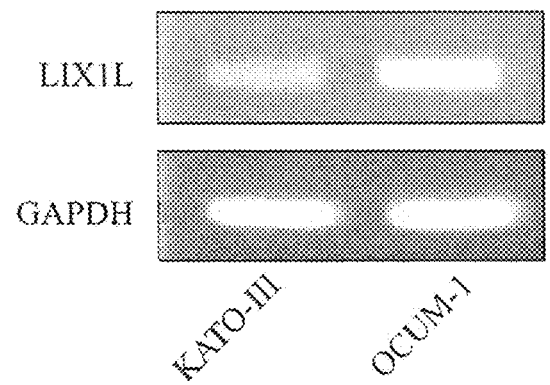
FIG. 3A is a view showing results in which fragments of cDNA of LIX1L genes of two kinds of gastric cancer cell strains amplified through an RT-PCR method are subjected to ethidium bromide staining in Reference Example 3.
Figure 3B:
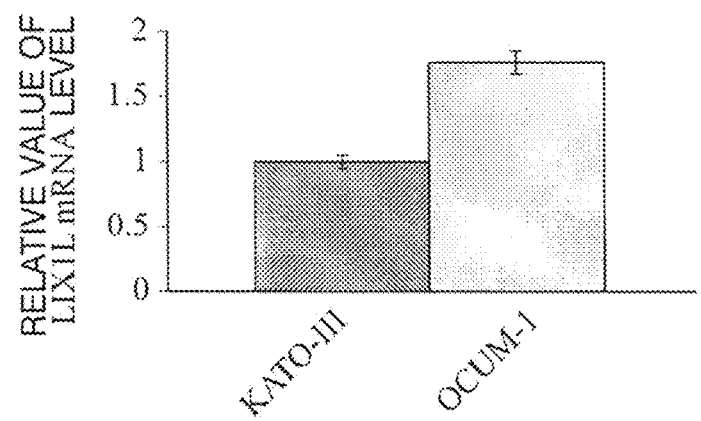
FIG. 3B is a view representing relative values of the expression levels of mRNA of LIX1L genes in two kinds of gastric cancer cell strains measured through the RT-PCR method, in Reference Example 3.
Figure 3C:
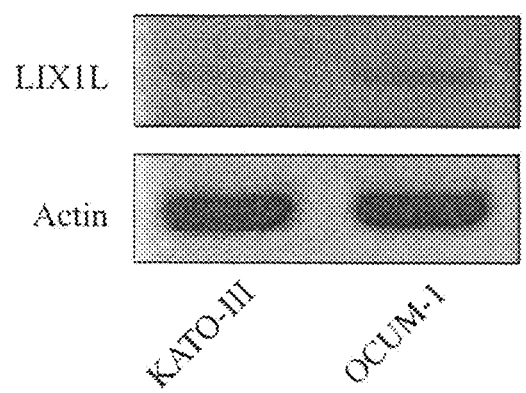
FIG. 3C is a view showing results in which the expression levels of the LIX1L genes in two kinds of gastric cancer cell strains are measured through a Western blotting method, in Reference Example 3.

FIG. 3A shows staining images in which electrophoresis is performed on products amplified through RT-PCR in each cell strain and a separated nucleic acid is stained using ethidium bromide. FIG. 3B shows relative values of the amount of mRNA of LIX1L obtained from the signal intensity of a band of LIX1L in the staining images in FIG. 3A of each of the cell strains (the amount of mRNA of LIX1L of a KATO-III strain was set to 1). FIG. 3C shows bands of LIX1L and Actin detected through Western blotting in each of the cell strains. The result was that, in the KATO-III strain and the OCUM-1 strain, the acceleration of the expression of LIX1L genes was recognized in both of the protein level and the mRNA level. The expression of LIX1L genes was higher in the OCUM-1 strain than that in the KATO-III strain.

Reference Example 4

The expression levels of LIX1L genes of hematopoietic organ tumor cell strains were quantitatively measured from both a protein level and an mRNA level through a Western blotting method and an RT-PCR method for comparison. The Western blotting method and the RT-PCR method were performed in the same manner as those in Reference Example 3 except that the hematopoietic organ tumor cell strains were used instead of the gastric cancer cell strains.

As the hematopoietic organ tumor cell strains, an acute myelogenous leukemia cell strain HL-60 strain, a chronic myelogenous leukemia cell strain K562 strain, and a multiple myeloma cell strain RPMI8226 strain were used. The HL-60 strain and the K562 strain are undifferentiated tumors and the RPMI8226 strain is a differentiated tumor. All of the cell strains were respectively analyzed after being cultured for 10 days in a culture solution in which 10 vol. % of fetal calf serum (FCS) with respect to an RPMI 1640 culture medium was added to the RPMI 1640 culture medium.

Figure 4A:
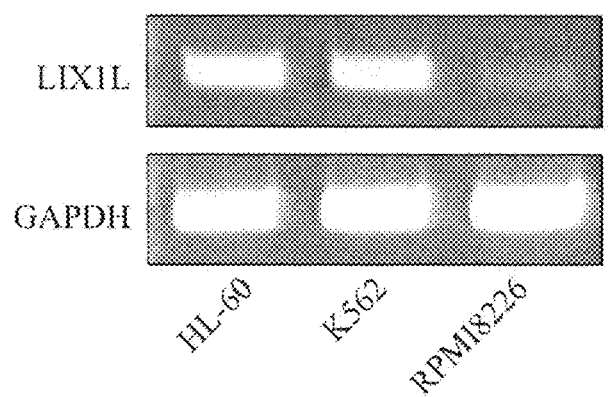
FIG. 4A is a view showing results in which fragments of cDNA of LIX1L genes of three kinds of hematopoietic organ tumor cell strains amplified through an RT-PCR method are subjected to ethidium bromide staining in Reference Example 4.
Figure 4B:
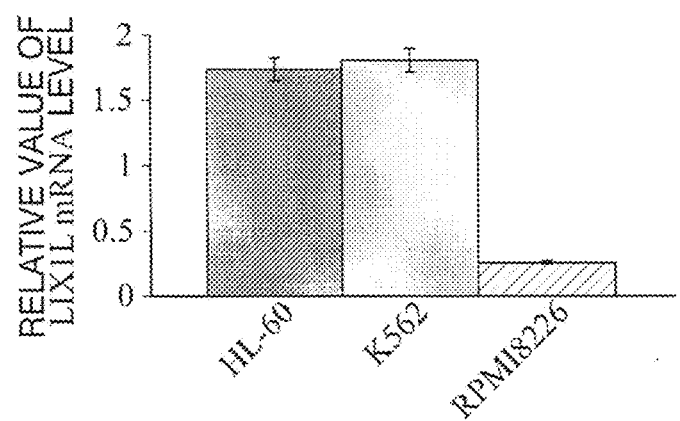
FIG. 4B is a view representing relative values of expression levels of mRNA of LIX1L genes in three kinds of hematopoietic organ tumor cell strains measured through the RT-PCR method, in Reference Example 4.
Figure 4C:
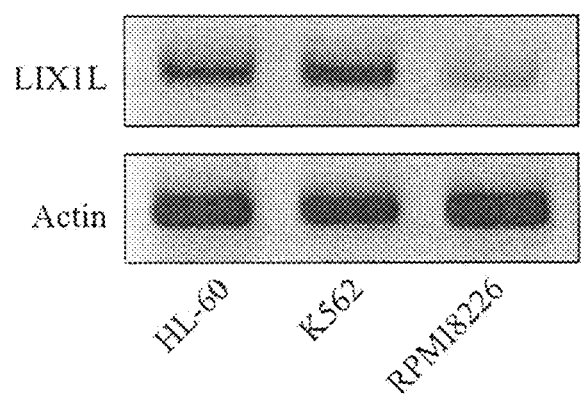
FIG. 4C is a view showing results in which the expression levels of the LIX1L genes in three kinds of hematopoietic organ tumor cell strains are measured through a Western blotting method, in Reference Example 4.
Figure 6A:
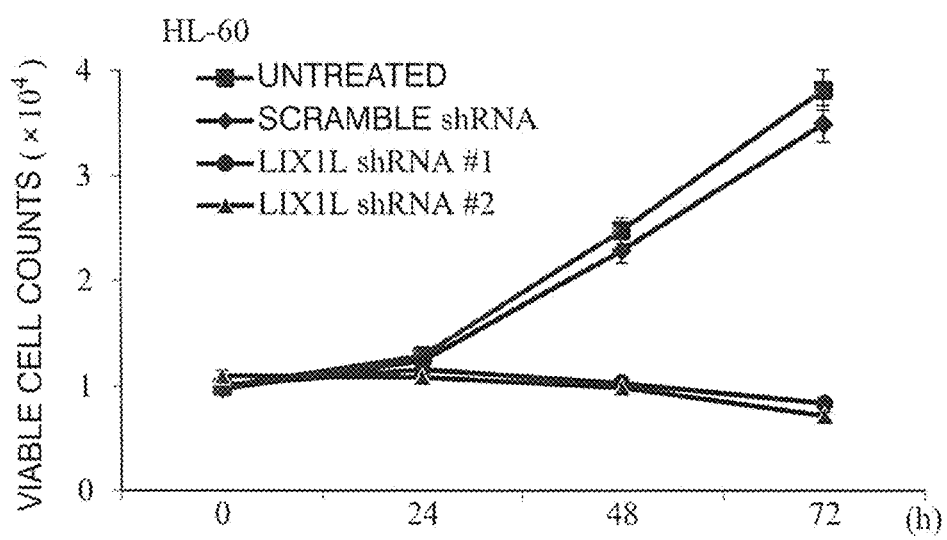
FIG. 6A is a view showing a temporal change in viable cell counts due to shRNA treatment of an HL-60 strain, in Example 1.
Figure 6B:
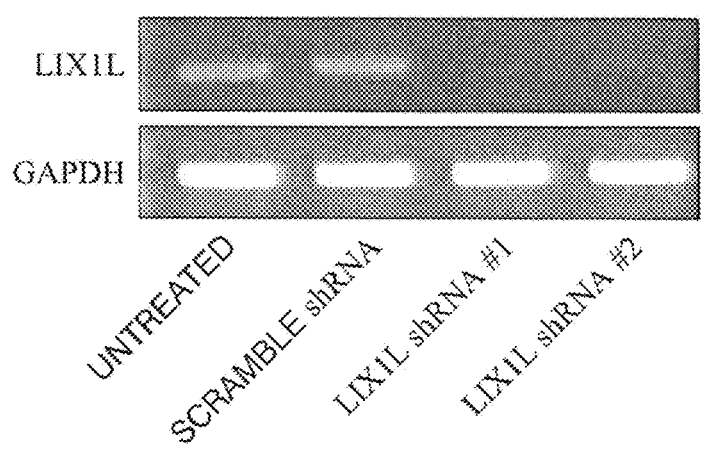
FIG. 6B is a view showing results in which the expression levels of LIX1L genes after culturing for 72 hours due to shRNA treatment of the HL-60 strain are measured through an RT-PCR method, in Example 1.
Figure 6C:
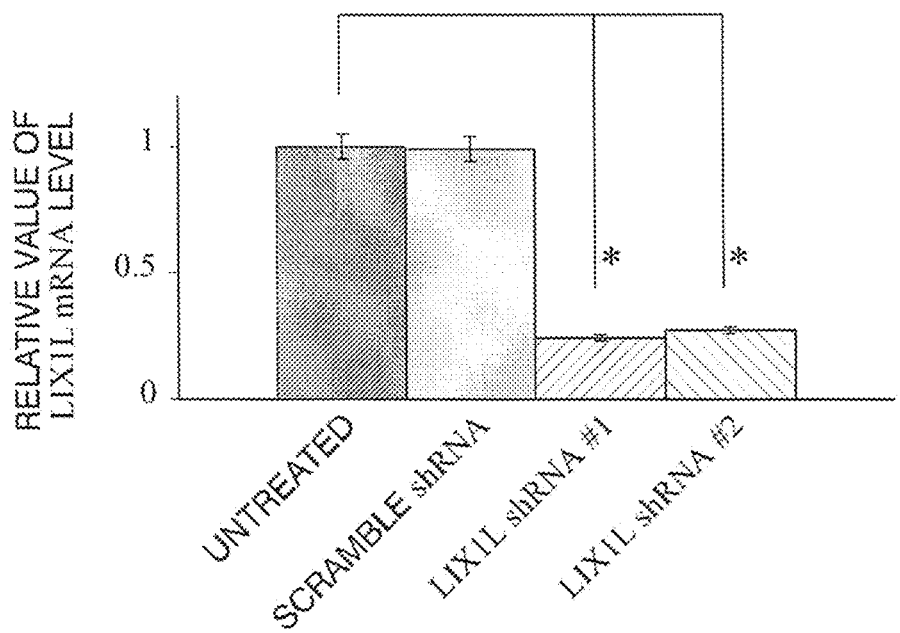
FIG. 6C is a view representing relative values of the expression levels of mRNA of the LIX1L genes after culturing for 72 hours due to shRNA treatment of the HL-60 strain measured through the RT-PCR method, in Example 1.
Figure 7A:
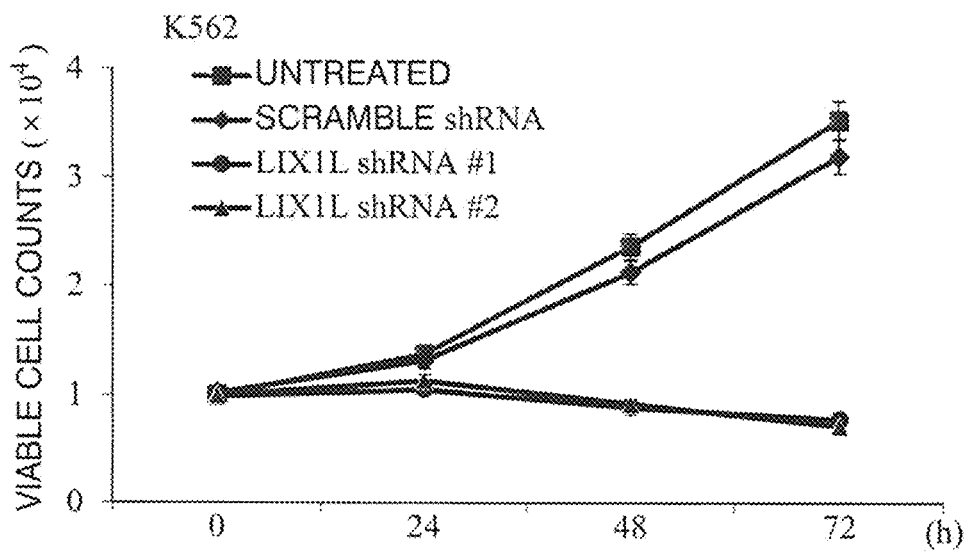
FIG. 7A is a view showing a temporal change in viable cell counts due to shRNA treatment of a K562 strain, in Example 1.
Figure 7B:
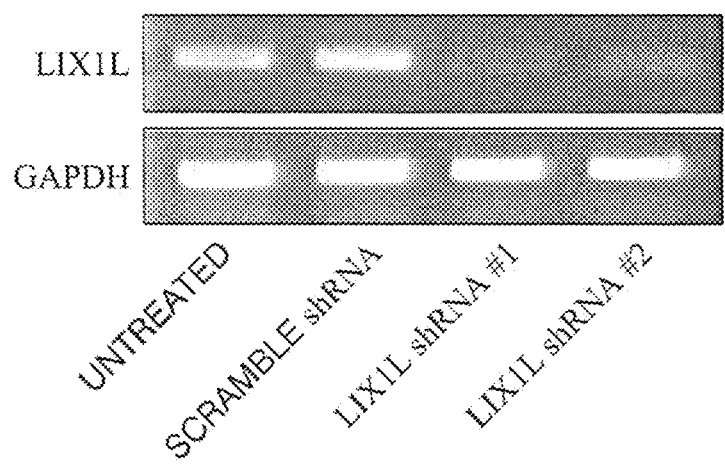
FIG. 7B is a view showing results in which the expression levels of LIX1L genes after culturing for 72 hours due to shRNA treatment of the K562 strain are measured through the RT-PCR method, in Example 1.
Figure 7C:
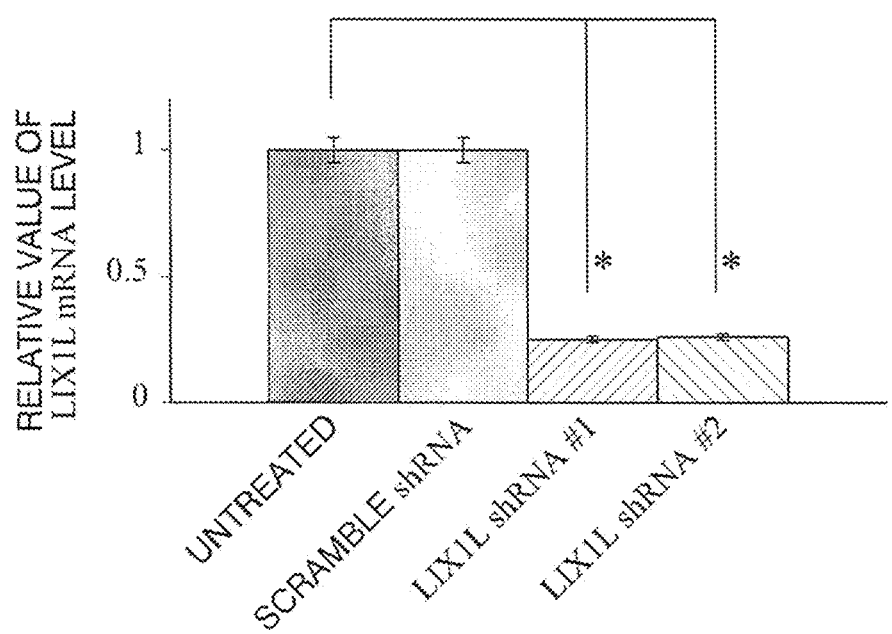
FIG. 7C is a view representing relative values of the expression levels of mRNA of the LIX1L genes after culturing for 72 hours due to shRNA treatment of the K562 strain measured through the RT-PCR method, in Example 1.
Figure 8A:
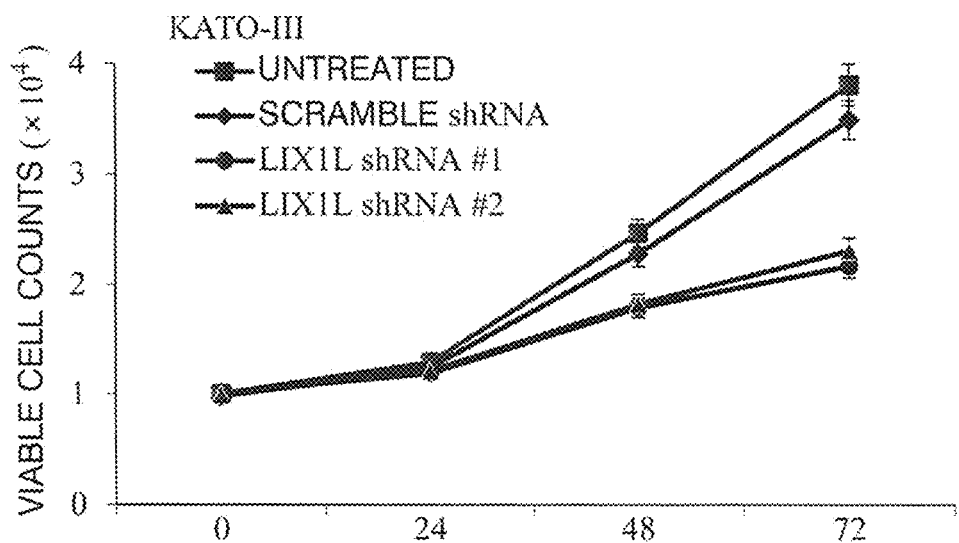
FIG. 8A is a view showing a temporal change in viable cell counts due to shRNA treatment of a KATO-III strain, in Example 1.
Figure 8B:
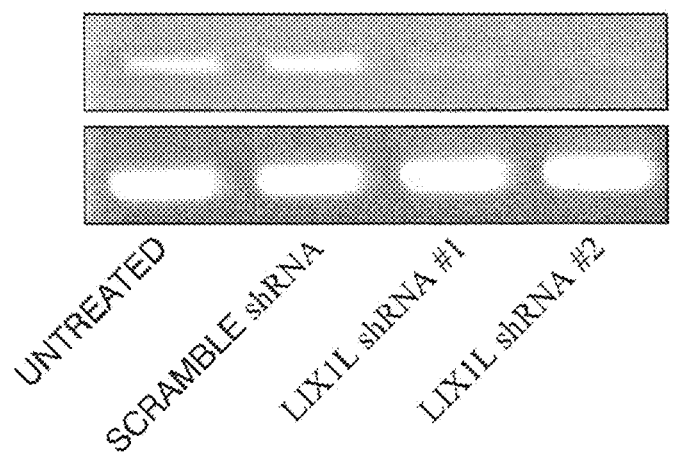
FIG. 8B is a view showing results in which the expression levels of LIX1L genes after culturing for 72 hours due to shRNA treatment of the KATO-III strain are measured through the RT-PCR method, in Example 1.
Figure 8C:
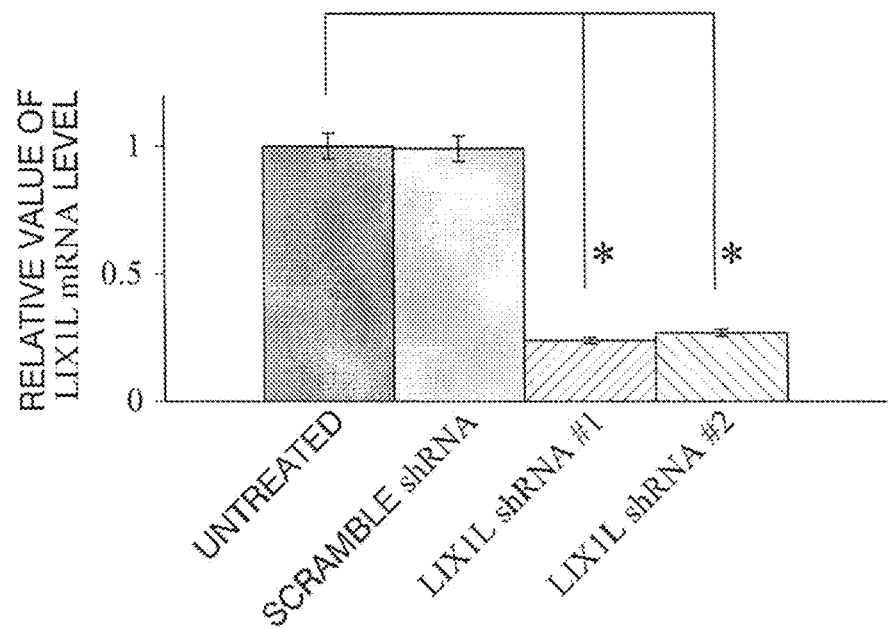
FIG. 8C is a view representing relative values of the expression levels of the LIX1L genes after culturing for 72 hours due to shRNA treatment of the KATO-III strain measured through the RT-PCR method, in Example 1.
Figure 9A:
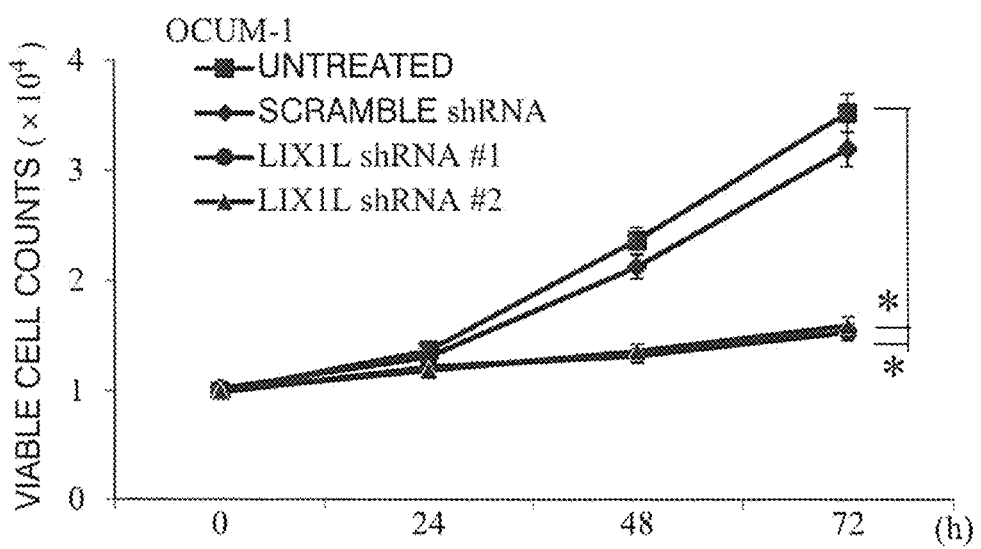
FIG. 9A is a view showing a temporal change in viable cell counts due to shRNA treatment of an OCUM-1 strain, in Example 1.
Figure 9B:
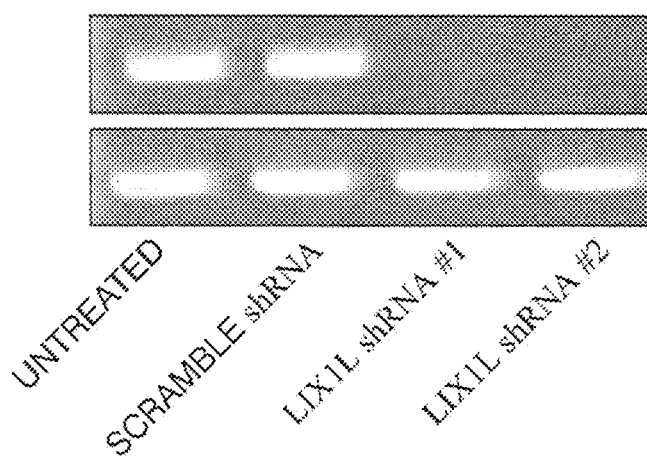
FIG. 9B is a view showing results in which the expression levels of LIX1L genes after culturing for 72 hours due to shRNA treatment of the OCUM-1 strain are measured through the RT-PCR method, in Example 1.
Figure 9C:
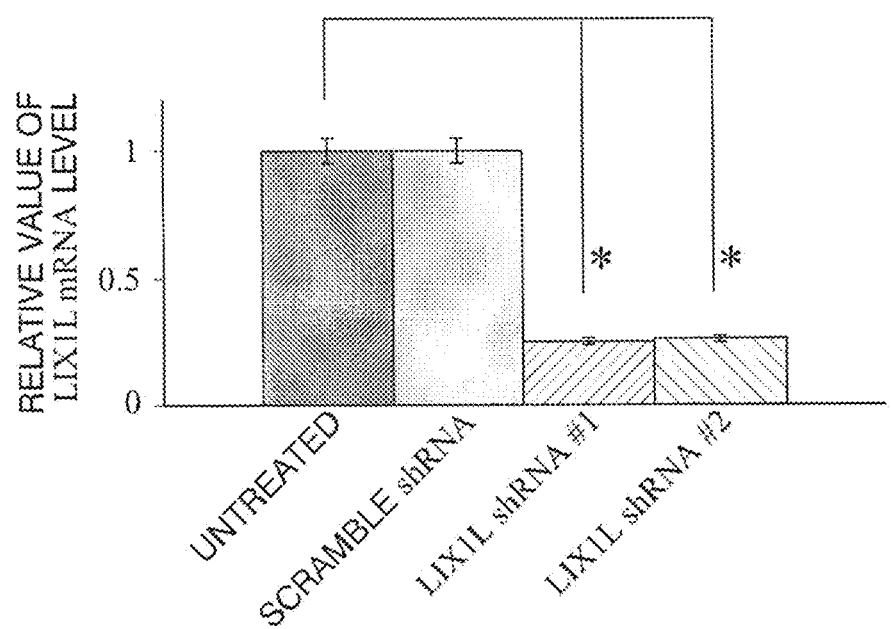
FIG. 9C is a view representing relative values of the expression levels of the LIX1L genes after culturing for 72 hours due to shRNA treatment of the OCUM-1 strain measured through the RT-PCR method, in Example 1.
Figure 11A:
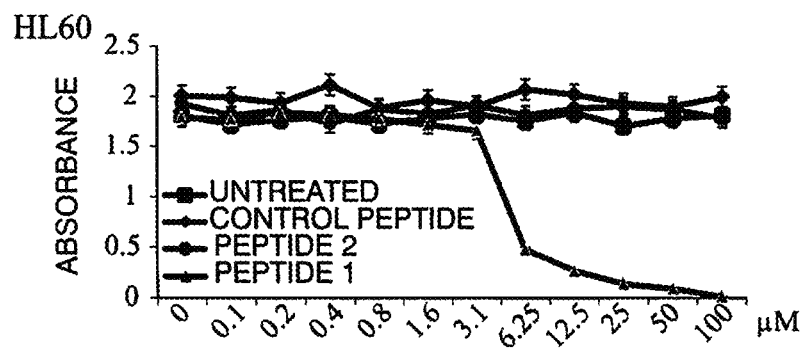
FIG. 11A is a view showing a relationship between the absorbance at 570 nm and the concentration of each peptide added to a culture solution when an MTT assay is performed on a cell of an HL-60 strain after being cultured by adding each of the peptides thereto, in Example 2.
Figure 11B:
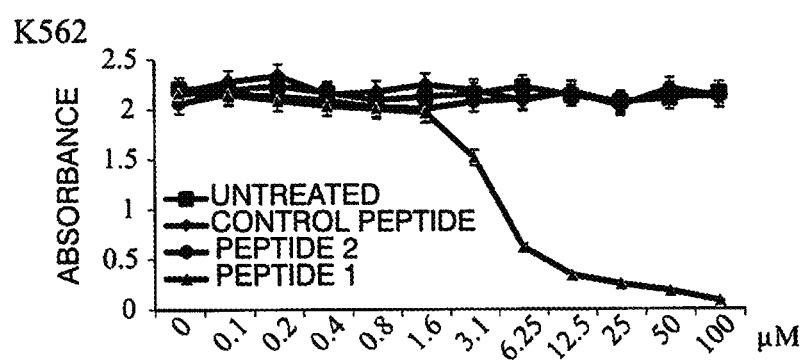
FIG. 11B is a view showing a relationship between the absorbance at 570 nm and the concentration of each peptide added to a culture solution when an MTT assay is performed on a cell of an HL-60 strain after being cultured by adding each of the peptides thereto, in Example 2.
Figure 11C:
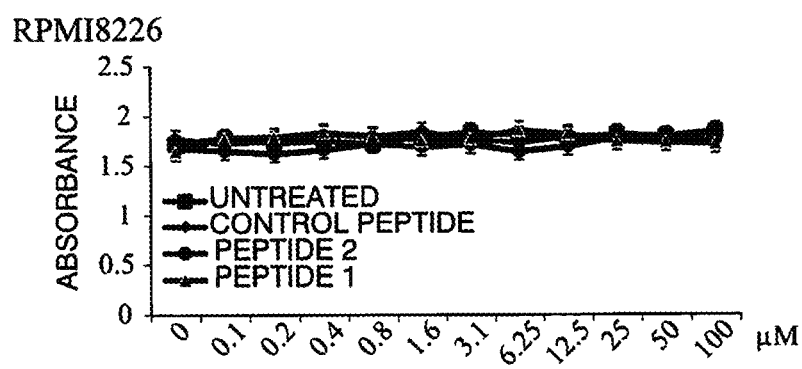
FIG. 11C is a view showing a relationship between the absorbance at 570 nm and the concentration of each peptide added to a culture solution when an MTT assay is performed on a cell of an RPMI8226 strain after being cultured by adding each of the peptides thereto, in Example 2.
Figure 11D:
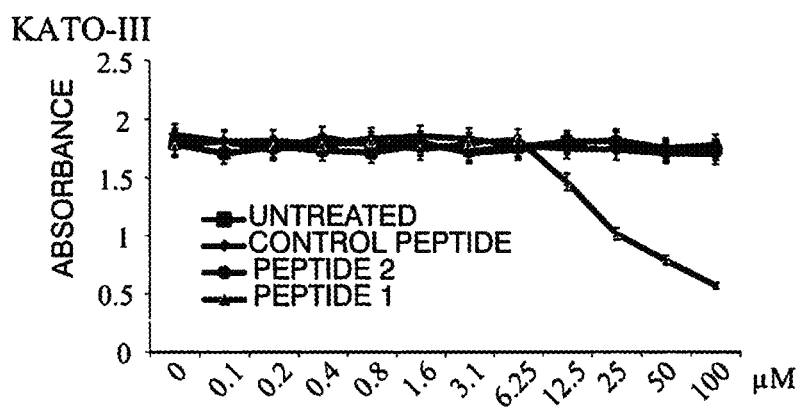
FIG. 11D is a view showing a relationship between the absorbance at 570 nm and the concentration of each peptide added to a culture solution when an MTT assay is performed on a cell of a KATO-III strain after being cultured by adding each of the peptides thereto, in Example 2.
Figure 11E:
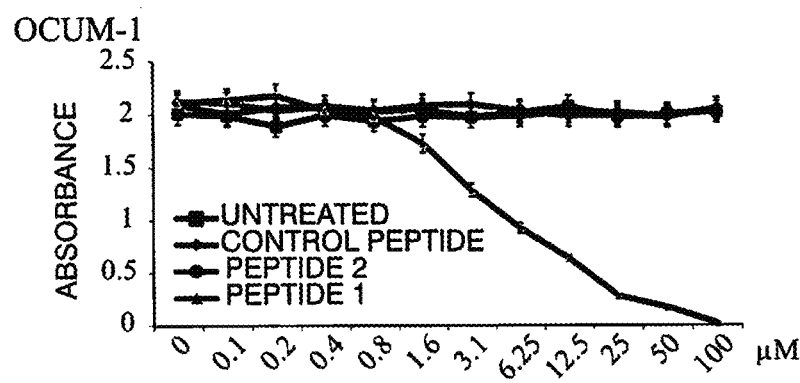
FIG. 11E is a view showing a relationship between the absorbance at 570 nm and the concentration of each peptide added to a culture solution when an MTT assay is performed on a cell of an OCUM-1 strain after being cultured by adding each of the peptides thereto, in Example 2.

FIG. 4A shows staining images in which electrophoresis is performed on products amplified through RT-PCR in each cell strain and a separated nucleic acid is stained using ethidium bromide. FIG. 4B shows relative values of the amount of mRNA of LIX1L obtained from the signal intensity of a band of LIX1L in the staining images in FIG. 4A of each of the cell strains (the signal intensity of a band of GAPDH was set to 1). FIG. 4C shows bands of LIX1L and Actin detected through Western blotting in each of the cell strains.

Regarding the relative value of the signal intensity of the band of LIX1L in the staining image of the ethidium bromide staining of each of the hematopoietic organ tumor cell strains, when the signal intensity of the band of GAPDH was set to 1, the myeloma cell strain RPMI8226 cell was 0.1, the HL-60 strain was 1.7±0.21, the K562 strain was 1.8±0.35, and the RPMI8226 strain was 0.2±0.03.

That is, in both of the protein level and the mRNA level, it was recognized that the expression levels of LIX1L genes in the HL-60 strain and the K562 strain which were undifferentiated tumors were significantly higher than that in the RPMI8226 strain which was a differentiated tumor, and the expression of the LIX1L genes was more accelerated in the HL-60 strain and the K562 strain than that in the RPMI8226 strain.

Example 1

In order to review the molecular biological role of a LIX1L protein in a cancer cell, two kinds of shRNA (#1 and #2) with respect to LIX1L genes were prepared and were introduced into a HL-60 strain, a K562 strain, a KATO-III strain, and an OCUM-1 strain. An effect of the inhibition of the expression of LIX1L genes on cell proliferation was reviewed. The base sequences of LIX1L shRNA #1 and LIX1L shRNA #2 are shown in FIGS. 5A and 5B. In FIGS. 5A and 5B, "Target sense sequence" represents a region homologous with mRNA of LIX1L and "Target antisense sequence" represents a region complementary to "Target sense sequence". In addition, as a comparative target, scramble shRNA was also used which does not have an ability to inhibit the expression of LIX1L genes.

The LIX1L shRNA #1 and LIX1L shRNA #2 can be produced through chemical synthesis.

Specifically, cells plated such that the density thereof became $1\times10^4$ cells/3.5 cm well for one plate (6 wells/plate) for each cell strain were cultured for one night in a culture solution having the same composition as those of the culture solutions described in the reference examples. After culturing of 1 well out of the 6 wells was completed, Trypan blue staining was performed on the 1 well, and viable cell counts were counted. The remaining 5 wells were cultured after exchanging the culture solution with a liquid mixture of a Lipofectamine (registered trademark) reagent (12.5 μL/well) and a culture solution (2 mL/well) of which the shRNA concentration became 2.5 μg/well. Then, Trypan blue staining was performed on 1 well 24 hours after the exchange of a culture medium, 1 well 48 hours after the exchange of a culture medium, and the remaining 1 well 72 hours after the exchange of a culture medium, and the viable cell counts were counted. As a control, the viable cell counts were measured (untreated) by performing the culturing similarly to the above except that a culture medium was exchanged with a culture solution to which no shRNA was added.

In addition, apart from this, cells plated such that the density thereof became $1\times10^4$ cells/3.5 cm well for one plate (6 wells/plate) for each cell strain were cultured for one night in a culture solution having the same composition as those of the culture solutions described in the reference examples, in order to perform RT-PCR. Thereafter, the culture solution was exchanged with a liquid mixture of a Lipofectamine (registered trademark) reagent (12.5 μL/well) and a culture solution (2 mL/well) of which the shRNA concentration became 2.5 μg/well, and the cells were collected for 72 hours. RT-PCR was performed on the collected cells in the same manner as that in the Reference Example 3 and fragments of cDNA of LIX1L genes and fragments of cDNA of GAPDH genes were amplified. Agarose gel electrophoresis was performed on the obtained amplified products and an ethidium bromide staining image of a separated nucleic acid was obtained. As a control, RT-PCR was performed by performing culturing similarly to the above except that a culture medium was exchanged with a culture solution to which no shRNA was added, and RT-PCR was performed to obtain an ethidium bromide staining image (untreated).

The measurement results of cell strains are shown in FIGS. 6A to 9C. FIGS. 6A, 7A, 8A, and 9A show measurement results of the viable cell counts. FIGS. 6B, 7B, 8B, and 9B show the staining images of ethidium bromide staining of fragments of LIX1L and fragments of GAPDH amplified through RT-PCR after the culturing for 72 hours. FIGS. 6C, 7C, 8C, and 9C show relative values (the amount of mRNA of untreated LIX1L is set to 1) of the amount of mRNA of LIX1L obtained from the signal intensities of bands of LIX1L in the staining images of FIGS. 6B, 7B, 8B, and 9B in the cell strains. The results were that, in all of the cell strains, the number of cells and the expression levels of LIX1L genes of cells into which scramble shRNA was introduced were the same as those of untreated cells into which shRNA was not introduced. However, although there was no particular difference in the viable cell counts in cells, into which LIX1L shRNA #1 and LIX1L shRNA #2 were introduced, compared to that in the untreated cells, until the point of time after the lapse of 24 hours, the viable cell counts in cells, into which LIX1L shRNA #1 and LIX1L shRNA #2 were introduced, decreased more clearly than that of the untreated cells, after the lapse of 48 hours and 72 hours. In addition, in the result of RT-PCR after the lapse of 72 hours, the expression of LIX1L genes was hardly observed in the cells into which LIX1L shRNA #1 and LIX1L shRNA #2 were introduced, and it was confirmed that the expression of LIX1L genes was inhibited by the LIX1L shRNA #1 and the LIX1L shRNA #2. From these results, inhibition of cell proliferation due to inhibition of the expression of LIX1L genes was recognized in these four kinds of cell strains which were high LIX1L-expressing tumor cells, and it was inferred that the expression of LIX1L was involved in the cell proliferation. In addition, the effect of inhibiting the cell proliferation in the KATO-III strain in which the expression levels of LIX1L genes were lowest among these four kinds of cell strains was lower than those of other cell strains.

Example 2

There are five tyrosine residues (Y95, Y126, Y136, Y139, and Y263) in a LIX1L protein. The probability of phosphorylation of these tyrosine residues was predicted and it was expected that there was the highest probability that Y136 was phosphorylated. Peptides which respectively have the same amino acid sequences as an amino acid sequence containing Y136 and Y139 and as an amino acid sequence containing Y139 but no Y136, in amino acid sequences of the LIX1L protein, were chemically synthesized. These peptides are peptides (peptide 1: SEQ ID No: 12, peptide 2: SEQ ID No: 13) in which the C-terminal of a peptide consisting of a Tat sequence represented by SEQ ID No: 7 and the N-terminal of a partial amino acid sequence of a LIX1L protein including the tyrosine residues are connected to each other using ε-aminocaproic acid. In addition, a peptide in which ε-aminocaproic acid is bonded to the C-terminal of a peptide consisting of a Tat sequence was also chemically synthesized (control peptide: SEQ ID No: 14). The amino acid sequences of these peptides are shown in FIG. 10 together with the partial amino acid sequence of a LIX1L protein.

The control peptide, the peptide 1, or the peptide 2 was introduced into an HL-60 strain, a K562 strain, an RPMI8226 strain, a KATO-III strain, and an OCUM-1 strain, and the influence on cell proliferation was examined. The evaluation of the cell proliferation was performed through an MTT method in which a reduction reaction in mitochondria is used.

Specifically, first, cells plated in a 96-well microplate such that the density thereof became $5\times10^3$ cells/well were cultured for one night in a culture solution having the same composition as those in the reference examples. Thereafter, the culture solution was exchanged with 100 μL of a culture solution of which the concentration of peptides is 0 μM to 100 μM for culturing for 72 hours. After the culturing, an MTT-containing PBS solution was added to the culture solution, and the mixture was incubated for 4 hours. Then, formazan which was generated by putting 100 μL of isopropanol (containing 34 (v/v) % of hydrochloric acid) into each of the wells was dissolved. The absorbance of each of the wells of the microplate at 570 nm was measured using a microplate reader. As controls, culturing was performed in the same manner except that no peptide was added to the strains, an MTT assay was performed thereon, and the absorbance at 570 nm was measured (untreated).

The measurement results of the absorbance of each of the cell strains at 570 nm are shown in FIGS. 11A to 11E. The results were that, in all of the cell strains, the absorbance at 570 nm in the case of introducing the control peptide into the strains did not particularly change similarly to the untreated case in which no peptide was introduced into the strains, even if the concentration of peptides was increased up to 100 µM, and it was confirmed that there was no influence on the cell proliferation even if the control peptide was introduced into the strains. Even in a case of introducing a peptide 2 into the strains, in all of the strains, there was no particular change in the absorbance at 570 nm even if the concentration thereof was increased up to 100 µM similarly to that of the control peptide. In contrast, in a case where a peptide 1 was introduced into the strains, a dominant effect of inhibiting the cell proliferation was recognized at a concentration of greater than or equal to 6.25 µM in the HL-60 strain, the K562 strain, and the OCUM-1 strain, and a dominant effect of inhibiting the cell proliferation was recognized at a concentration of greater than or equal to 25 µM in the KATO-III strain. However, in the RPMI8226 strain, there was no particular change in the absorbance at 570 nm even if the concentration of the peptide 1 was increased up to 100 µM similarly to the control peptide, and no effect of inhibiting the cell proliferation due to the peptide 1 was recognized. From these results, it can be seen that the peptide (that is, Y136-containing peptide) having the same amino acid sequence as that in a partial region containing Y136 of a LIX1L protein shows an effect of inhibiting the cell proliferation with respect to high LIX1L-expressing cells and the effect is not seen in low LIX1L-expressing cells. Furthermore, among the high LIX1L-expressing cells, the effect of inhibiting the cell proliferation due to peptide 1 in the HL-60 strain, the K562 strain, and the OCUM-1 strain in which the expression levels of LIX1L genes were comparatively high was higher than that in the KATO-III strain. Accordingly, it was found that the proliferation inhibition effect of the tumor cell proliferation-inhibiting peptide, such as a Y136-containing peptide, according to the present invention varied depending on the expression levels of LIX1L genes and it was inferred that the proliferation inhibition effect in the high LIX1L-expressing cells was more effective than that in the low LIX1L-expressing cells.

Example 3

The control peptide, the peptide 1, or the peptide 2 was introduced into an HL-60 strain, a K562 strain, and an RPMI8226 strain, and the influence on cell proliferation was examined. The evaluation of the cell proliferation was performed through measuring the viable cell counts similarly to Example 1.

Specifically, the viable cell counts were measured after culturing the cells similarly to Example 1 except that a 5 µM culture solution containing a control peptide, a peptide 1, or a peptide 2 was used instead of the culture solution (2 mL/well) of which the shRNA concentration was 2.5 µg/well. The viable cell counts were measured (untreated) by performing the culturing similarly to Example 1 using a culture solution containing no peptide 2, as a control.

Figure 12A:
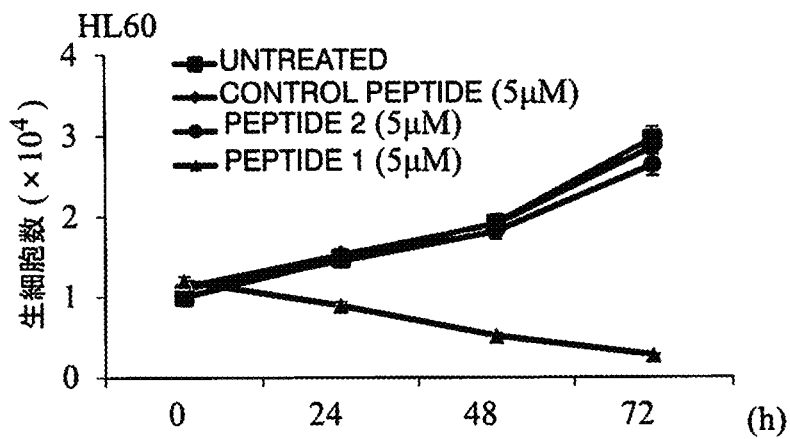
FIG. 12A is a view showing a temporal change in viable cell counts in a case where each peptide is added to an HL-60 strain for culturing, in Example 3.
Figure 12B:
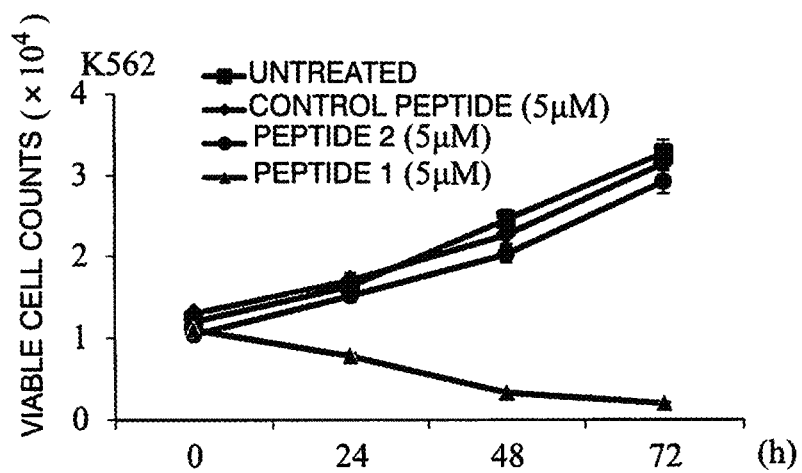
FIG. 12B is a view showing a temporal change in viable cell counts in a case where each peptide is added to a K562 strain for culturing, in Example 3.
Figure 12C:
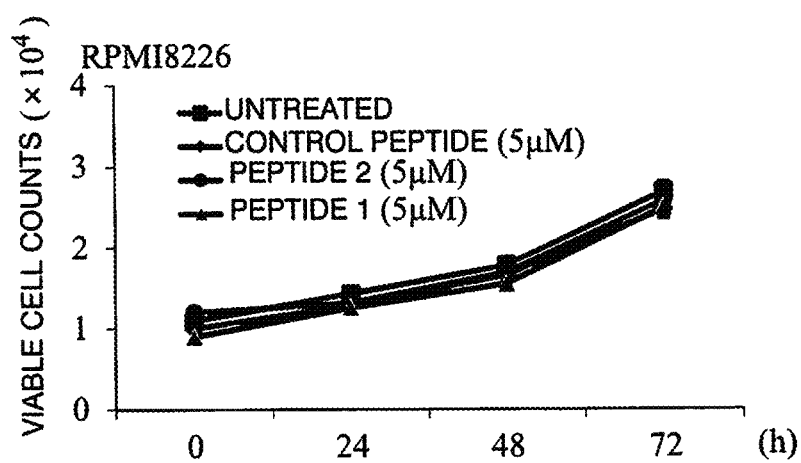
FIG. 12C is a view showing a temporal change in viable cell counts in a case where each peptide is added to a RPMI8226 strain for culturing, in Example 3.

The measurement results of the viable cell counts of the cell strains are shown in FIGS. 12A to 12C. The results were that, in all of the cell strains, in a case where the control peptide was introduced into the cell strains and in a case where the peptide 2 was introduced into the strains, the viable cell counts were the same as those in an untreated case where no peptide was introduced into the cell strains, even at the point of time after the lapse of 72 hours. In contrast, in a case where the peptide 1 was introduced into the cell strains, the viable cell counts decreased in the HL-60 strain and the K562 strain more than that in the untreated case already at the point of time after the culturing for 24 hours, and the viable cell counts were very small after the culturing for 72 hours. In contrast, in the RPMI8226 strain, even in the case where the peptide 1 was introduced thereinto, the viable cell counts therein were the same as those in the untreated case. Even from these results, it can be seen that the cell proliferation is inhibited by introducing the tumor cell proliferation-inhibiting peptide according to the present invention including the peptide 1 into a high LIX1L-expressing cell.

Example 4

In the peptide 1 used in Examples 2 and 3, the Y136-containing partial sequence consists of 11 amino acids. Therefore, a peptide 3 (SEQ ID No: 15) in which the Y136-containing partial sequence consists of 20 amino acids and a peptide 4 (SEQ ID No: 16) in which the Y136-containing partial sequence consists of 30 amino acids were produced through chemical synthesis for comparing the effects of inhibiting the cell proliferation of the peptides 3 and 4 with that of the peptide 1. An amino acid sequence of a LIX1L protein is shown in FIG. 13A and amino acid sequences of the peptides 1, 3, and 4, and the control peptide are shown in FIG. 13B. The Y136-containing partial sequences of the peptides 1, 3, and 4 are shown in FIG. 13A.

As cell strains into which the peptides were introduced, a U937 strain, a K562 strain, and an RPMI8226 strain were used. The U937 strain was a high LIX1L-expressing tumor cell in which LIX1L expression equivalent to that in the K562 strain was confirmed.

Specifically, the cells were cultured for 72 hours similarly to Example 2 except that a peptide to be added to a cell strain was set to peptide 1, 3, or 4, or a control peptide, an MTT assay was performed thereon, and the absorbance at 570 nm was measured.

Figure 14A:
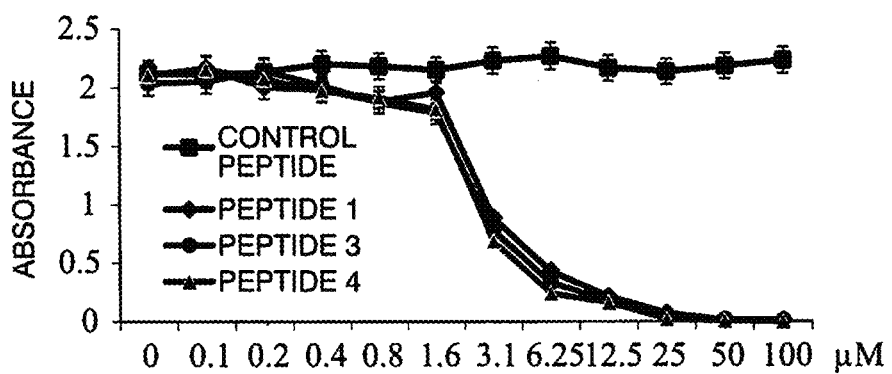
FIG. 14A is a view showing a relationship between the absorbance at 570 nm and the concentration of each peptide added to a culture solution when an MTT assay is performed on a cell of a U937 strain after being cultured by adding each of the peptides thereto, in Example 4.
Figure 14B:
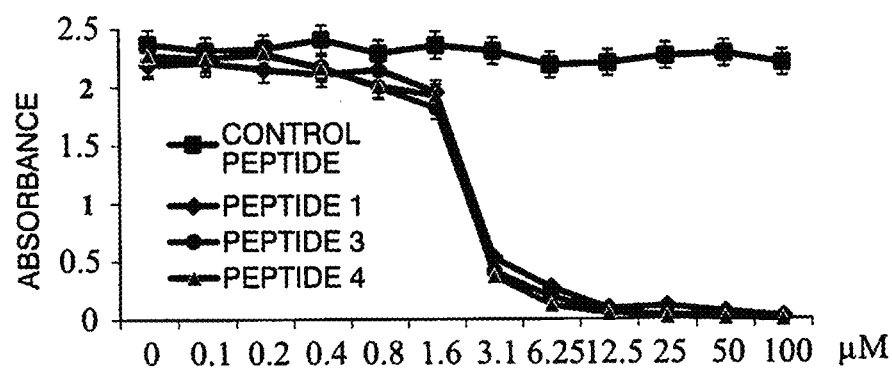
FIG. 14B is a view showing a relationship between the absorbance at 570 nm and the concentration of each peptide added to a culture solution when an MTT assay is performed on a cell of a K562 strain after being cultured by adding each of the peptides thereto, in Example 4.
Figure 14C:
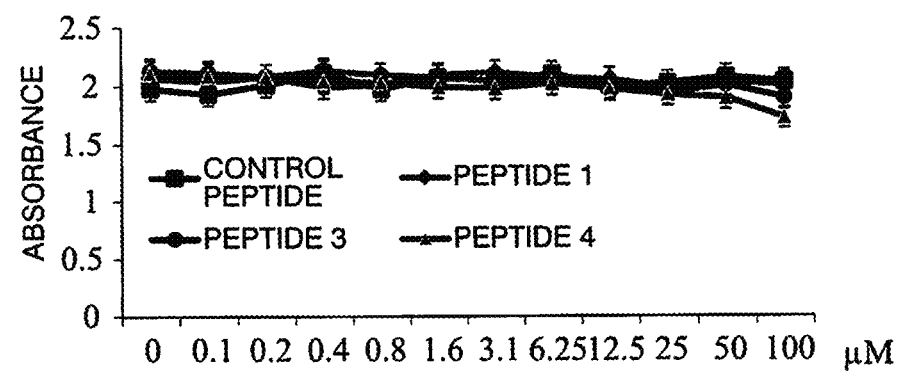
FIG. 14C is a view showing a relationship between the absorbance at 570 nm and the concentration of each peptide added to a culture solution when an MTT assay is performed on a cell of a RPMI8226 strain after being cultured by adding each of the peptides thereto, in Example 4.

The measurement results of the absorbance of each of the cell strains are shown in FIGS. 14A to 14C. The results were that the cell proliferation was inhibited by introducing the peptide 1, 3, or 4 into the U937 strain and the K562 strain. All of the cell proliferation inhibition effects of the peptides 1, 3, and 4 in the U937 strain and the K562 strain were the same as each other. In addition, in the RPMI8226 strain, the cell proliferation was not inhibited similarly to the control peptide even if the peptide 1, 3, or 4 was introduced thereinto.

Reference Example 5

A LIX1L protein with a FLAG tag was forcibly expressed in a HEK293 strain, and intracellular localization of the LIX1L protein, and the presence and absence of phosphorylation of serine, threonine, and tyrosine were examined.

First, a stable expression strain (293 FLG/LIX1L), in which a LIX1L protein (FLAG/LIX1L protein, SEQ ID No: 17) to which a FLAG tag was attached to the N-terminal was forcibly expressed, and a stable expression strain (293 FLG), in which only a FLAG protein was forcibly expressed, were prepared. The stable expression strains were prepared using a Flp-in (registered) trademark system (manufactured by Invitrogen).

Specifically, first, a FLG/LIX1L fusion gene was inserted into a BamHI/XhoI site of plasmid pcDNA5/FRT (V6010-20; manufactured by Invitrogen) using plasmid pcDNA5/FRT as an expression vector, to prepare a FLG/LIXIL expression vector (pcDNA5/FLG/LIX1L/FRT). Genes of pcDNA5/FLG/LIX1L/FRT and pOG44 (V6005-20; manufactured by Invitrogen) which was a Flp recombinase expression vector were introduced into a Flp-In-293 strain (Flp-In host cell in which one FRT site is included in a genome) (R750-07; manufactured by Invitrogen) using Lipofectamine 2000 Kit (V6005-20; manufactured by Invitrogen); culturing was performed thereon for 4 weeks using a 10% FCS-containing DMEM culture medium to which Hygromycin B (manufactured by Invitrogen) at a final concentration of 100 mg/mL was added; and a cell (293 FLG/LIX1L cell) in which a target gene was inserted into a chromosome was selectively proliferated. As a comparison, a cell (293 FLG cell) into which a gene of only a control vector (pcDNA5/FLG/FRT) was introduced was simultaneously cultured and proliferated.

Next, a 293 FLG/LIX1L cell and a 293 FLG cell were respectively cultured in 10% FCS-containing DMEM culture media to which Hygromycin B at 100 mg/mL was added, for 10 days to 14 days. Then, the cultured cells were separated into nuclear fractions and cytoplasm fractions using Nuclear/Cytosol Fractionation Kit (manufactured by BioVison, Inc.). Immunoprecipitation was performed on both the obtained fractions using an anti-FLAG antibody (manufactured by Sigma-Aldrich Co. LLC.) and an agarose-binding protein A (manufactured by Sigma-Aldrich Co. LLC.), protein separation was performed thereon through 12% SDS-PAGE, and the fractions were transferred to a film. Western blotting was performed on the fractions-transferred film using an anti-FLAG antibody, an anti-LIX1L antibody (manufactured by Abnova Corporation), an anti-phosphorylated threonine antibody (manufactured by Abeam plc.), anti-phosphorylated serine antibody (manufactured by Abeam plc.), and an anti-phosphorylated tyrosine antibody (manufactured by Abcam plc.).

Figure 15:
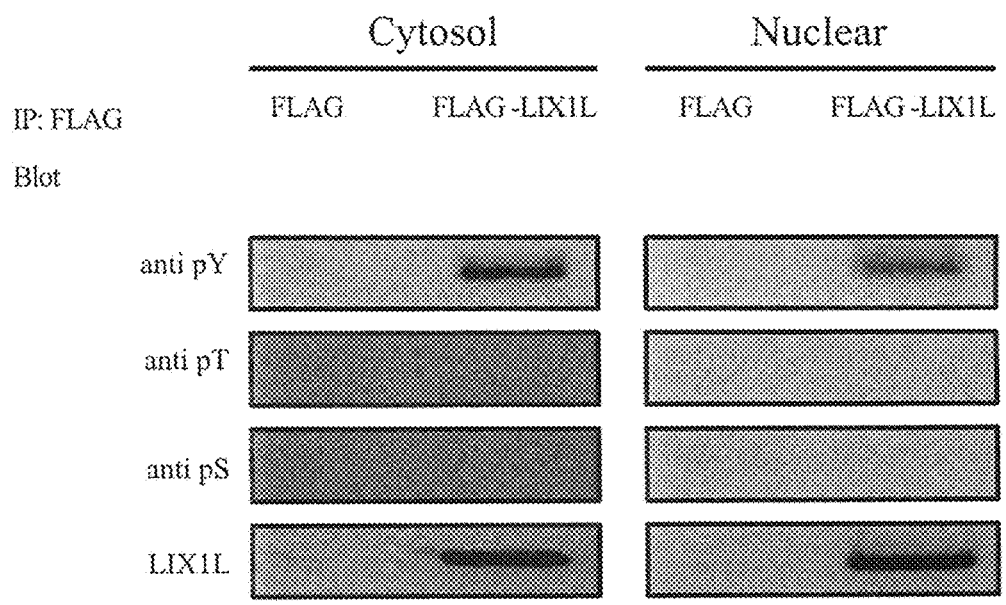
FIG. 15 is a view showing results in which immunoprecipitation using an anti-FLAG antibody is performed on a lysate of a stable expression strain in which a LIX1L protein with a FLAG tag is forcibly expressed in a HEK293 strain, and Western blotting is performed on the obtained precipitate, in Reference Example 5.

The results of Western blotting of immunoprecipitates using an anti-FLAG antibody are shown in FIG. 15. From the results, it was found that FLAG/LIX1L proteins existed in both of the cytoplasm fractions and the nuclear fractions. In addition, in all of the FLAG/LIX1L proteins existing in both kinds of fractions, tyrosine was phosphorylated, but no phosphorylation of serine or threonine was confirmed.

Reference Example 6

The expression levels of LIX1L of the 293 FLG and 293 FLG/LIX1L prepared in Reference Example 5, a NUGC-4 strain (gastric cancer cell strain), an MKN45 strain (gastric cancer cell strain), a K562 strain (chronic myelogenous leukemia cell strain), an HL-60 strain (acute myelogenous leukemia cell strain), and a U937 strain (acute myelogenous leukemia cell strain) were examined through PCR.

Regarding 293 FLG, a cell in which a FLAG protein was forcibly expressed similarly to Reference Example 5 by introducing plasmid pcDNA5/FLG/FRT into a Flp-In-293 strain was collected. Regarding 293 FLG/LIX1L, a cell in which a FLAG/LIX1L protein was forcibly expressed similarly to Reference Example 5 by introducing a FLAG/LIX1L protein expression vector (pcDNA5/FLG/LIX1L/FRT) into a Flp-In-293 strain was also collected. Regarding the K562 strain, the HL-60 strain, the NUGC-4 strain, the MKN45 strain, and the U937 strain, each cell which was cultured for 10 days to 14 days in a culture solution in which 10 vol. % of fetal calf serum (FCS) with respect to an RPMI 1640 culture medium was added to the RPMI 1640 culture medium was collected.

Each total RNA was collected from each collected cell similarly to Reference Example 3 except that the number of cycles of PCR was set to 24 cycles, 25 cycles, or 27 cycles; fragments of GAPDH and fragments of cDNA of LIX1L genes of 218 bp were amplified through RT-PCR; electrophoresis was performed on the obtained amplified products; and a separated nucleic acid was subjected to ethidium bromide staining.

Figure 16A:
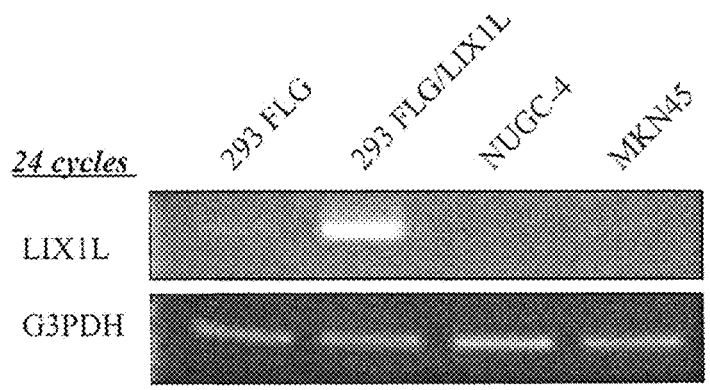
FIG. 16A is a view showing results in which fragments of cDNA of LIX1L genes of strains amplified through an RT-PCR method are subjected to ethidium bromide staining in Reference Example 6.
Figure 16B:
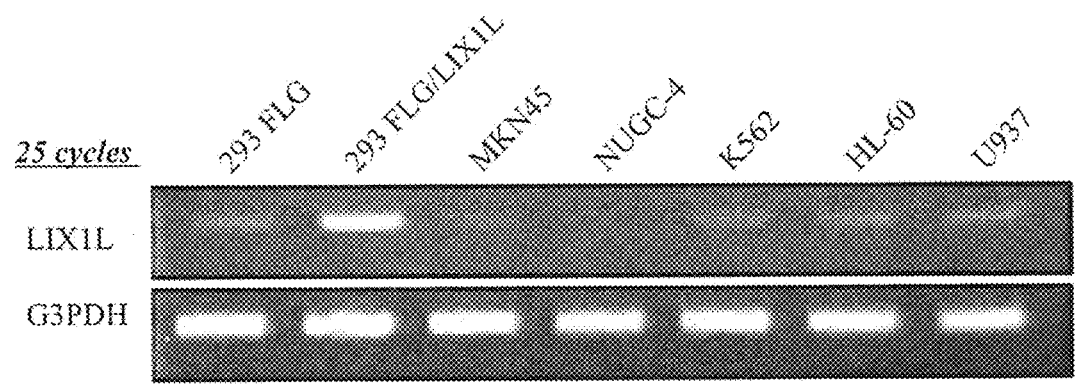
FIG. 16B is a view showing results in which fragments of cDNA of LIX1L genes of strains amplified through an RT-PCR method are subjected to ethidium bromide staining in Reference Example 6.
Figure 16C:
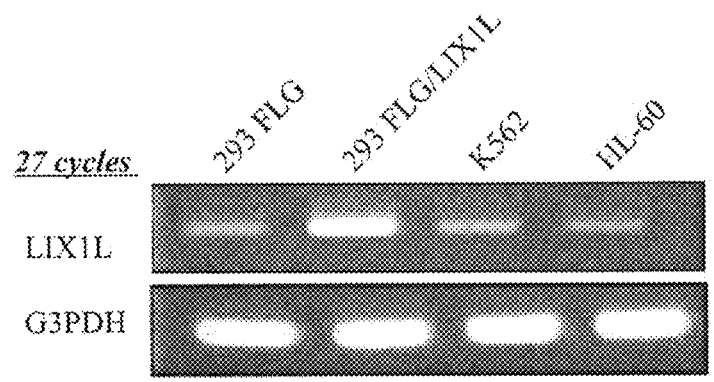
FIG. 16C is a view showing results in which fragments of cDNA of LIX1L genes of strains amplified through an RT-PCR method are subjected to ethidium bromide staining in Reference Example 6.

Staining images of ethidium bromide staining are shown in FIGS. 16A, 16B, and 16C. From these results, the expression level of LIX1L was largest in 293 FLG/LIX1L; the expression levels of 293 FLG, the K562 strain, the HL-60 strain, and the U937 strain were the same as each other; and the expression of LIX1L could hardly be checked at the point of time of 25 cycles in the NUGC-4 strain. The expression level of LIX1L of the MKN45 strain was obviously larger than that of the NUGC-4 strain while the expression level thereof was smaller than that of the K562 strain or the like.

Example 5

A control peptide or a peptide 1 was introduced into 7 strains of which the expression level of LIX1L had been examined in Reference Example 6, similarly to Example 3, and the influence on cell proliferation was examined. The evaluation of the cell proliferation was performed through a method for measuring the viable cell counts similarly to Example 1 and a method for performing an MTT assay similarly to Example 2.

In the method for measuring the viable cell counts, cells were cultured for 3 days similarly to Example 1 except that a 25 µM (10 µM for an HL-60 strain, a K562 strain, and a U937 strain) culture solution containing a control peptide or a peptide 1 was used, and the viable cell counts were measured. As a comparison, culturing was performed similarly to the above using a culture solution containing no peptide, and the viable cell counts were measured (untreated).

In addition, in the method for performing an MTT assay, cells were cultured for 72 hours similarly to Example 2 except that a peptide to be added to a strain was set to a control peptide or a peptide 1 at 25 µM (10 µM for an HL-60 strain, a K562 strain, and a U937 strain), an MTT assay was performed thereon, and the absorbance at 570 nm was measured. As a comparison, culturing was performed similarly to the above using a culture solution containing no peptide, and the MTT assay was performed thereon (untreated).

Figure 17A:
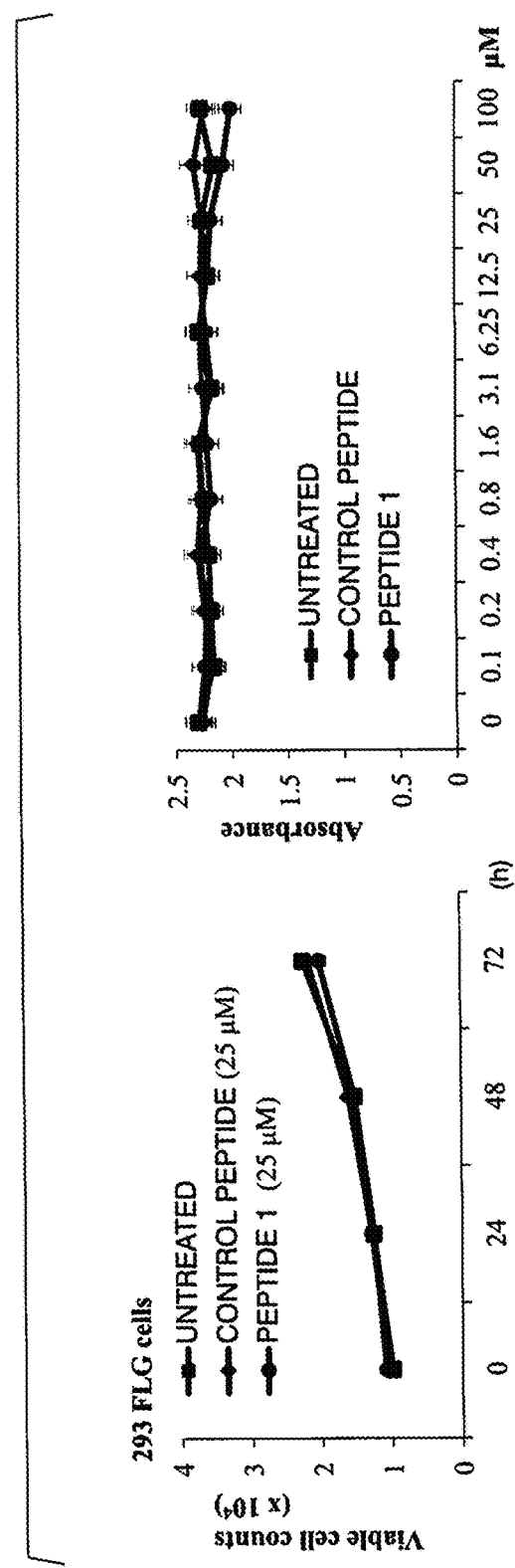
FIG. 17A is a view showing measurement results (left) of viable cell counts of cells (293 FLG) in which only FLAG is forcibly expressed in a Flp-In-293 strain, and results (right) of an MTT assay, in Example 5.
Figure 17B:
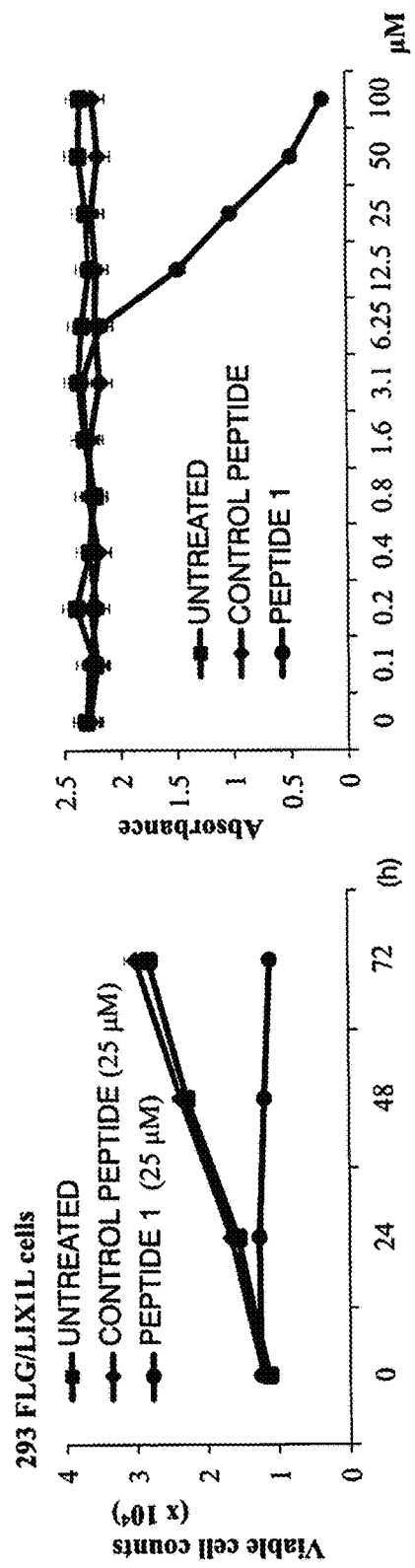
FIG. 17B is a view showing measurement results (left) of viable cell counts of cells (293 FLG/LIX1L) in which a LIX1L protein with a FLAG tag is forcibly expressed in a Flp-In-293 strain, and results (right) of an MTT assay, in Example 5.
Figure 18A:
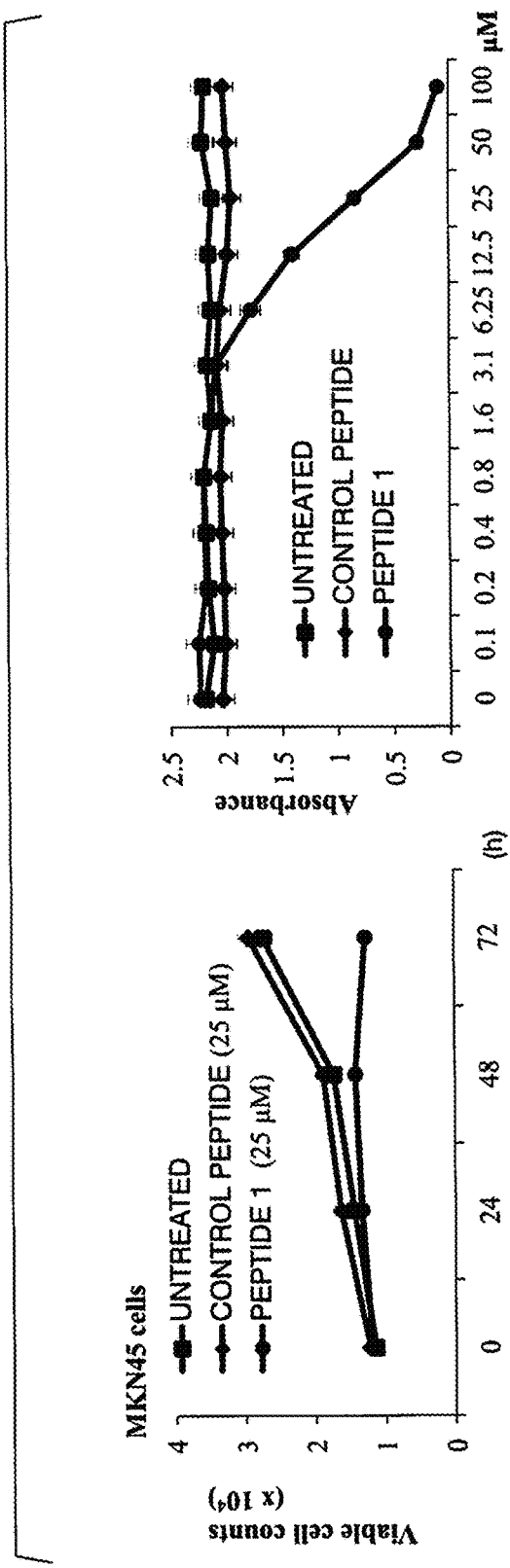
FIG. 18A is a view showing results (left) in which the viable cell counts of an MKN45 strain are measured and results (right) of an MTT assay, in Example 5.
Figure 18B:
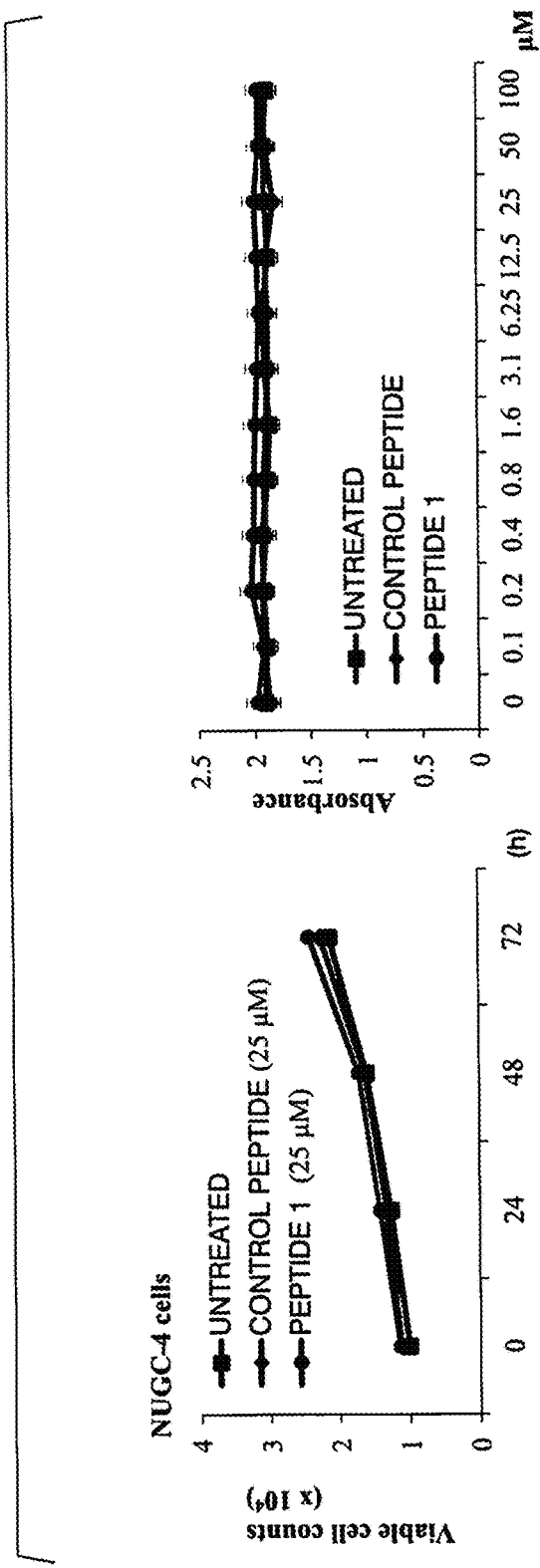
FIG. 18B is a view showing results (left) in which the viable cell counts of an NUGC-4 strain are measured and results (right) of an MTT assay, in Example 5.
Figure 19A:
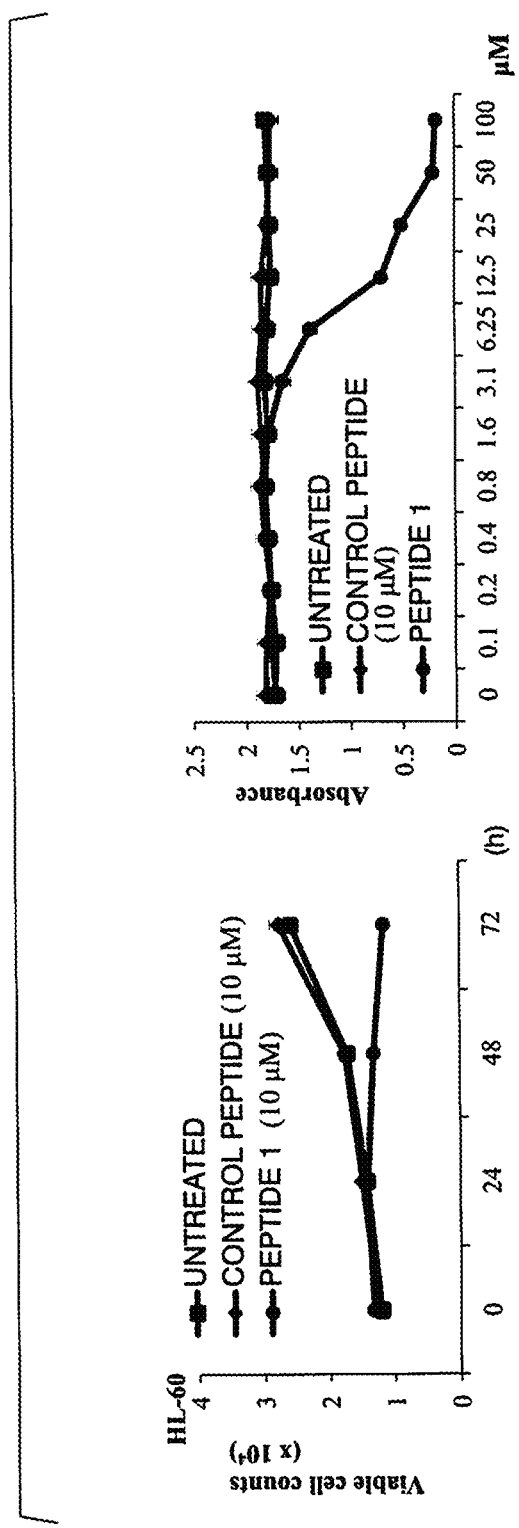
FIG. 19A is a view showing results (left) in which the viable cell counts of an HL-60 strain are measured and results (right) of an MTT assay, in Example 5.
Figure 19B:
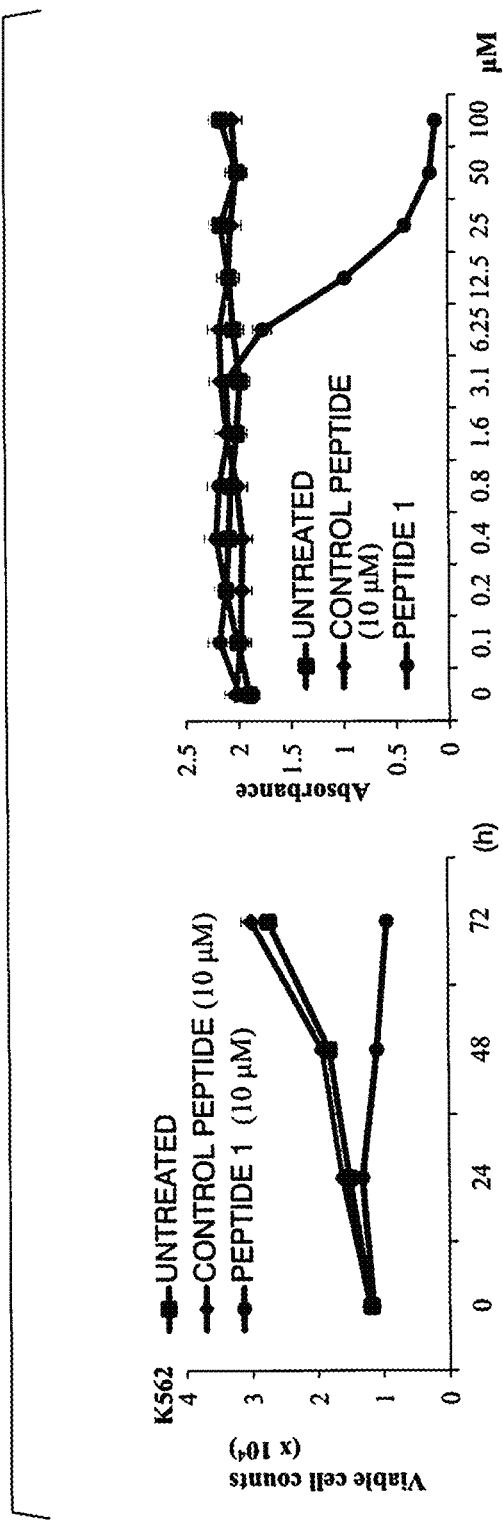
FIG. 19B is a view showing results (left) in which the viable cell counts of a K562 strain are measured and results (right) of an MTT assay, in Example 5.
Figure 19C:
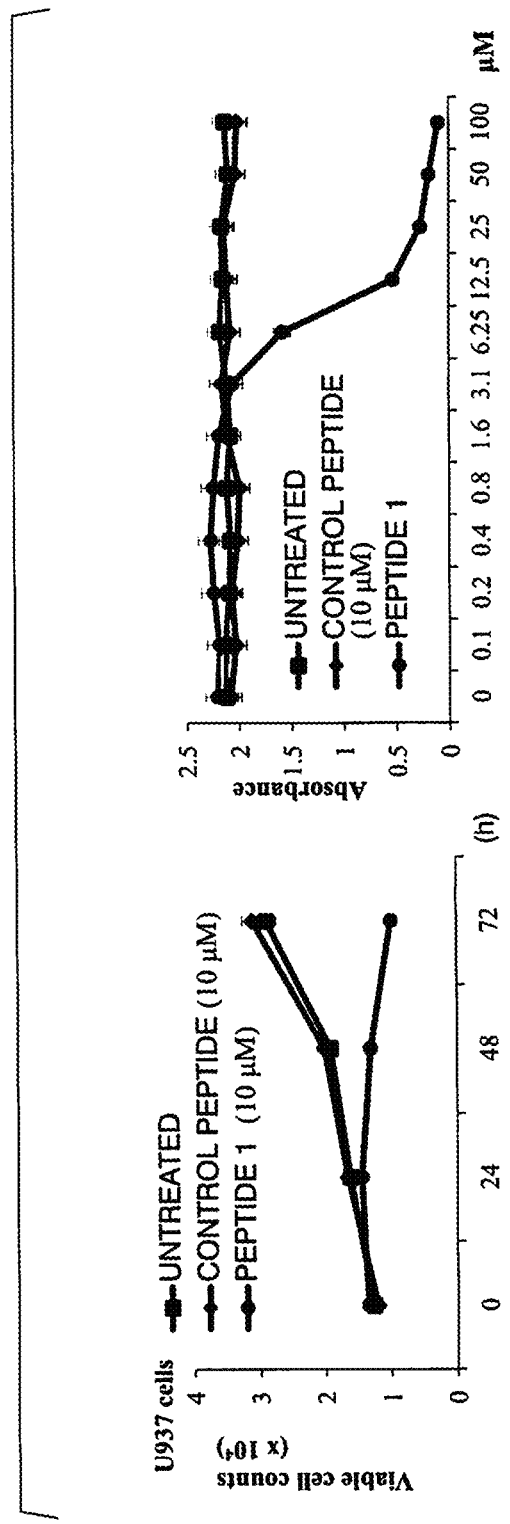
FIG. 19C is a view showing results (left) in which the viable cell counts of a U937 strain (C) are measured and results (right) of an MTT assay, in Example 5.

The measurement results (left) of the viable cell counts of each cell strain and the measurement results (right) (absorbance at 570 nm) of MTT assays are shown in FIGS. 17A to 19C. From the results, in 293 FLG/LIX1L in which a FLAG/LIX1L protein was forcibly expressed, the cell proliferation was inhibited by the introduction of the peptide 1 (FIG. 17B), but in 293 FLG in which only a FLAG protein was forcibly expressed, the cell proliferation was not inhibited by the introduction of the peptide 1 (FIG. 17A). In addition, in an MKN45 strain (FIG. 18A), the HL-60 strain (FIG. 19A), the K562 strain (FIG. 19B), and the U937 strain (FIG. 19c) in which it was confirmed that the expression level of LIX1L was large in Reference Example 6, the cell proliferation was inhibited by the introduction of the peptide 1, but in an NUGC-4 strain in which expression of LIX1L was almost not observed, the cell proliferation was not inhibited even if the peptide 1 was introduced thereinto (FIG. 18B).

Example 6

Regarding 293 FLG and 293 FLG/LIX1L, and cells in which a peptide 1 was introduced into 293 FLG/LIX1L, the numbers of colonies formed therein were compared with each other.

Specifically, 293 FLG was plated in one plate (6 wells/plate) and 293 FLG/LIX1L was plated in two plates such that the density of the cells became $1\times10^4$ cells/3.5 cm well. Among these, one of the plates in which 293 FLG was plated and the plate in which 293 FLG/LIX1L was plated were cultured for 14 days in a 10% vol. % FCS-containing DMEM culture medium. The remaining one of the plates in which 293 FLG/LIX1L was plated was cultured for 14 days in a 10% vol. % FCS-containing DMEM culture medium in which the peptide 1 was made to be included such that the concentration thereof became 25 μM. Each of the wells after the culturing was observed under a microscope, and the number of colonies formed was measured.

Figure 20:
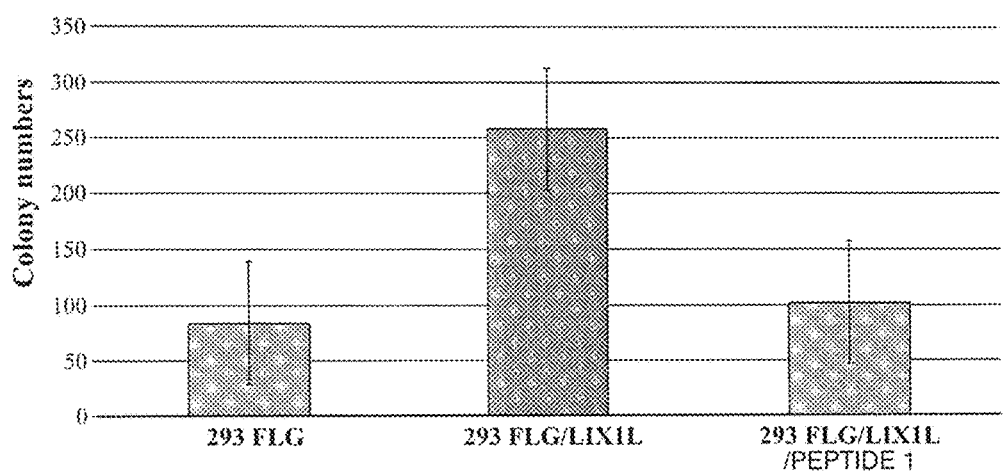
FIG. 20 is a view showing results in which the number of colonies formed in cells (293 FLG) in which only FLAG is forcibly expressed in a HEK293 strain, in cells (293 FLG/LIX1L) in which a LIX1L protein with a FLAG tag is forcibly expressed, and in cells (293 FLG/LIX1L/peptide 1) in which a peptide 1 is introduced into 293 FLG/LIX1L is measured, in Example 6.

The measurement results are shown in FIG. 20. A dominant increase in the number of colonies formed was recognized in 293 FLG/LIX1L, and it was found that the number of colonies was inhibited in the cells (293 FLG/LIX1L/peptide 1) in which the peptide 1 was introduced into 293 FLG/LIX1L.

Example 7

A peptide 1 was administered to a cancer mouse model into which a cancer cell strain was transplanted, and the influence was observed.

Rearing of 10 nude male mice (BALB/cAJcl-nu/nu, purchased from CLEA Japan, Inc.) at the age of 7 weeks was started, and MKN45 cell strains separately cultured were transplanted into the mice by being subcutaneously injected thereinto on day 31. The day on which the transplantation was performed was set as day 0, the mice were divided into two groups (peptide 1-administered group and control peptide-administered group) of 5 mice on day 14 of the transplantation, 4 mice were selected among the 5 mice from each group, and the peptide 1 or the control peptide was administered. The remaining one mouse was set as a spare. In the peptide 1-administered group, 100 μL of a 30 μM peptide 1 solution (solution prepared by adding a methylcellulose solution to the solution after the peptide 1 was dissolved in PBS (−)) was subcutaneously injected into a tumor site (site into which the MKN45 cell strain was injected) 4 times every 3 days. In the control peptide-administered group, 100 μL of a 30 μM control peptide solution (solution prepared by adding a methylcellulose solution to the solution after the control peptide was dissolved in PBS (−)) was subcutaneously injected into a tumor site 4 times on the same days as those in the peptide 1-administered group.

Figure 21:
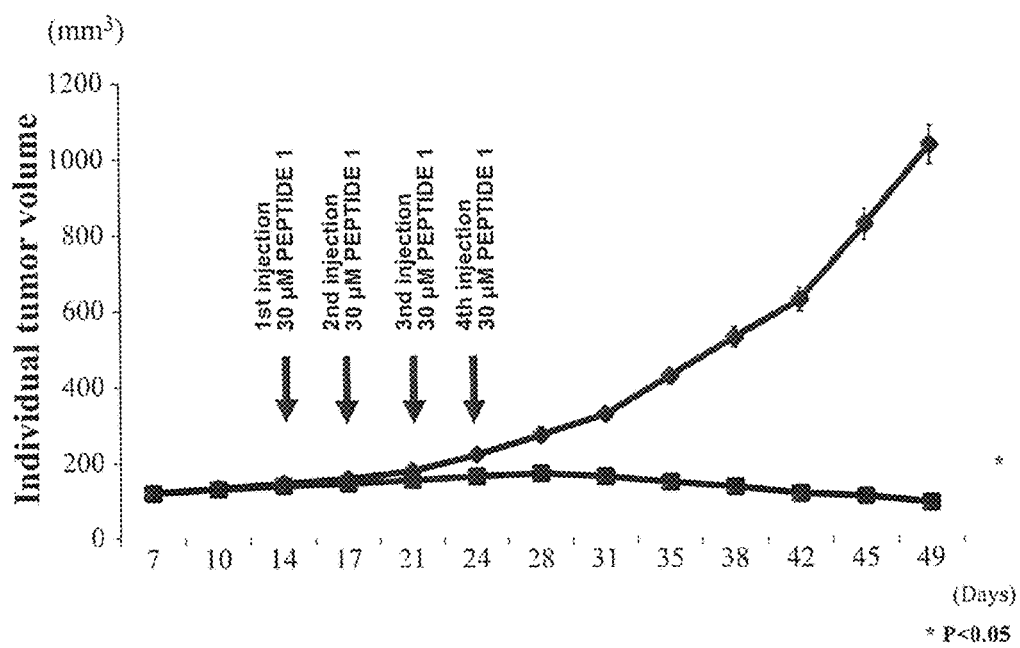
FIG. 21 is a view showing results in which the point of time at which a peptide solution is administered to each mouse and the volume of each tumor site are temporally measured, in Example 7.
Figure 22A:
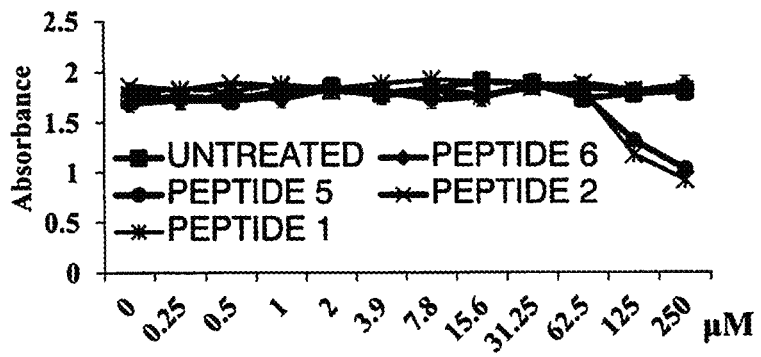
FIG. 22A is a view showing results of an MTT assay of cells (293 FLG) in which only FLAG is forcibly expressed in a Flp-In-293 strain, in Example 8.
Figure 22B:
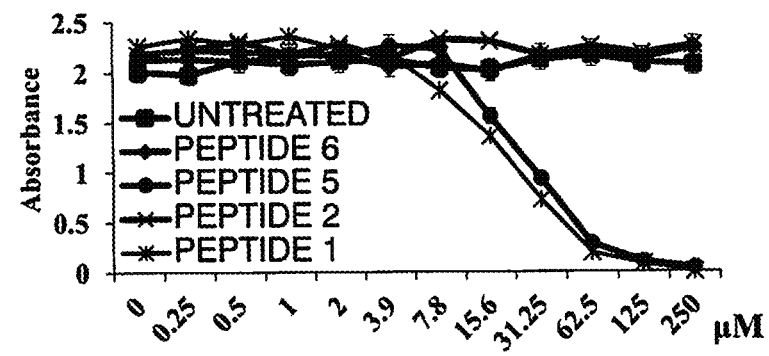
FIG. 22B is a view showing results of an MTT assay of cells (293 FLG/LIX1L) in which a LIX1L protein with a FLAG tag is forcibly expressed in a Flp-In-293 strain, in Example 8.
Figure 22C:
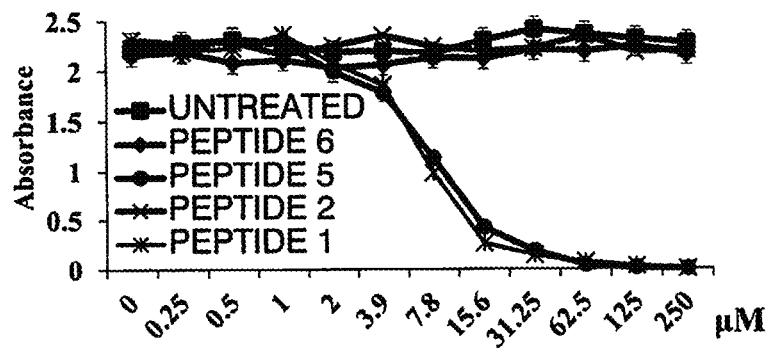
FIG. 22C is a view showing results of an MTT assay of a K562 strain, in Example 8.
Figure 22D:
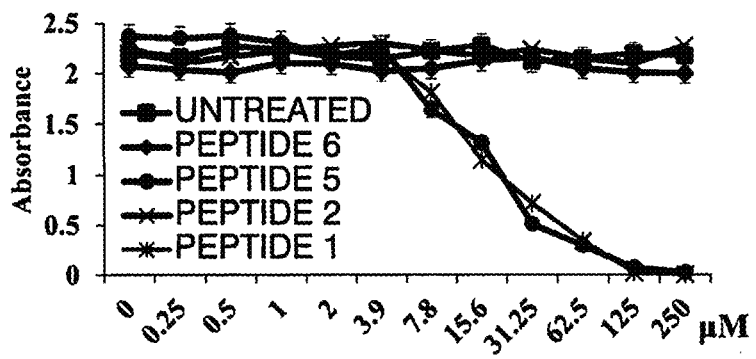
FIG. 22D is a view showing results of an MTT assay of an MKN45 strain, in Example 8.
Figure 22E:
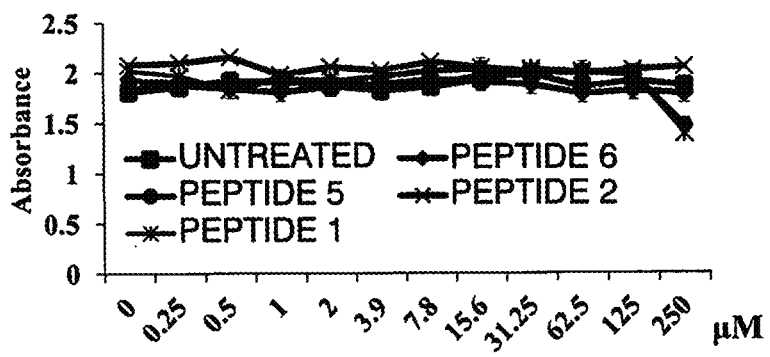
FIG. 22E is a view showing results of an MTT assay of an NUGC-4 strain, in Example 8.
Figure 23A:
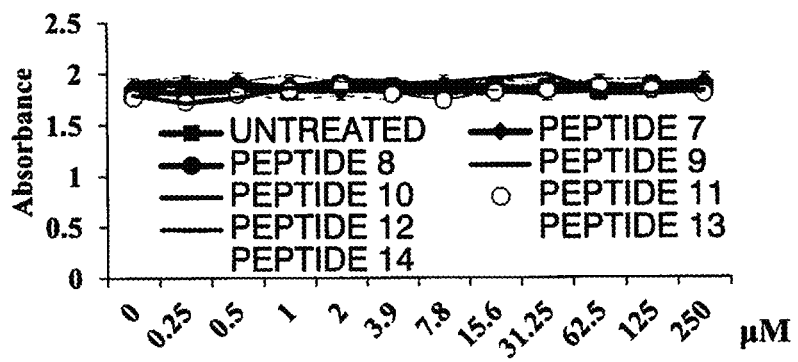
FIG. 23A is a view showing results of an MTT assay of cells (293 FLG) in which only FLAG is forcibly expressed in a Flp-In-293 strain, in Comparative Example 1.
Figure 23B:
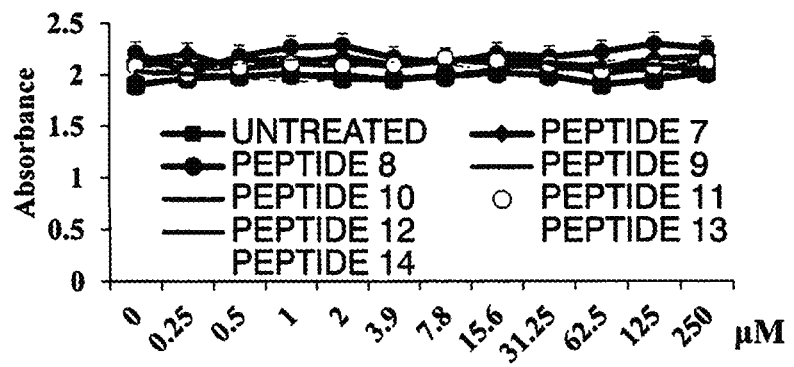
FIG. 23B is a view showing results of an MTT assay of cells (293 FLG/LIX1L) in which a LIX1L protein with a FLAG tag is forcibly expressed in a Flp-In-293 strain, in Comparative Example 1.
Figure 23C:
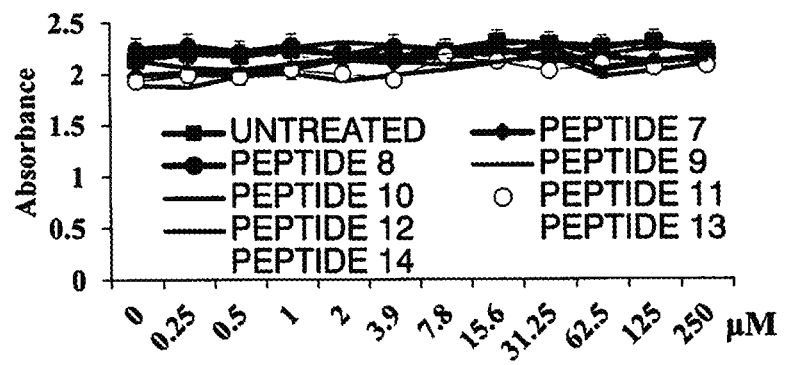
FIG. 23C is a view showing results of an MTT assay of a K562 strain, in Comparative Example 1.
Figure 23D:
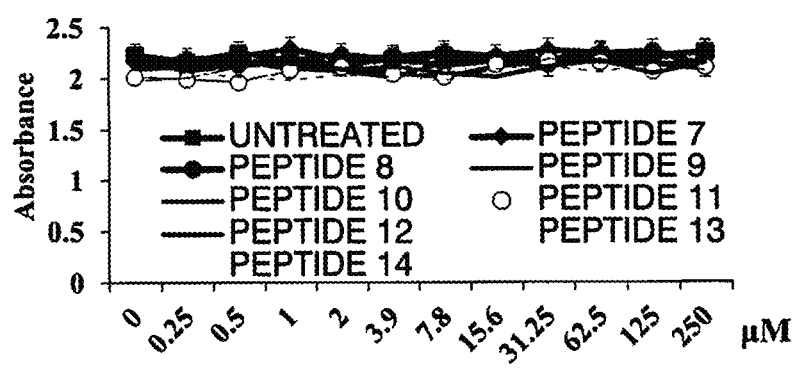
FIG. 23D is a view showing results of an MTT assay of an MKN45 strain, in Comparative Example 1.
Figure 23E:
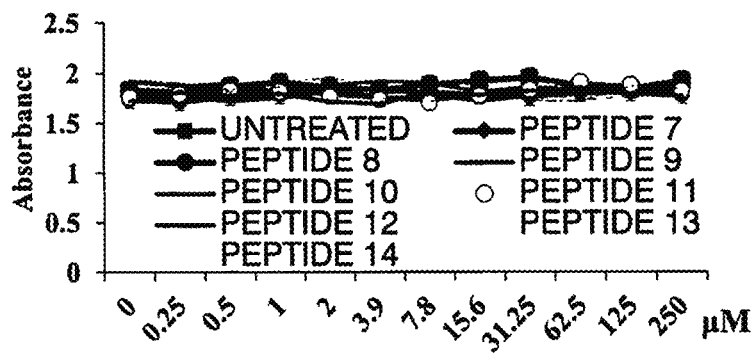
FIG. 23E is a view showing results of an MTT assay of an NUGC-4 strain, in Comparative Example 1.

The results in which the points of time (days) at which a peptide solution was administered to each mouse and the volume (mm$^3$) of a tumor site were temporally measured are shown in FIG. 21. For the volume of the tumor site, the width and the length of the tumor site determined from the appearance of the mouse were measured and calculated using the following formula.

[Volume(mm$^3$) of Tumor Site]=([Width(mm) of Tumor Site]$^2$×[Length(mm) of Tumor Site])/2

The "width of tumor site" referred herein means a maximum width of a portion in which the skin has risen due to the tumor and the "length of tumor site" means a maximum length of a portion in which the skin has risen due to the tumor.

From the results, it was observed that the size of the tumor site was rarely changed in the peptide 1-administered group whereas the volume of the tumor site became temporally large in the control peptide-administered group, and therefore, the peptide 1 had an anti-tumor effect even in a living individual. In addition, regarding the body weight, there was no particularly significant change between the spare mice, into which nothing was administered, and the control peptide-administered group and the peptide 1-administered group.

Reference Example 7

In order to check whether a peptide 1 is actually incorporated into a cell, a FAM-labeled peptide 1 obtained by bonding a fluorescent substance FAM to the C-terminal of the peptide 1 was introduced into a tumor cell strain. The presence and absence of the incorporation of the peptide 1 into a cell was observed using the fluorescence of FRM as an index.

Specifically, the FAM-labeled peptide 1 was added to each of the solutions of 293 FLG/LIX1L, which was prepared in Reference Example 5, an MKN45 strain, and an NUGC-4 strain such that the concentration thereof became 20 μM, for culturing. After the lapse of 2 hours after the addition of the FAM-labeled peptide 1, a nuclear staining agent Hoechst 33342 (manufactured by Dojindo Laboratories Co., Ltd.) was further added to each of the solutions for culturing for 60 minutes. Thereafter, each of the cells was observed using a fluorescence microscope.

As a result, it was confirmed that the FAM-labeled peptides 1 were incorporated into the cells in all of 293 FLG/LIX1L, the MKN45 strain, and the NUGC-4 strain. Particularly, in 293 FLG/LIX1L and the MKN45 strain, the FAM-labeled peptides 1 were incorporated into 90% or more cells after the lapse of 2 hours after the addition thereof. In addition, in all of the three strains, most of the FAM-labeled peptides 1 incorporated into the cells were recognized in cytoplasm.

Example 8

It was expected that Y95, Y136, and Y139 among five tyrosine residues in a LIX1L protein were phosphorylated. MTT assays were performed on four kinds of peptides shown in Table 1, similarly to Example 2, and the influence on the cell proliferation was examined. In Table 1, "X" represents ε-aminocaproic acid. In addition, as cells into which peptides were introduced, 293 FLG and 293 FLG/LIX1L prepared in Reference Example 5, a K562 strain, an MKN45 strain, and an NUGC-4 strain were used.

TABLE 1

| | Y residues contained | Amino acid sequence | SEQ ID No: |
|---|---|---|---|
| Peptide 6 | Y95 | YGRKKRRQRRR-X-HTQGYGRVNV-NH$_2$ | 19 |
| Peptide 5 | Y136, Y139 | YGRKKRRQRRR-X-PSNSPPYVCY-NH$_2$ | 18 |

TABLE 1-continued

| | Y residues contained | Amino acid sequence | SEQ ID No: |
|---|---|---|---|
| Peptide 1 | Y136, Y139 | YGRKKRRQRRR-X-PSNSPPYVCYV-NH₂ | 12 |
| Peptide 2 | Y139 | YGRKKRRQRRR-X-CYVTLPGGSC-NH₂ | 13 |

Specifically, the cells were cultured for 72 hours similarly to Example 2 except that a peptide to be added to a cell was set to a peptide 1, 2, 5, or 6, MTT assays were performed thereon, and the absorbance at 570 nm was measured. As a comparison, culturing was performed similarly to the above using a culture solution containing no peptide, and the MTT assay was performed thereon (untreated).

The results of an MTT assay of each cell strain are shown in FIGS. 22A to 22E. From the results, a tendency was observed in which cell proliferation was inhibited in all of the cell strains by making the concentration of a peptide to be added to a cell strain high, in cases where the peptide 1 and the peptide 5 were added to the cell strains. However, in the peptide 2 and the peptide 6, the cell proliferation was not inhibited even if the peptides at 250 μM were added to the cell strains.

Comparative Example 1

There are 26 serine residues in a LIX1L protein. The probability of phosphorylation of these serine residues was predicted and peptides shown in Table 2 were synthesized with respect to 11 residues (S16, S163, S179, S190, S192, S226, S255, S282, S286, S292, and S297) for which it was expected that there is a high probability of phosphorylation. MTT assays were performed thereon similarly to Example 2 and the influence on cell proliferation was examined. In Table 2, "X" is the same as that in Table 1. In addition, as cells into which the peptides were introduced, the 293 FLG and 293 FLG/LIX1L prepared in Reference Example 5, a K562 strain, an MKN45 strain, and an NUGC-4 strain were used.

TABLE 2

| | S residues contained | Amino acid sequence | SEQ ID No: |
|---|---|---|---|
| Peptide 7 | S16 | YGRKKRRQRRR-X-GVGTSGRGTL-NH₂ | 20 |
| Peptide 8 | S163 | YGRKKRRQRRR-X-EARRSAAKIA-NH₂ | 21 |
| Peptide 9 | S179 | YGRKKRRQRRR-X-NEHPSRRITD-NH₂ | 22 |
| Peptide 10 | S190, S192 | YGRKKRRQRRR-X-FIEKSVSEAL-NH₂ | 23 |
| Peptide 11 | S226 | YGRKKRRQRRR-X-NKGKSMLEFQ-NH₂ | 24 |
| Peptide 12 | S255 | YGRKKRRQRRR-X-ERQCSRQEVL-NH₂ | 25 |
| Peptide 13 | S282, S286 | YGRICICRRQRRR-X-DWVSREQSVP-NH₂ | 26 |

TABLE 2-continued

| | S residues contained | Amino acid sequence | SEQ ID No: |
|---|---|---|---|
| Peptide 14 | S292, S297 | YGRKKRRQRRR-X-ALSRELASTE-NH₂ | 27 |

Specifically, the cells were cultured for 72 hours similarly to Example 2 except that peptides to be added to cell strains were set to peptides 7 to 14, MTT assays were performed thereon, and the absorbance at 570 nm was measured. As a comparison, culturing was performed similarly to the above using a culture solution containing no peptide, and the MTT assay was performed thereon (untreated).

The results of an MTT assay of each cell strain are shown in FIGS. 23A to 23E. The results were that, in all peptides, the cell proliferation was not inhibited even if the peptides at 250 μM were added to all of the cell strains.

Comparative Example 2

There are 13 threonine residues in a LIX1L protein. The probability of phosphorylation of these serine residues was predicted and peptides shown in Table 3 were synthesized with respect to 3 residues (T15, T20, and T298) for which it was expected that there is a high probability of phosphorylation. MTT assays were performed thereon similarly to Example 2 and the influence on cell proliferation was examined. In Table 3, "X" is the same as that in Table 1. In addition, as cells into which the peptides were introduced, the 293 FLG and 293 FLG/LIX1L prepared in Reference Example 5, a K562 strain, an MKN45 strain, and an NUGC-4 strain were used.

TABLE 3

| | T residues contained | Amino acid sequence | SEQ ID No: |
|---|---|---|---|
| Peptide 15 | T15, T20 | YGRKKRRQRRR-X-VGTSGRGTLR-NH₂ | 28 |
| Peptide 16 | T298 | TGRKKRRQRRR-X-ELASTERELD-NH₂ | 29 |

Specifically, the cells were cultured for 72 hours similarly to Example 2 except that a peptide to be added to a cell strain was set to a peptide 15 or 16, an MTT assay was performed thereon, and the absorbance at 570 nm was measured. As a comparison, culturing was performed similarly to the above using a culture solution containing no peptide, and the MTT assay was performed thereon (untreated).

Figure 24A:
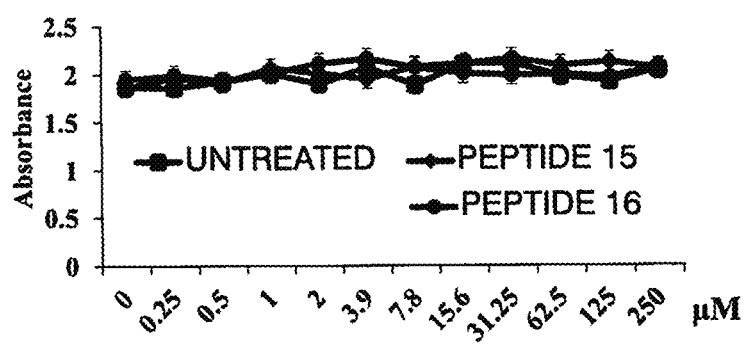
FIG. 24A is a view showing results of an MTT assay of cells (293 FLG) in which only FLAG is forcibly expressed in a Flp-In-293 strain, in Comparative Example 2.
Figure 24B:
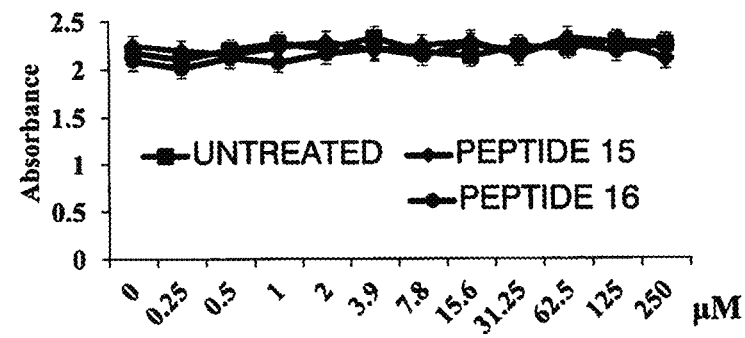
FIG. 24B is a view showing results of an MTT assay of cells (293 FLG/LIX1L) in which a LIX1L protein with a FLAG tag is forcibly expressed in a Flp-In-293 strain, in Comparative Example 2.
Figure 24C:
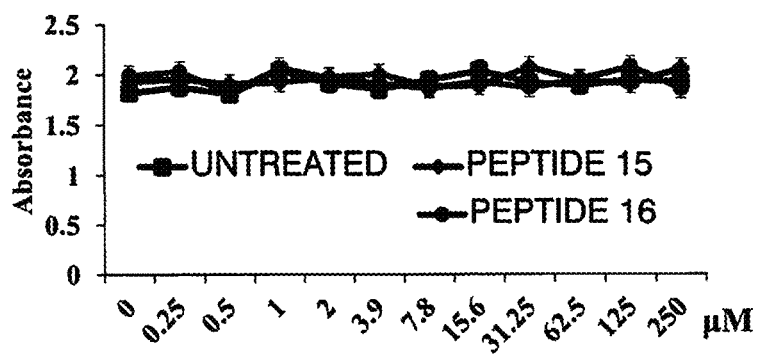
FIG. 24C is a view showing results of an MTT assay of a K562 strain, in Comparative Example 2.
Figure 24D:
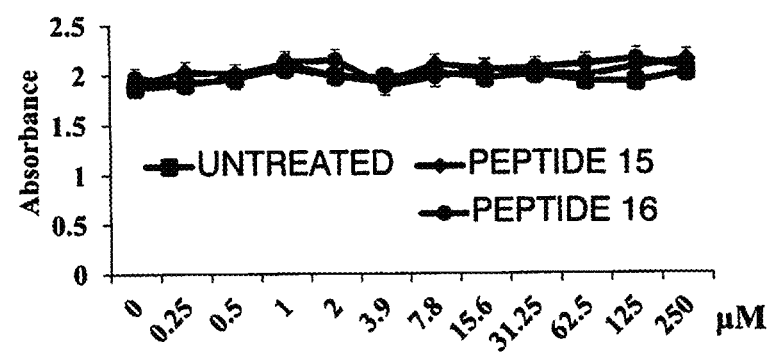
FIG. 24D is a view showing results of an MTT assay of an MKN45 strain, in Comparative Example 2.
Figure 24E:
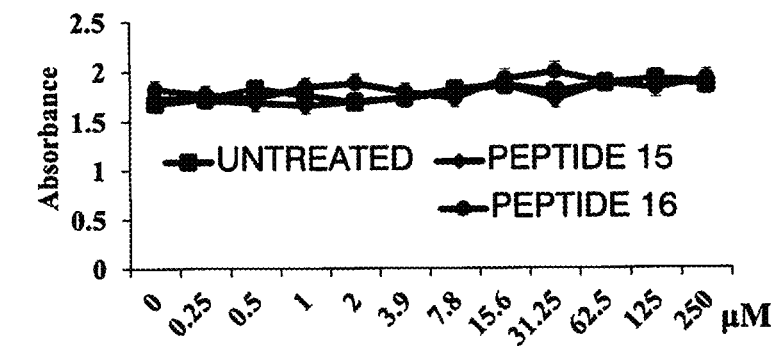
FIG. 24E is a view showing results of an MTT assay of an NUGC-4 strain, in Comparative Example 2.

The results of an MTT assay of each cell strain are shown in FIGS. 24A and 24B. The results were that, in all peptides, the cell proliferation was not inhibited even if the peptides at 250 μM were added to all of the cell strains.

Example 9

Cells (293 FLG) in which only FLAG was forcibly expressed in a HEK293 strain, cells (293 FLG/LIX1L) in which a LIX1L protein with a FLAG tag was forcibly expressed, and cells (293 FLG/LIX1L/PY136) in which a peptide 1 (PY136) was introduced into 293 FLG/LIX1L were separated into cytoplasm fractions and nuclear fractions; and the effect of inhibiting tyrosine phosphorylation of LIX1L due to the peptide 1 (SEQ ID No: 12) through immunoprecipitation and Western blotting was examined. In addition, the effect of inhibiting the formation of colonies through colony formation assay was examined.

First, a cell strain (293 FLG) in which only FLAG was forcibly expressed, a cell strain (293 FLG/LIX1L) in which a LIX1L protein with a FLAG tag was forcibly expressed, and a cell strain (293 FLG/LIX1L/PY136) in which a LIX1L protein with a FLAG tag for adding a peptide thereto was forcibly expressed were prepared through the same method as Reference Example 5, and were cultured and proliferated.

Next, the 293 FLG/LIX1L/PY136 cells were cultured for 14 days in a culture solution containing a peptide 1 through the same method as that in Example 3. The 293 FLG cells and the 293 FLG/LIX1L cells were cultured for 14 days in the same manner as above using a culture solution containing no peptide 1.

Next, the 293 FLG cells, the 293 FLG/LIX1L cells, and the 293 FLG/LIX1L/PY136 cells were respectively cultured in 10% FCS-containing DMEM culture media to which Hygromycin B at 100 mg/mL was added, for 14 days. Then, the cultured cells were separated into nuclear fractions and cytoplasm fractions using Nuclear/Cytosol Fractionation Kit (manufactured by BioVison, Inc.). Immunoprecipitation was performed on both the obtained fractions using an anti-FLAG antibody (manufactured by Sigma-Aldrich Co. LLC.) and an agarose-binding protein A (manufactured by Sigma-Aldrich Co. LLC.), protein separation was performed thereon through 12% SDS-PAGE, and the fractions were transferred to a film. Western blotting was performed on the fractions-transferred film using an anti-LIX1L antibody (manufactured by Abnova Corporation) and an anti-phosphorylated tyrosine antibody (manufactured by Abcam plc.).

Figure 25A:
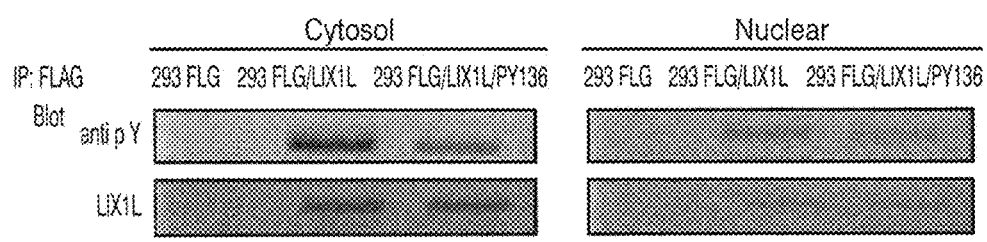
FIG. 25A is a view showing results in which cells (293 FLG) in which only FLAG is forcibly expressed in a HEK293 strain, cells (293 FLG/LIX1L) in which a LIX1L protein with a FLAG tag is forcibly expressed, and cells (293 FLG/LIX1L/PY136) in which a peptide 1 is introduced into 293 FLG/LIX1L are separated into cytoplasm fractions and nuclear fractions; immunoprecipitation using an anti-FLAG antibody is performed on lysates thereof; and Western blotting is performed on the obtained precipitate using a tyrosine phosphorylation antibody, in Example 9.

The results of Western blotting of immunoprecipitates using an anti-LIX1L antibody and an anti-phosphorylated tyrosine antibody are shown in FIG. 25A. From the results, it was found that the phosphorylation of the 136th tyrosine of LIX1L was significantly inhibited in a cytoplasm fraction of a 293 FLG/LIX1L/PY136 cell treated using the peptide 1. In addition, it was found that the phosphorylation of the 136th tyrosine of LIX1L was slightly inhibited even in a nuclear fraction.

In the colony formation assay, the 293 FLG cells, the 293 FLG/LIX1L cells, and the 293 FLG/LIX1L/PY136 cells were respectively mixed in 10% FCS-containing DMEM culture media, to which 0.4% agarose was added, and the mixtures were gently placed on 0.6% agarose- and 10% FCS-containing DMEM culture media for culturing for 14 days. Thereafter, the influence of LIX1L and PY136 on cell proliferation was evaluated by counting the number of colonies in each well using an optical microscope (manufactured by Zeiss).

Figure 25B:
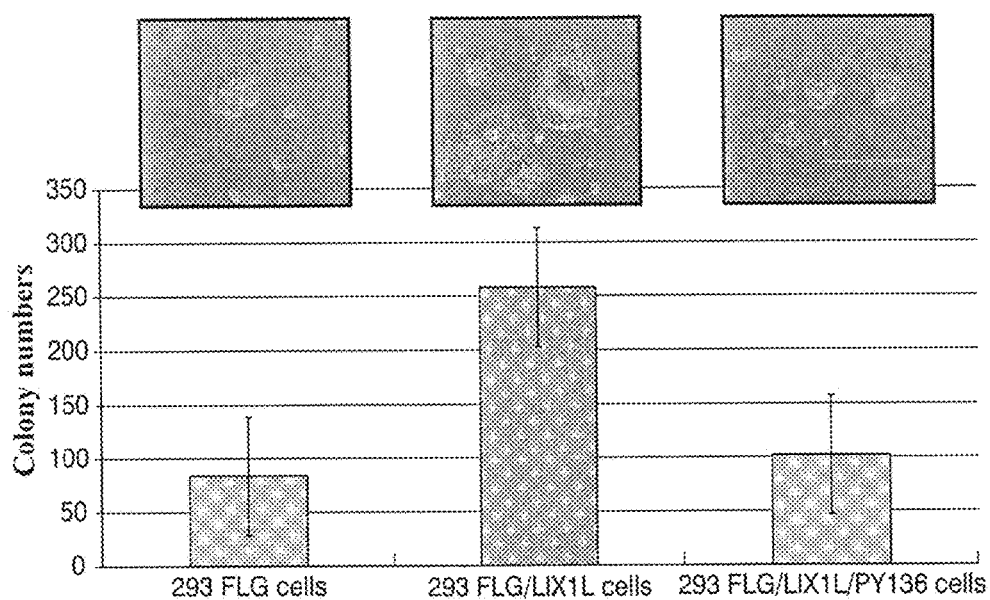
FIG. 25B is a view showing results in which a colony formation assay is performed on cells (293 FLG) in which only FLAG is forcibly expressed in a HEK293 strain, cells (293 FLG/LIX1L) in which a LIX1L protein with a FLAG tag is forcibly expressed, and cells (293 FLG/LIX1L/PY136) in which a peptide 1 is introduced into 293 FLG/LIX1L; and the state of colonies photographed by an optical microscope, in Example 9.

The results in which the colony formation assay is performed on the 293 FLG cells, the 293 FLG/LIX1L cells, and the 293 FLG/LIX1L/PY136 cells are shown in FIG. 25B. From the results, it was found that the formation of colonies was significantly inhibited in the 293 FLG/LIX1L/PY136 cells treated using the peptide 1.

INDUSTRIAL APPLICABILITY

Since the proliferation of a high LIX1L-expressing tumor cell can be inhibited using a tumor cell proliferation-inhibiting peptide and a method for inhibiting proliferation of a high LIX1L-expressing tumor cell according to the present invention, it is possible to use this tumor cell proliferation-inhibiting peptide or the like in fields of developing or producing an anti-tumor agent and treating a tumor, and therefore, is extremely effective industrially.

The invention claimed is:

1. A method for inhibiting proliferation of a high LIX1L-expressing tumor cell, comprising:
   inhibiting the expression or function of a LIX1L gene in the high LIX1L-expressing tumor cell.

2. The method for inhibiting proliferation of a high LIX1L-expressing tumor cell according to claim 1,
   wherein the expression of a LIX1L gene in the high LIX1L-expressing tumor cell is inhibited by RNA interference.

3. The method for inhibiting proliferation of a high LIX1L-expressing tumor cell according to claim 2,
   wherein the inhibition of the expression of a LIX1L gene through RNA interference includes introduction of shRNA or siRNA which includes a base sequence represented by SEQ ID No: 3 or 4, or a vector which produces the shRNA or the siRNA in a cell, into the high LIX1L-expressing tumor cell.

4. The method for inhibiting proliferation of a high LIX1L-expressing tumor cell according to claim 1, further comprising:
   inhibiting phosphorylation of a tyrosine amino acid of a LIX1L protein in the high LIX1L-expressing tumor cell.

5. The method for inhibiting proliferation of a high LIX1L-expressing tumor cell according to claim 4,
   wherein the tyrosine whose phosphorylation is inhibited is the 136th amino acid of SEQ ID No: 1.

* * * * *